United States Patent
Wiltfang et al.

(10) Patent No.: US 6,849,416 B2
(45) Date of Patent: Feb. 1, 2005

(54) MONOCLONAL ANTIBODY

(76) Inventors: Jens Wiltfang, Hofer Strasse 15a, 91056 Erlangen (DE); Thomas Dyrks, C/o Schering AG, D-13342 Berlin (DE); Ursula Mönning, C/o Schering AG, D-13342 Berlin (DE)

( * ) Notice: Subject to any disclaimer, the term of this patent is extended or adjusted under 35 U.S.C. 154(b) by 163 days.

(21) Appl. No.: 10/170,272

(22) Filed: Jun. 11, 2002

(65) Prior Publication Data

US 2003/0166019 A1 Sep. 4, 2003

(30) Foreign Application Priority Data

Jun. 12, 2001 (EP) ............................................ 01114192

(51) Int. Cl.⁷ ...................... G01N 33/53; G01N 33/577; C07K 16/00
(52) U.S. Cl. ................ 435/7.21; 530/387.1; 530/388.1; 530/391.1; 530/391.3
(58) Field of Search ...................... 435/7.21; 530/387.1, 530/388.1, 391.1, 391.3

(56) References Cited

PUBLICATIONS

Chevallier, et al.; Cathepsin D Displays in Vitro Beta–Secretase–Like Specificity; 1997; pps. 11–19.

Takaomi Comings Saido, et al.; Spatial Resolution of the Primary Beta–Amyloidogenic Process Induced in Postischemic Hippocampus; The Journal of Biologial Chemistry; 1994; pps. 15253–15257.

Aria, et al: Immunohistochemical Localization of Amyloid Beta–Protein With Amino–Terminal Aspartate in the Cerebral Cortex of Patients with Alzheimer's Disease; Brain Research; 1999; pps. 202–206.

Wiltfang, et al.; Improved Electrophoretic Separation and Immunoblotting of Beta–Amyloid Peptides 1–40, 1–42, and 1–43; Electrophoresis; 1997; pps. 527–532.

Klafki, et al; Electrophoretic Separation of Beta–A4 Peptides; 1996; pps. 24–29.

*Primary Examiner*—Elizabeth Kemmerer
*Assistant Examiner*—Christopher James Nichols
(74) *Attorney, Agent, or Firm*—Thomas, Kayden, Horstemeyer & Risley, LLP

(57) ABSTRACT

A monoclonal antibody which is referred to as mAb 1E8, which was deposited at the DSMZ-Deutsche Sammlung von Mikroorganismen und Zellkulturen GmbH, Braunschweig, on Dec. 19, 2000 and which was assigned the DSMZ accession number DSM ACC2485, can be used for detecting Aβ peptides Aβ1-x and Aβ2-x, and sAPPα.

27 Claims, 30 Drawing Sheets

MONOCLONAL ANTIBODY

TECHNICAL FIELD

The invention relates to a monoclonal antibody and to the use of the antibody for detecting Aβ peptides and/or sAPPα. It is concerned in particular with the neurochemical diagnosis of neuropsychatric disorders both with inspection of Aβ peptide concentrations and, in this connection, again in particular with the diagnosis of dementia on body fluid or tissue samples.

BACKGROUND OF THE INVENTION

The German journal Psycho, 24 (1998), 726–731, discloses that reduced concentrations of Aβ1-42 are detectable in the CSF of patients with Alzheimer's disease. In these patients there is also a tendency for the concentration of N-terminally modified Aβ peptides Aβx-42 to be increased. By contrast, there are said to be no changes in concentration of the Aβ peptide Aβ1-40 because of Alzheimer's disease. The concentrations of the Aβ peptides Aβ1-42 and Aβ1-40 in the CSF of Alzheimer patients are said to show no absolute correlation with clinical or psychological test parameters of the severity of the dementia, although there is said to be great intraindividual constancy thereof.

There is known to be evidence that sAPPα is also reduced in the CSF in Alzheimer dementia.

In order to obtain more detailed information about the correlation of dementing disorders and possibly other neuropsychatric disorders with the concentration of all or certain of the Aβ peptides in samples of body fluids or tissues it is necessary to have means available for very accurate and reproducible determination of the concentrations of the Aβ peptides, so that existing correlations are not obscured by unavoidable errors in the concentration determinations.

SUMMARY OF THE INVENTION

The invention is therefore based on the primary object of providing a means for accurate and reproducible determination of concentrations of Aβ peptides in a sample of body fluid or tissue. A further objective is to optimize the use of this means and to derive from the correlations which can be measured therewith between Aβ peptide concentrations and neuropsychatric disorders predictions which can be used in the future neurochemical diagnosis of neuropsychatric disorders.

The means with which the object of the invention is achieved is the monoclonal antibody which is referred to as mAb 1E8 (cell culture UM 1998 clone 1E8), which was deposited at the DSMZ-Deutsche Sammlung von Mikroorganismen und Zellkulturen GmbH, Braunschweig, on Dec. 19, 2000, and which was assigned the DSMZ accession number DSM ACC2485. The physical address for the DSMZ is: DSMZ—Deutsche Sammlung von Mikroorganismen und Zellkulturen GmbH, Mascheroder Weg 1b, 38124 Braunschweig, GERMANY.

The antibody mAb 1E8 may be radiolabeled. However, it can also be used in conjunction with a secondary antibody for labeling thereof.

It has emerged that the antibody mAb 1E8 binds with high selectivity and specificity to Aβ peptides Aβ1-x and Aβ2-x and to soluble β-amyloid precursor protein after α-secretase cutting (sAPPα). This creates the conditions for it to be possible to determine the concentration of these peptides with the antibody mAb 1E8.

The antibody mAb 1E8 can be used in a Western imunoblott. It is possible in this case to increase the effective selectivity of the antibody mAb 1E8 by blocking nonspecific binding sites with a blocking agent before the use of the antibody. A synthetic reagent which is obtainable under the proprietary name "ROTI-BLOCK" has proved in this connection to be very advantageous compared with a conventional use of milk powder as blocking agent, because it increases the effective avidity—and thus the sensitivity of detection—of the antibody mAb 1E8 while the selectivity is substantially retained. This does not apply generally because, for example, another commercially available mAb (6E10) is not compatible with this method.

Since the antibody mAb 1E8 recognizes both Aβ peptides Aβ1-x and Aβ peptides Aβ2-x and sAPPα, these peptides must be separated from one another for selective detection. This is possible by sodium lauryl sulfate polyacrylamide gel electrophoresis (SDS-PAGE). However, in a conventional SDS-PAGE, only the Aβ peptides Aβ1-x and/or Aβ2-x overall are separated from the sAPPα, because the effective molecular sizes of the Aβ peptides Aβ1-x and/or Aβ2-x are not sufficiently different. However, it is possible by addition of urea, and additionally dependent on the detergent concentration, gel pore size, pH and temperature, to induce an amino acid primary sequence-specific conformational change in the Aβ peptides, which makes it possible to distinguish the migration distances in the SDS-PAGE of the Aβ peptides Aβ1-x and Aβ2-x, which differ in length at the carboxy terminus. This method is also referred to herein as Aβ-SDS-PAGE.

The Aβ peptides can be separated from other substances present in the particular sample of body fluid or tissue beforehand by isoelectric focussing in a direction perpendicular to the direction of the SDS-PAGE.

It is thus possible with use of the antibody mAb 1E8 to determine, in a sample which is selected from the group which comprises CSF, brain homogenate, plasma and mixtures thereof, a concentration of the Aβ peptide Aβ1-42, for which it is already known that absolute increases in brain homogenate and reduction in the CSF thereof occur for example in correlation with Alzheimer's diseases.

However, it is also possible with use of the antibody mAb 1E8 to examine a sample which is selected from the group which comprises CSF, brain homogenate and mixtures thereof for the presence of a detectable concentration of the Aβ peptide Aβ2-42. Such a limit of detection is 100 pg/ml or above. When it is exceeded, it is possible to conclude that the patent from whom the sample originates has a dementing disorder from the group of protein folding diseases. The group of protein folding diseases includes not only Alzheimer's disease but also Lewy body dementia and Creutzfeldt-Jakob disease. High concentrations of the Aβ peptide Aβ2-42 were detectable in CSF samples from many patients with these diseases.

Analysis of plasma samples is difficult here, in contrast to the uses of the antibody mAb 1E8 described previously, because the concentration of the Aβ peptide Aβ2-42 is at the limit of detection even in the CSF, and the natural concentration of the Aβ peptides in plasma is distinctly lower than in CSF. In order to obtain equally high concentrations in the samples, it is therefore always necessary to carry out a concentration step in the plasma, for example by immunoprecipitation with the antibody mAb 1E8, before the actual concentration determination.

An increase in the ratio between the concentration of the Aβ peptide Aβ2-42 to the concentration of the Aβ peptide Aβ1-42 in the particular sample has proved to be particularly significant for the presence of a dementing disorder from the group of protein folding diseases. In these dementing disorders there is evidently a process which promotes production of the Aβ peptide Aβ2-42 at the expense of the production of the Aβ peptide Aβ1-42.

The use of the antibody mAb 1E8 opens up other neurochemical diagnostic possibilities too. Thus, it is possible in a sample selected from the group which comprises CSF, brain homogenate, plasma and mixtures thereof to determine at least one concentration ratio which is selected from the group which comprises a ratio between a concentration of the Aβ peptide Aβ1-42 to a concentration of the Aβ peptide Aβ1-40, a ratio between a concentration of the Aβ peptide Aβ1-42 to a concentration of the Aβ peptide Aβ1-38 and a ratio between a concentration of the Aβ peptide Aβ1-38 to a concentration of the Aβ peptide Aβ1-40. Determinations of these concentration ratios are based on the novel finding that significant shifts in this relative concentration of Aβ peptides occur in various neuropsychatric disorders compared with a comparison group of patients.

Thus, if the Aβ1-38/Aβ1-40 concentration ratio is below a predetermined limit on comparison thereof with the limit, it is possible to conclude that Alzheimer's disease is present. This limit in CSF is typically between 0.285 and 0.300. These numerical data relate, like all other numerical data unless otherwise indicated in the individual case, to CSF samples which have in each case been frozen once for preservation after they have been obtained.

Conversely, if this Aβ1-38/Aβ1-40 concentration ratio exceeds a different limit on comparison it is possible to conclude that a chronic inflammatory disorder of the central nervous system is present. This limit in CSF is typically between 0.250 and 0.260. It is thus in fact below the limit below which it is concluded that Alzheimer's disease is present. The overlap is, however, only small. In this connection it must also be seen that the diagnoses made here are to be seen in the framework of a differential diagnosis. Thus, if the limit for Alzheimer's disease is exceeded, it can be precluded with relative certainty that such a disease is present. Conversely, below the limit for a chronic inflammatory disorder of the central nervous system it is possible to conclude that no such disorder is present.

When the Aβ1-42/Aβ1-40 concentration ratio is below a predetermined limit it also indicates that Alzheimer's disease is present. The limit in this case in CSF is typically between 0.130 and 0.145.

With the 1-42/Aβ1-38 concentration ratio it has emerged that when the latter satisfies an inequality:

$$A*A\beta1\text{-}42/A\beta1\text{-}38 + B > A\beta1\text{-}38/A\beta1\text{-}40$$

Together with the Aβ1-38/Aβ1-40 concentration ratio, the presence of Alzheimer's disease is indicated, where A and B are constants for which the following apply in CSF $$0.2 < A < 0.8 \text{ and}$$

$$0.5*A < B < 2*A \text{ and}$$

$$B < 0.9$$

The neurochemical diagnostic possibilities described hereinbefore and hereinafter were admittedly developed using the antibody mAb 1E8. However, they can be implemented in just the same way with other means for determining the concentrations of the individual Aβ peptides Aβ1-x and Aβ2-x. In these cases there may be shifts in the stated limits due to different specificities of the means for detecting the individual Aβ peptides relative to the specificities of the antibody mAb 1E8.

Besides the concentration ratios which have been mentioned previously between the concentrations of individual Aβ peptides, it has emerged that relative proportions of individual Aβ peptides in the total of an Aβ peptide present can likewise be evaluated diagnostically in relation to neuropsychiatric disorders. Thus, in a sample which is selected from the group which comprises CSF, brain homogenate, plasma and mixtures thereof it is possible to determine at least one relative proportion Aβ1-n % of a concentration of an Aβ peptide Aβ1-n in a concentration of Aβ peptide Aβ1-x, where the relative proportion Aβ1-n % is selected from the group which comprises a relative proportion Aβ1-42% of a concentration of the Aβ peptide Aβ1-42, a relative proportion Aβ1-40% of a concentration of the Aβ peptide Aβ1-40 and a relative proportion Aβ1-38% of a concentration of the Aβ peptide Aβ1-38, and where the concentration of Aβ peptides Aβ1-x comprises at least the concentration of the Aβ peptides Aβ1-38, Aβ1-40 and Aβ1-42 from the group of Aβ peptides Aβ1-37, Aβ1-38, Aβ1-39, Aβ1-40 and Aβ1-42.

It is possible with the antibody mAb 1E8 and with suitable methodology to determine the concentrations of all Aβ peptides mentioned in addition to that of sAPPα. The highest concentrations are found with the Aβ peptides Aβ1-38, Aβ1-40 and Aβ1-42. With these Aβ peptides there are also significant changes in the relative proportions if neuropsychatric disorders occur. Because of the dominance of the Aβ peptides Aβ1-38, Aβ1-40 and Aβ1-42 it is sufficient to determine the relative proportions in relation to this group of three mainly occurring Aβ peptides. However, it is also possible and sensible to take account of all five of the abovementioned Aβ peptides as basis for the relative proportions. The concentrations on only the three mainly occurring Aβ peptides also makes it possible to carry out the diagnosis described herein with the aid of other methods for concentration determination. Thus, the concentrations of the three Aβ peptides Aβ1-38, Aβ1-40 and Aβ1-42 can be measured for example with specific assays for these three Aβ peptides.

It has emerged from analysis of the relative proportion Aβ1-38% that when the latter exceeds a predetermined limit it indicates the presence of a chronic inflammatory disorder of the central nervous system, where this predetermined limit is typically, and on use of the antibody mAb 1E8 for determination of the concentrations of the Aβ peptides in the CSF, between 15.0 and 15.7%.

Analysis of the relative proportion Aβ1-42% has revealed that where it is below a predetermined limit it indicates the presence of Alzheimer's disease. This predetermined limit is between 8 and 9%. On use of the antibody mAb 1E8 for determining the concentrations of Aβ peptides in the CSF it can be restricted to the range 8.3 to 8.8%.

At the same time, the presence of a chronic inflammatory disorder of the central nervous system is indicated by the relative proportion Aβ1-42% exceeding a predetermined limit. This limit in CSF is between 9.1 and 9.6%.

The relative proportion Aβ1-40% indicates the presence of Alzheimer's disease if a predetermined limit, which is typically between 59 and 61% in CSF, is exceeded.

There is a positive correlation between the severity of Alzheimer's dementia reflected by the mini mental status examination (MMSE, score 0–30; 27–20: mild dementia; score 19–11: moderate dementia; score 10–0: severe dementia), and Aβ1-40%. Dementia patients with Aβ1-

40%≧60 have on average a distinctly greater severity of the dementia (MMSE 15–16) compared with dementia patients with Aβ1-40%<60 (MMSE 19–20). On the other hand, there is a negative correlation between the severity of Alzheimer's dementia and Aβ1-38%. Dementia patients with Aβ1-38%<17 have on average a distinctly greater severity of the dementia (MMSE 14–15) compared with dementia patients with Aβ1-38%≧17 (MMSE 19–20).

As expected on the basis of the relation (Aβ1-38%⇓ & Aβ1-40%⇑=severity of the dementia⇑) the Aβ1-38/Aβ1-40 ratio is negatively correlated with the severity of the dementia: dementia patients with Aβ1-38/Aβ1-40<0.28 have on average a distinctly greater severity of the dementia (MMSE 14–15) as compared with dementia patients with Aβ1-38/Aβ1-40≧0.28 (MMSE 19–20).

It has emerged on use of the antibody mAb 1E8 that a fraction of the Aβ peptides Aβ1-x and Aβ2-x which depends on the sample pretreatment is accessible for this antibody. It would be possible to maximize the detectable Aβ concentrations by disrupting the Aβ peptides in the samples by treatment with a detergent. An SDS/thermal denaturation has proved suitable for this purpose.

In this connection, it was further possible to establish that a cryopreservation of samples, which takes place before the disruption with a detergent, reduces the concentrations of Aβ peptides which can be determined subsequently even after disruption of the sample with a detergent. The requirement which can be inferred from this is that the samples be subjected to the sample treatment with the detergent even before the cryopreservation and any other low-temperature treatment.

It has additionally emerged that portions of the Aβ peptide Aβ1-42 which are no longer accessible to detection with the antibody mAb 1E8 after a low-temperature treatment, even through disruption of the sample with a detergent, differ in size in patients with and without protein folding diseases. There are evidently different fractions of the Aβ peptide Aβ1-42 in a sample, and these fractions respond differently to low-temperature treatment and disruption with a detergent and, at the same time, vary in their concentrations with the presence of protein folding diseases. The difference in the behavior of these fractions in relation to low temperature indicates cryoprecipitation, so that other precipitation techniques are also possible for distinguishing the two fractions.

Thus, a sample may be divided into at least two part-samples, of which a first part-sample is subjected to the sample treatment with the detergent before or instead of a precipitation treatment, whereas the second part-sample is undertaken before or instead of the sample treatment with detergent. Subsequently, the concentrations of the Aβ peptide Aβ1-42 determined in the two sample parts are compared with one another. The precipitation treatment mentioned may comprise besides a low-temperature treatment also an immunoaffinity method. It is of particular interest to find a difference ΔAβ1-42 between the concentrations of the Aβ peptide Aβ1-42 determined in the two sample parts. This value is a highly significant indicator of the presence of a protein folding disease.

In the practical use of antibody mAb 1E8 it is possible to label the Aβ peptides to which the antibody mAb 1E8 is bound with a secondary antibody directed against the antibody mAb 1E8. The secondary antibody directed against the antibody mAb 1E8 may already be provided with a marker whose quantity can be recorded, or be provided after its immune reaction with the antibody mAb 1E8 with a marker whose quantity can be recorded.

In the recording of the quantity of the marker it is preferred to carry out this recording photometrically with a CCD camera, because this procedure ensures a very high linearity between the signal of the CCD camera and the recorded quantities of the labeled antibody mAb 1E8.

The novel antibody is suitable not only for the diagnostic possibilities described previously but also for the pure concentration of Aβ peptides Aβ1-x and/or Aβ1-x and/or Aβ2-x and/or sAPPα.

A further possibility of use arises in the distinguishing of Aβ peptides Aβ1-x and Aβ2-x from Aβ peptides Aβn-x with n>2, because the antibody mAb 1E8 has a pronounced N-terminal specificity and binds distinctly less (<5%) to Aβ peptides Aβn-x with n>2 when it is employed under the specific conditions of the Aβ SDS-PAGE/immunoblot.

The invention is explained in more detail and described hereinafter by a characterization and a description of a method for producing the antibody mAb 1E8 and in the form of a description of uses of the antibody mAb 1E8.

BRIEF DESCRIPTION OF DRAWINGS

The appended figures show in

| a to d: | mix of synthetic Aβ peptides (dilution series) |
|---|---|
| 5 and 6: | temporal cortex in AD |
| 11 and 12: | temporal cortex in FTD |
| 13 to 15: | temporal cortex in LBD; (13) LBD CERAD A, (14) LBD CERAD C, (15) LBD CERAD C |
| 16: | temporal cortex in NDC |

*The immunoprecipitate in AD was diluted twenty-fold for some patients.

Figure 22:
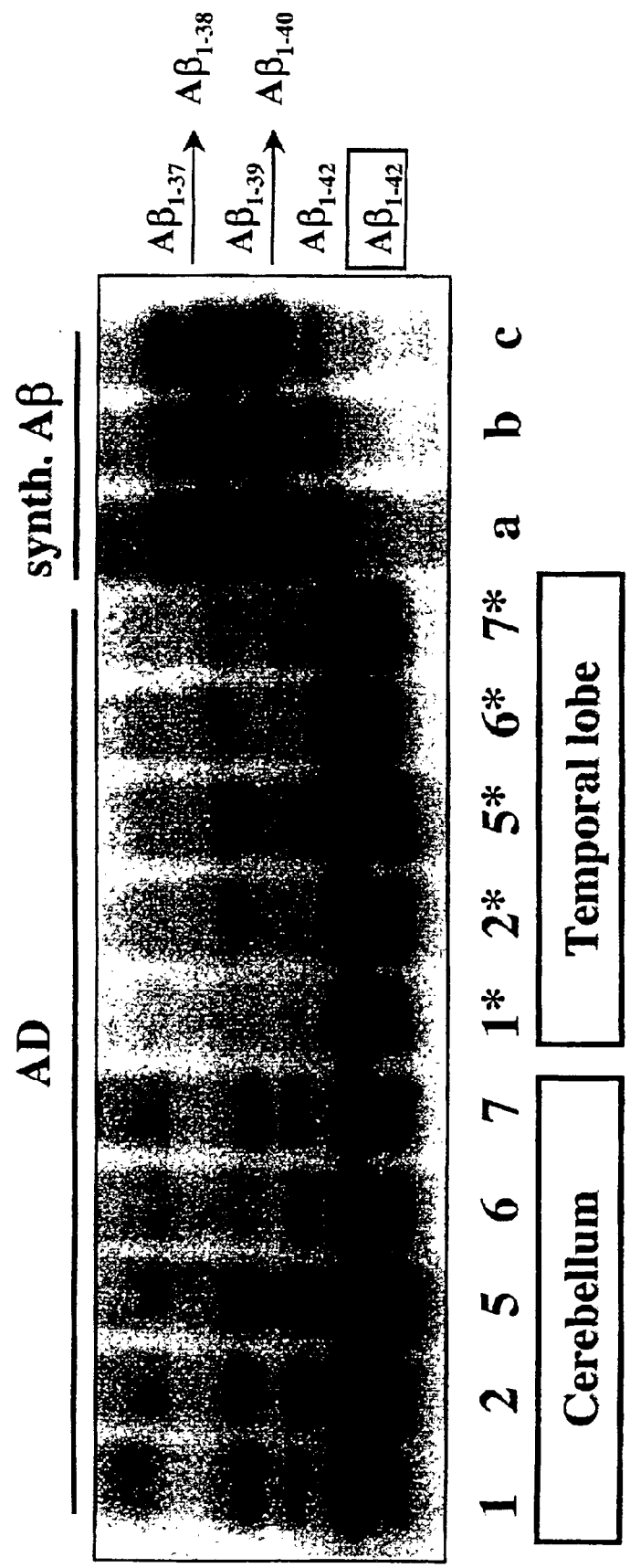

FIG. 22: an Aβ SDS-PAGE/immunoblot 2: immunoprecipitates (mAb 1E8) of RIPA-soluble Aβ peptides in AD from brain homogenates of different regions of the brain. Intraindividual comparison of cerebellum and temporal cortex. Volume applied 4 μl. In columns: a to c: mix of synthetic Aβ peptides (dilution series)

| 1 to 7: | cerebellum |
|---|---|
| 1* to 7*: | temporal cortex, *immunoprecipitates diluted twenty-fold |

Figure 23A:
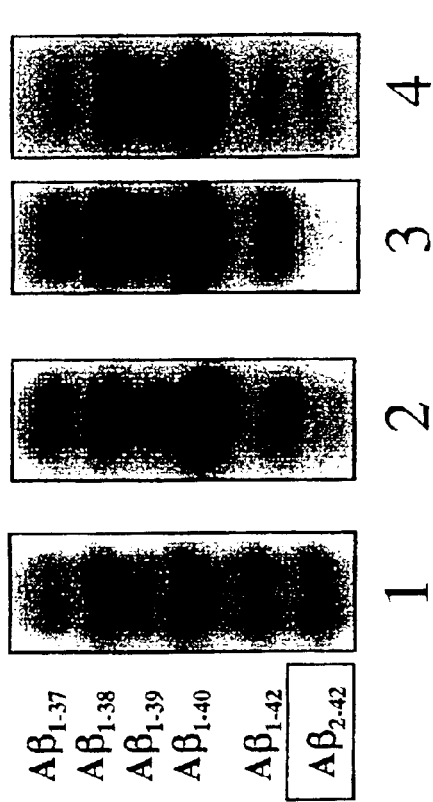

FIG. 23a: an Aβ SDS-PAGE/immunoblot 2, comparing a mix of synthetic Aβ peptides (1) with: (2) SDS/thermally denatured cell culture supernatants of human APP751Sw transgenic H4 neuroglioma cells (volume applied 4 μl), (3) 10 μl of CSF from an NDC patient and (4) 10 μl of CSF from an AD patient.

Figure 23B:
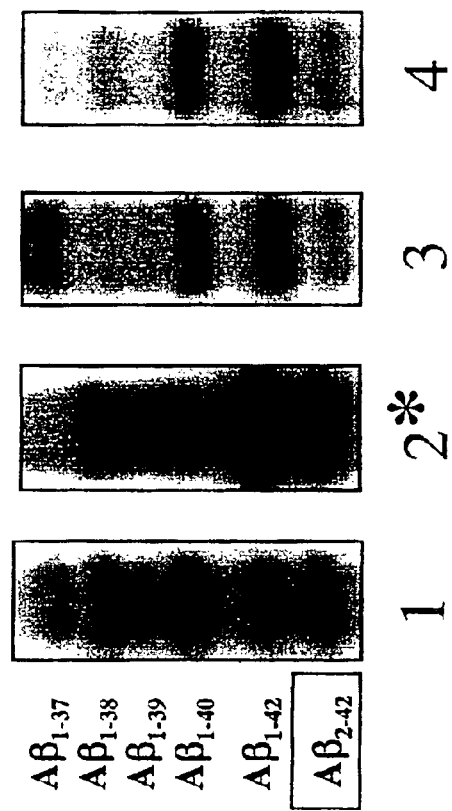

FIG. 23b: an Aβ SDS-PAGE/immunoblot 2 comparing a mix of synthetic Aβ peptides (1) with the immunoprecipitates (mAb 1E8) of RIPA-soluble Aβ peptides in the following brain homogenates:

(2) temporal cortex in AD (3) temporal cortex in frontotemporal dementia (4) temporal cortex, control patient without dementia

*The immunoprecipitate in AD was diluted twenty-fold.

Figure 24:
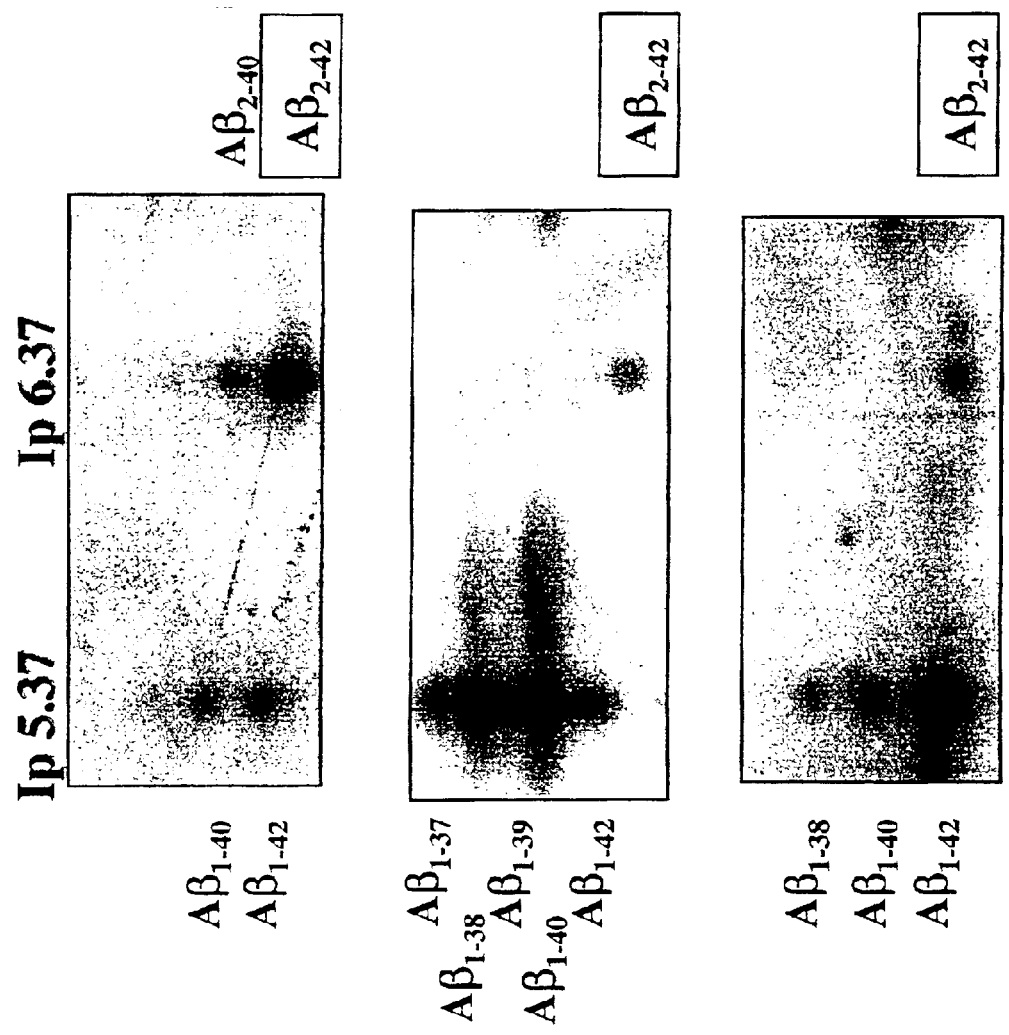

FIG. 24: three Aβ IPG 2D-PAGE/immunoblots 2:

Top: a two-dimensional fractionation of synthetic Aβ peptides. The N-terminal truncation by aspartate makes the isoelectric point (Ip) one pH unit more basic.

Middle: immunoprecipitation (mAb 1E8) and two-dimensional fractionation of CSF from a patient with AD which showed the band with the Rf for Aβ2-42 in the Aβ SDS-PAGE.

Bottom: immunoprecipitation (mAb 1E8) of RIPA-soluble Aβ peptides and two-dimensional fractionation from the temporal cortex in AD. The band with the Rf for A• 2-42 in the Aβ SDS-PAGE is identified as Aβ2-42 in two dimensions also.

Figure 25A:
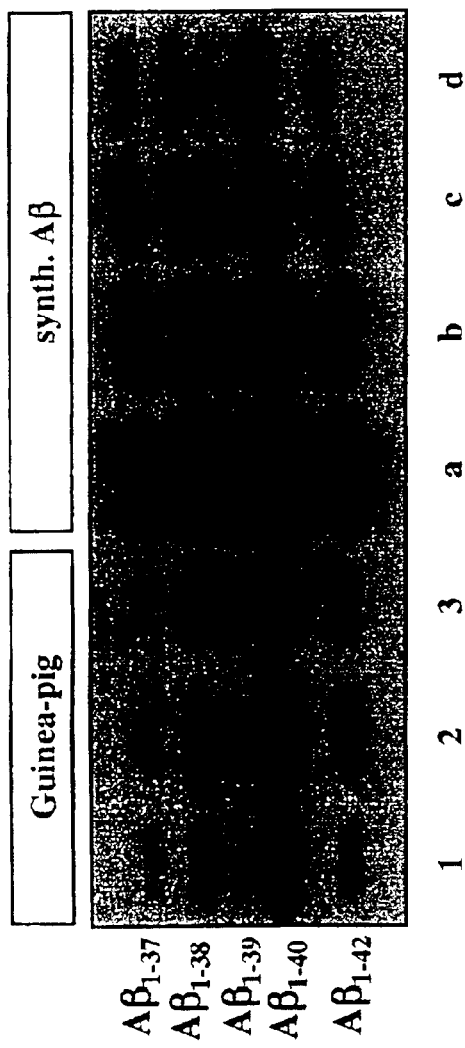
Figure 25:
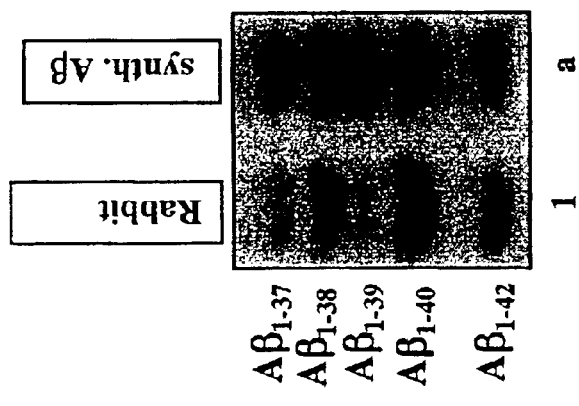

FIG. 25a: an Aβ SDS-AGE/immunoblot 2 of Aβ peptides in the CSF of guinea pigs. The CSF was SDS/thermally denatured before freezing. In columns:

| 1 to 3: | 10 μl of CSF from guinea pigs 1, 2 and 3 |
| a to d: | synthetic Aβ peptides dilution series. |

FIG. 25b: an Aβ SDS-AGE/immunoblot 2 of Aβ peptides in the CSF from a rabbit. The CSF was SDS/thermally denatured before freezing. In columns:

| 1 to 3: | 10 μl of CSF |
| a: | synthetic Aβ peptides. |

Figure 26:
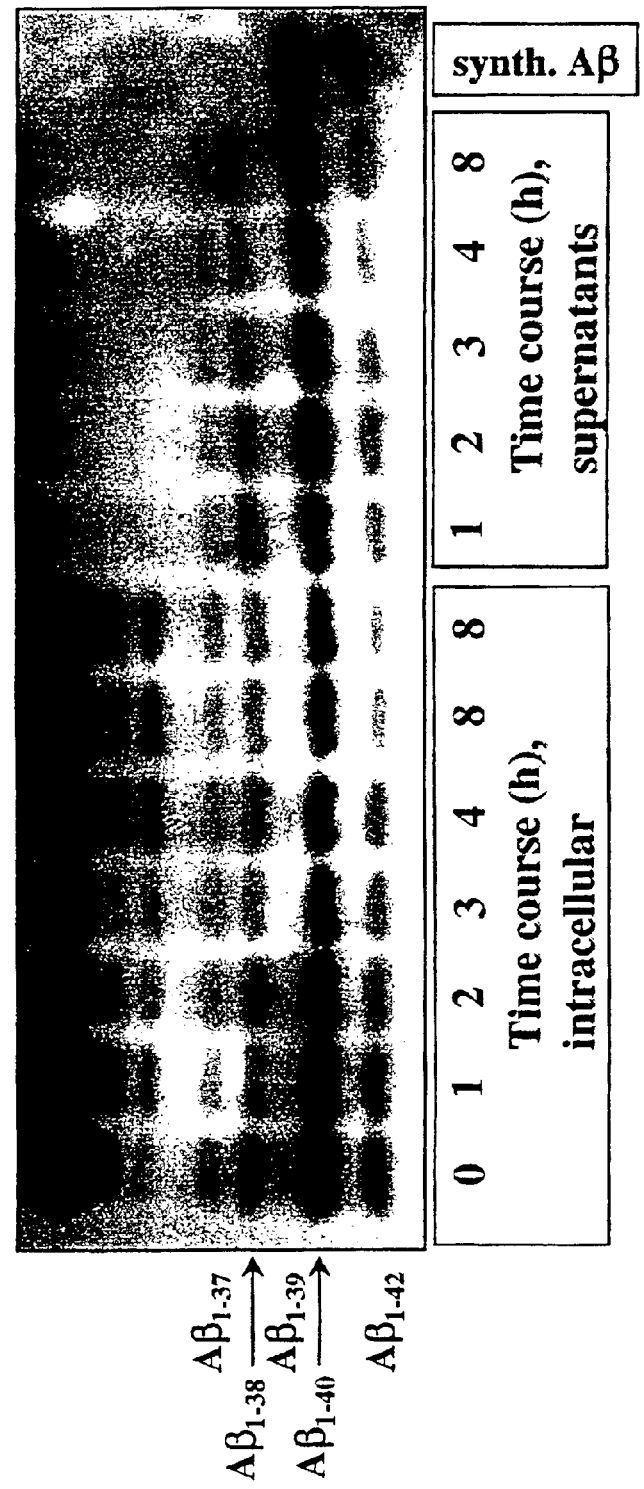

FIG. 26: an Aβ SDS-AGE/immunoblot 2 of hippocampal tissue sections with short-term culture (0–8h) from an adult guinea pig. Two tissue sections (thickness 500 μm) in each case were pooled, homogenized in the presence of RIPA detergents and immunoprecipitated (mAb 1E8). The relevant culture supernatants (2×500 μl) were likewise pooled and immunoprecipitated in the presence of RIPA (mAb 1E8). In columns: 0 to 8, intracellular: time course of the intracellular concentration of Aβ peptides in the hippocampal tissue section immediately after obtaining (0) up to eight hours (8; duplicate measurement) in short-term culture. 1 to 8, supernatants: time course of the Aβ peptides released into the culture supernatants. synth. Aβ: synthetic Aβ1-40 and Aβ1-42

Figure 27:
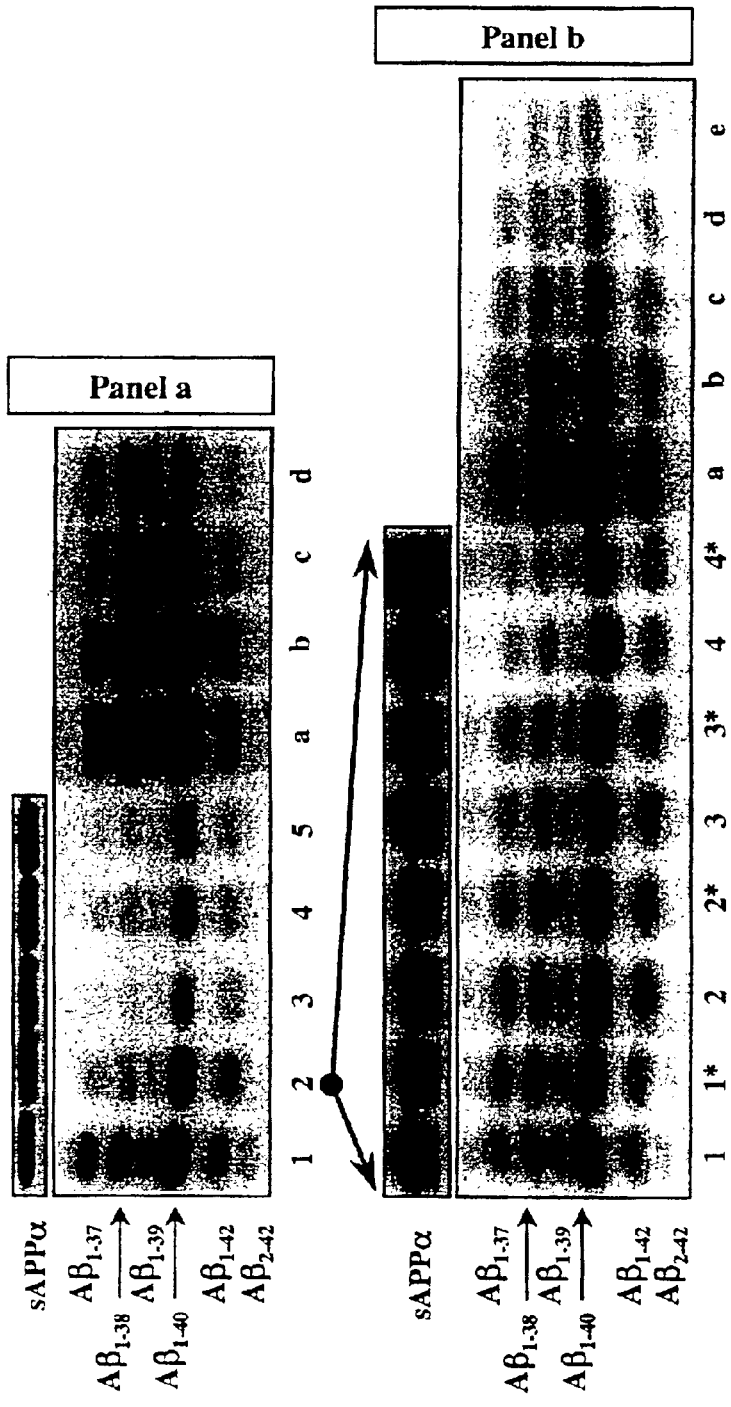

FIG. 27: two Aβ SDS-PAGE/immunoblots 2 which show a treatment of a human 751APPSw trangenic H4 neuroglioma cell line with various protease inhibitors (23a) and a dose-dependent effect of calpain inhibitor 1 (23b). The released Aβ peptides were quantified in 4 μl of SDS/thermally denatured cell culture supernatants in each case (cf. FIGS. 23a,b). For comparison, the sAPPα concentration in the cell culture supernatants was determined.

In panel a: (1) is DMSO control; (2) is 50 μM calpain inhibitor 1; (3) is 100 μM calpain inhibitor 3; (4) is 5 μM MG132; (5) is 25 μM calpeptin; (a–d) is mix of synthetic Aβ peptides.

Figure 28A:
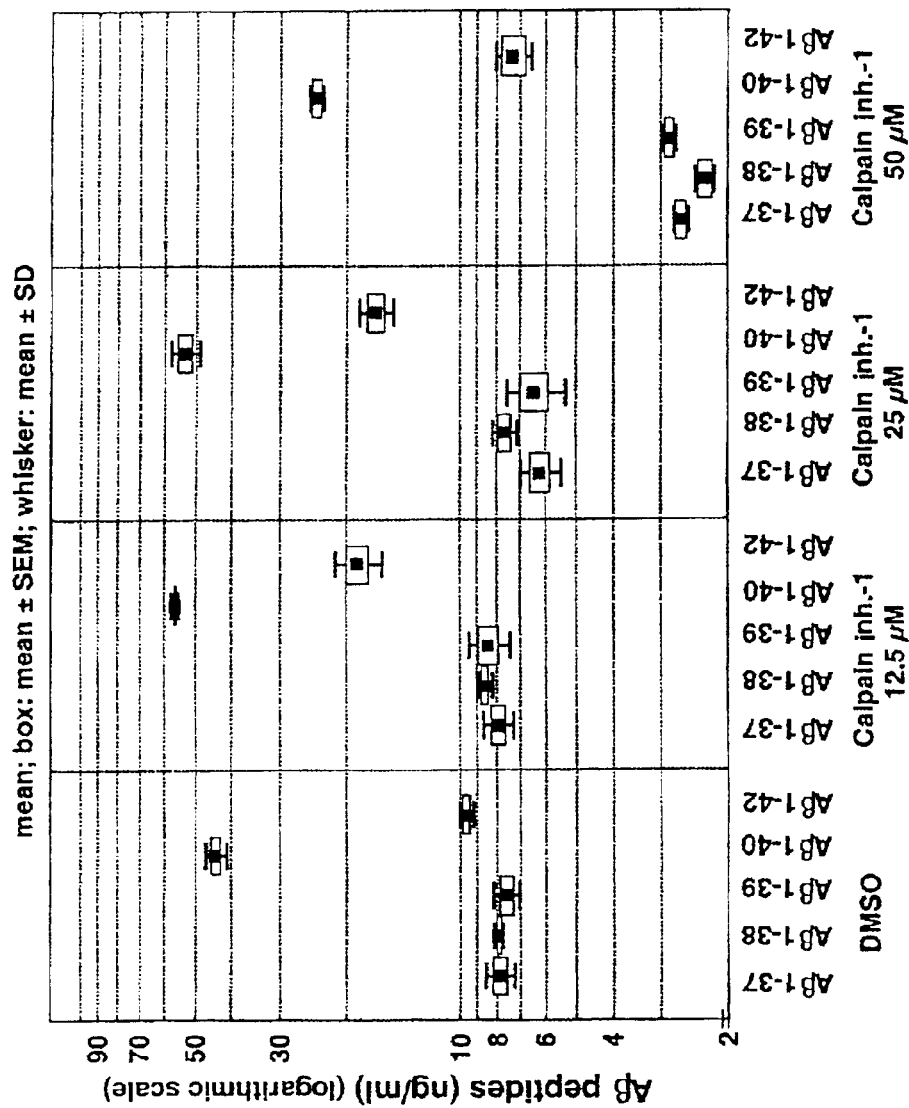

FIG. 28a: an Aβ SDS-PAGE/immunoblot 2, which shows a treatment of a human APP751Sw trangenic H4 neuroglioma cell line with various concentrations of calpain inhibitor 1 (cf. FIG. 23b). The released Aβ peptides were quantified in 4 μl of SDS/thermally denatured cell culture supernatants in each case. The dose-dependent effect of calpain inhibitor 1 on the Aβ peptide concentration in the supernatant was investigated, comparing with the DMSO control.

Figure 28B:
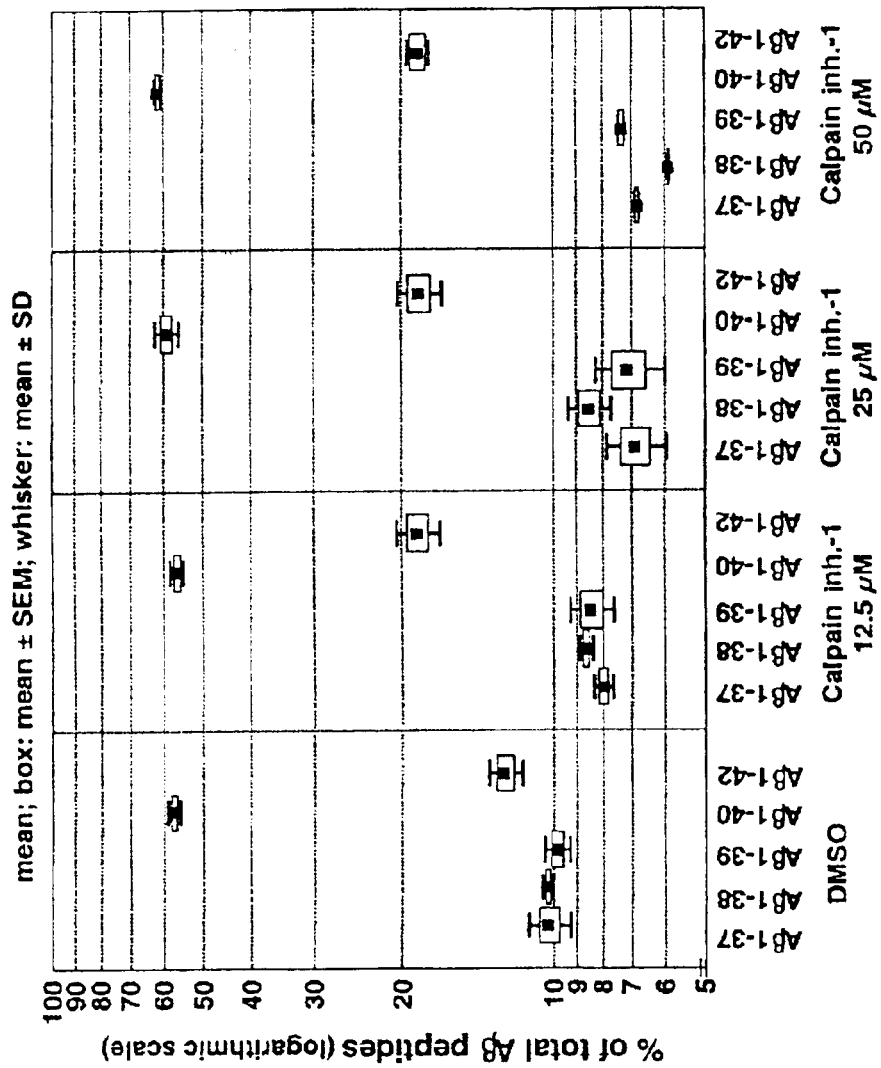

FIG. 28b: an Aβ SDS-PAGE/immunoblot 2, which shows a treatment of a human APP751Sw trangenic H4 neuroglioma cell line with various concentrations of calpain inhibitor 1 (cf. FIG. 23b). The released Aβ peptides were quantified in 4 μl of SDS/thermally denatured cell culture supernatants in each case. The dose-dependent effect of calpain inhibitor 1 on the proportion of an Aβ peptide species as a percentage of the total Aβ peptide concentration was investigated, comparing with the DMSO control.

21 tables are additionally appended.

DETAILED DESCRIPTION

0 Production of the Monoclonal Anti Aβ Antibody 1E8

The monoclonal antibody mAb 1E8 was produced under contract with Schering A G by the contracting company "nano Tools Antiköpertechnik" in Denzlingen by the standard methods thereof. The immunization and screening strategy was designed in consultation with Schering A G.

Brief description: the complete Aβ Protein (1-42) was employed for immunizing Balbic mice (10 μg/immunization). A primary immunization was followed by 3 booster immunizations. The immunizations took place at intervals of 2 weeks in each case. The animal was then sacrificed and the spleen was employed for cell fusion with a mouse myeloma cell line. The fused cells were transferred to 96-well tissue culture plates and cultivated in the presence of feeder macrophages.

To identify the N-terminally specific antibodies, the peptide 1-16 was covalently coupled to appropriately activated ELISA plates and employed for the screening with the hybridoma cell supernatants. The Aβ 1-16-positive clones were then recloned and tested again. Expansion of the clones was followed by cryopreservation. Concentration of the antibody was carried out by ion exchange chromatography under non-denaturing conditions.

For delimitation of the specificity of the antibody, an epitope mapping was undertaken from cellulose-bound linear peptides (spot synthesis). For this purpose, the primary sequence of Aβ was synthesized as a series of overlapping peptides in the form of spots on a cellulose membrane, and the membrane was incubated using monoclonal antibodies in analogy to the Western blot method. The detection of specifically bound antibodies took place with a secondary antibody.

The analysis revealed that the antibody 1E8 belonging to the IgG1 kappa subclass detects an N-terminal linear epitope which is formed from the first 8 N-terminal amino acids of the Aβ sequence. This antibody proved in subsequent experiments as suitable for the detection of native Aβ in Western bot, immunoprecipitation, immunohistochemistry and ELISA.

1 Overview 1.1 Description of the Methods

A sodium lauryl sulfate polyacrylamide gel electrophoresis (SDS-PAGE) for the fractionation of the β-amyloid precursor protein (APP) and its metabolites, in particular the β-amyloid peptides (Aβ peptides), is described. The specific SDS-PAGE, called Aβ SDS-PAGE hereinafter, uses a multiphase buffer system (bicine/bistris/tris/sulfate), and the separation mechanism is based on a urea-induced conformational change of Aβ peptides on entry into the resolving gel compartment. The conformational change is highly specific for the amino acid primary sequence of the respective Aβ peptides and leads to a reproducible change in the effective molecular radius. It is thus possible to fractionate a large number of Aβ peptides which differ at the N and C termini in some cases by only one amino acid and cannot be fractionated by conventional SDS-PAGE because of the small mass difference. The conformational change is induced under the conditions of the multiphase buffer system by addition of urea above a concentration 6M. The Aβ peptide-specific conformational change is determined at a defined pH and ionic strength not only by the molarity of the urea employed but also by the pore size of the polyacrylamide gel, the concentration of the detergent (SDS) and the temperature during the separation. The optimal resolving gel matrix for the fractionation of a wide range of N- and C-terminally (Nt, Ct) modified Aβ peptides was found with 12% T/5% C/8M urea/0.25% SDS.

The Aβ SDS-PAGE was combined with the isoelectric focussing (IEF) within a first analytical dimension using carrier ampholytes or immobilized pH gradients (IPG) for the two-dimensional electrophoresis (Aβ 2D-PAGE and Aβ IPG 2D-PAGE). Aβ SDS-PAGE and Aβ IPG 2D-PAGE were used to characterize the electrophoretic migration behavior of the synthetic Aβ peptides $A\beta_{1-33}$, $A\beta_{1-34}$, $A\beta_{1-35}$, $A\beta_{1-37}$, $A\beta_{1-38}$, $A\beta_{1-39}$, $A\beta_{1-40}$, $A\beta_{1-42}$, $A\beta_{2-40}$, $A\beta_{3-40}$, $A\beta_{3p-40}$, $A\beta_{2-42}$, $A\beta_{3-42}$ and $A\beta_{3-42}$.

Detection took place by means of Western immunoblot (PVDF membrane) and enhanced chemiluminescence (ECL) (Aβ SDS-PAGE/immunoblot, Aβ 2D-PAGE/immunoblot, Aβ IPG 2D-PAGE/immunoblot). For this purpose, the monoclonal antibody mAb 1E8 for which an unusually high N-terminal specificity was detected was employed. Under the conditions of the Western immunoblot employed, the mAb 1E8 recognizes in the absence of the N-terminal aspartate the corresponding Aβ peptides 2-x (e.g. $A\beta_{2-40}$, $A\beta_{2-42}$) with a similarly good detection sensitivity as the Aβ peptides 1-x (e.g. $A\beta_{1-40}$, $A\beta_{1-42}$). The synthetic Aβ peptides $A\beta_{3-40}$ or $A\beta_{3-42}$, in which the amino acid alanine at the N terminus is additionally absent, and their pyroglutamate derivatives are by contrast no longer detected in physiologically relevant concentrations. It was possible to improve the detection sensitivity in the Western immunoblot selectively for the mAb 1E8 by employing, in place of the milk powder which is otherwise mainly used (immunoblot 1), a synthetic reagent for blocking nonspecific binding sites (immunoblot 2). A commercially available N-terminally specific monoclonal antibody (6E10), which is otherwise frequently employed for detecting Aβ peptides by Western-immunoblot, is not compatible with immunoblot 2. It was possible by combining Aβ SDS-PAGE/immunoblot 2 with the detection of the APP metabolites via a highly sensitive CCD camara to construct a quantitative Western immunoblot with a detection sensitivity of 1 pg for $A\beta_{1-40}$ and 2 pg for $A\beta_{1-42}$. It is possible to achieve intra- and interassay coefficients of variation of less than 10% for 20 pg of Aβ peptide for the Aβ SDS-PAGE/immunoblot 2 with CCD detection. The detection sensitivity for the Aβ SDS-PAGE/immunoblot 2 with film detection is 0.3 pg for $A\beta_{1-40}$ and 0.6 pg for $A\beta_{1-42}$. No other Western immunoblot methods with equally good detection sensitivity and coefficients of variation for detecting Aβ peptides have been disclosed to date. The abovementioned detection sensitivity is a precondition for neurochemical dementia diagnosis in the CSF if the Aβ peptides are to be quantified directly after SDS/thermal denaturation by Western immunoblot and CCD camera, i.e. without previous selective concentration by immunoprecipitation. It was possible to demonstrate further that the separation efficiency of the Aβ SDS-PAGE/immunoblot for neurochemical dementia diagnosis can be considerably increased further precisely by this sample pretreatment when the SDS/thermal denaturation takes place before the CSF samples are frozen 1.2 Aβ SDS-PAGE/Immunoblot and Neurochemical Dementia Diagnosis The Aβ SDS-PAGE/immunoblot 2 (see above) achieves for the first time direct quantification of sAPPα and Aβ peptides by means of a CCD cameral in only 10 μl of human or animal (guinea pig, rabbit) CSF samples. It was possible with this method to demonstrate for the first time that, besides $A\beta_{1-40}$ and $A\beta_{1-42}$, three other Aβ peptides with carboxyterminal (C-terminal) truncation ($A\beta_{1-37}$, $A\beta_{1-38}$, $A\beta_{1-39}$) occur in a highly conserved manner in human and animal CSF. Moreover the second commonest Aβ peptide after $A\beta_{1-40}$ in human CSF is not as previously assumed $A\beta_{1-42}$ but $A\beta_{1-38}$. It was further possible to show that the three additional Aβ peptides with C-terminal truncation are also detectable in human plasma, but with a considerably lower concentration and a different mode of distribution there. In particular, the $A\beta_{1-42}/A\beta_{1-38}$ ratio appears to differ in a CNS-specific manner.

In some patients with AD the N-terminally truncated Aβ peptide 2-42 is additionally detectable in the CSF, that is ordinarily extensively increased in brain homogenates from patients with AD.

It was possible to demonstrate for the first time that, in contrast to the absolute concentrations of the Aβ peptides in the CSF, the proportions Aβ1-n % of the Aβ peptides Aβ1-n, with n=37, 38, 39, 40 or 42, as a percentage of their total amount of Aβ1-x identify patients with AD and chronic inflammatory CNS disorders (CID) with high sensitivity and specificity. In contrast to the absolute concentrations, the relative proportions of Aβ peptides also correlate significantly with the severity of the dementia. It was further possible to show specific associations between certain percentage Aβ peptide proportions for patients with AD. This also applies to certain Aβ peptide ratios and the corresponding correlations can be used for improved neurochemical dementia diagnosis. In particular the association between $A\beta_{1-38}\%$ and $A\beta_{1-42}\%$, or the correlation between the Aβ peptide ratios $A\beta_{1-38}/A\beta_{1-40}$ and $A\beta_{1-42}/A\beta_{1-38}$, shows a comparatively high correlation in AD and is very diagnostically promising. The surprisingly marked difference between the absolute and proportionate concentrations of the Aβ peptide species in relation to their suitability for neurochemical dementia diagnosis is probably caused by the occurrence of disease-specific changes in the γ-secretase activity and these are described better by the change in the relative Aβ peptide proportions.

To prepare samples for the Aβ SDS-PAGE/immunoblot, Aβ peptides and other APP metabolites undergo SDS/thermal denaturation. An alternative possibility is to carry out an immunoprecipitation (IP) beforehand for selective concentration of Aβ peptides. The results show that different proportions of the Aβ peptides occurring in biological fluids can be measured depending on the sample preparation. It is possible in this connection to distinguish a proportion which can be dissociated with detergent (SDS) from an Aβ peptide fraction which is directly accessible to antibodies in immunoprecipitation or ELISA methods, i.e. without simultaneous treatment with detergents. This differentiation is probably explained by high-affinity binding of the Aβ peptides to other proteins or Aβ autoaggregates. The proportion which can be dissociated with SDS is moreover distinctly higher than the fraction which can be dissociated with antibodies. This phenomenon is particularly pronounced specifically for $A\beta_{1-42}$.

A reduction caused by cryoprecipitation (CP) through the freezing of the CSF samples is detectable for $A\beta_{1-42}$—in contrast to $A\beta_{1-40}$. The reduction caused by CP is probably borne mainly by the aggregate-bound fraction of $A\beta_{1-42}$ and, in a considerable proportion of patients without Alzheimer dementia (NDC), leads to an AD-typical reduction in the level of $A\beta_{1-42}$ in the CSF. This effect is particularly marked in patients with at least one ApoE ε4 allele and probably explains why comparatively low $A\beta_{1-42}$ concentrations are measured in previously frozen CSF even for patients without AD but with ε4 allele.

It is possible by "protective" SDS/thermal denaturation before the freezing of the sample to prevent effectively the reduction caused by CP in $A\beta_{1-42}$ in patients without AD. By contrast, patients with AD show low $A\beta_{1-42}$ concentrations in CSF even if the CSF sample is pretreated with SDS/thermal denaturation before the freezing. This means that the diagnostic separation efficiency of the Aβ SDS-PAGE/immunoblot for neurochemical dementia diagnosis is very considerably improved by SDS/thermal denaturation of the CSF samples before the freezing process. The Aβ SDS- PAGE/immunoblot in conjunction with the abovementioned sample preparation is also very promising for early and preclinical diagnosis of AD because it is to be expected that marginally low $A\beta_{1-42}$ CSF levels indicate incipient AD in particular when they cannot be explained by a CP-dependent reduction. Alternatively, it should be checked by prospective studies on patients with mild cognitive disorders whether a pronounced CP-dependent reduction of $A\beta_{1-42}$ does not per se have predictive value for later development of AD.

The CP-dependent reduction in $A\beta_{1-42}$ in the CSF in AD can be explained by the following theories:

1. the CSF of patients with AD contains selectively less $A\beta_{1-42}$ while the total $A\beta$ peptide concentration is unchanged
2. the CP-related reduction in $A\beta_{1-42}$ cannot be prevented despite SDS/thermal denaturation
3. $A\beta_{1-42}$ is not reduced in the CSF in AD but is only measurable to a diminished extent due to SDS-stable binding to carrier proteins or $A\beta$ peptide aggregates In the latter case (3), this fraction of $A\beta_{1-42}$ would also escape enzymatic catabolism and thus be pathophysiologically relevant and potentially a molecular target for projects to find active ingredients. In this connection it is not absolutely necessary that the composition or the molecular primary structure of $A\beta_{1-42}$-binding proteins within the complex to be changed; on the contrary, the affinity of the binding might vary depending on the conformation of $A\beta_{1-42}$, while the primary structure is the same.

The finding that a specific difference becomes detectable in the fraction which can be dissociated by detergent of $A\beta_{1-42}$ in the CSF of patients with and without AD can also be utilized for other methods of neurochemical dementia diagnosis (ELISA, fluorescence correlation spectroscopy).

Particularly promising is the use of the ELISA triplet $A\beta_{1-38}$, $A\beta_{1-40}$ and $A\beta_{1-42}$ with calculation of the $A\beta$ peptide ratios (38/40, 42/38, 42/40) and determination of the CP-dependent reduction in the $A\beta$ peptides through differential sample pretreatment.

1.3 $A\beta$ SDS-PAGE/Immunoblot and Neuropathological Diagnosis

The $A\beta$ SDS-PAGE/immunoblot can be employed for post mortem neuropathological diagnosis of dementing disorders. On analysis of the detergent (RIPA)-soluble fraction of $A\beta$ peptides in brain homogenates from patients with AD, other dementing disorders and controls it is possible to show disease- and brain region-specific expression patterns of the $A\beta$ peptides 1-37, 1-38, 1-40, 1-42 and 2-42. Particularly noteworthy is the massive increase in $A\beta_{2-42}$ in the RIPA-soluble fraction of brain homogenates in AD and patients with Lewy body dementia (LBD). These high concentrations of $A\beta_{2-42}$ are observed in LBD when the patients simultaneously show a pronounced $\beta$-amyloid pathology (LBD, CERAD C). $A\beta_{1-42}$ is also regularly and distinctly increased in AD and LBD (CERAD C). The concentration of the other $A\beta$ peptides showed a great interindividual variation. This might be evidence of phenotypical subtypes of sporadic AD or indicate the severity of the dementia as a function of the progression.

The RIPA detergent mix used herein is not able to solubilize mature neuritic $\beta$-amyloid plaques. The great increase in the concentrations of $A\beta_{2-42}$ therefore cannot be explained by $A\beta_{2-42}$ from this $\beta$-amyloid plaque fraction. Correspondingly, it is also unlikely that $A\beta_{2-42}$ is produced mainly by nonspecific $\beta$-amyloid plaque-associated post-translational modifications. The high intracerebral concentrations of $A\beta_{1-42}$ are pathophysiologically relevant because the absence of aspartate increases the tendency of $A\beta_{1-42}$ to aggregate and this N-terminal modification apparently precedes the formation of mature $\beta$-amyloid plaques.

1.4 Quantification of APP Metabolites by $A\beta$ SDS-PAGE/Immunoblot in Cell Culture and Animal Models The carboy-terminally truncated $A\beta$ peptides 1-37, 1-38 and 1-39 were also frequently detectable in the cisternal fluid of guinea pigs and rabbits. Detection was also possible in homogenates and supernatants (short-term culture) of hippocampal tissue sections from the adult guinea pig.

It has also been possible to establish a novel neuronal (telencephalic) chick primary culture and show that the AP peptide quintet is released into the supernatants here too with a relative distribution comparable to that in human CSF.

The $A\beta$ peptide quintet—and additionally $A\beta_{2-42}$ —can also be detected in the supernatants of a neuroglioma tumor cell line (H4) which overexpresses human APP751 with the Swedish double mutation ($_{human}$APP751$_{Sw}$). After treatment of the cells with protease inhibitors which are potential inhibitors of $\beta/\gamma$ secretases, it was possible to detect not only the known dose-dependent reduction of $A\beta_{1-40}$ and $A\beta_{1-42}$ but also a reduction in the C-terminally truncated $A\beta$ peptides 1-37, 1-38, and 1-39. In addition, the formation of $A\beta_{2-42}$ was inhibited. It was of interest in this connection that the production of the Ct-truncated $A\beta$ peptides were— particularly clearly for $A\beta_{1-37}$ —inhibited with different kinetics and earlier compared with $A\beta_{1-40}$ and $A\beta_{1-42}$. This effect became particularly clear on examination of the proportions of the individual $A\beta$ peptide species in the total concentration thereof. An interesting analogy emerges here with the disease-specific changes, discussed above, in the $A\beta$ peptides in the CSF, which were also measurable considerably more sensitively via the percentage proportions of peptides in the CSF. It can accordingly be assumed that a heterogeneity of the $\gamma$-secretase activity may be reflected by changes in the relative composition of the $A\beta$ peptide quintet. This is relevant for projects for finding active ingredients for identifying isoform-specific $\gamma$-secretase inhibitors.

On treatment of the transgenic H4 neuroglioma cell culture with calpain inhibitor 1 it was possible to demonstrate the previously described initial (paradoxical) increase in the $A\beta_{1-42}$ concentration at a low concentration of the protease inhibitor. It is of interest in this connection that the increase in $A\beta_{1-42}$ did not correlate with an increase the $A\beta_{2-42}$ concentration. This finding is against there being secondary production of $A\beta_{2-42}$ from $A\beta_{1-42}$ and in favor of the theory that $A\beta_{2-42}$ is produced by a combined $\beta/\gamma$-secretase cut. The question arising in connection with the markedly and regularly increased concentration of $A\beta_{2-42}$ in brain homogenates in AD and the detection of $A\beta_{2-42}$ in CSF samples from patients with AD is whether a particular isoform of $\beta$-secretase (BACE) is overexpressed in AD or the physiologically produced $A\beta_{2-42}$ is catabolized less in AD.

2. Background of the Methodology of the Techniques Used in the Examples

The molecular basis of AD, their relation to recent medical approaches to dementing disorder and methods of neurochemical dementia diagnosis are summarized in two review articles (Witfang et al., 1998 and 2000).

Another SDS-PAGE/immunoblot method has previously been described for analyzing $A\beta_{1-40}$ and $A\beta_{1-42}$/1-43 in human lumbar CSF (Ida et al., 1996). However, differentiation of the $A\beta$ peptides is not possible in this case by electrophoretic separation but takes place on the blot membrane through C-terminally selective monoclonal antibodies. At the same time, $A\beta_{1-42}$ must be concentrated before the separation by concentrating the sample. The concentration takes place without previous SDS denaturation, which appears to make the method problematic due to the great tendency of $A\beta_{1-42}$ to aggregate. Separate electrophoresis must be carried out for determining $A\beta_{1-40}$ and 1-42 in this method.

The multiphase buffer system employed for the $A\beta$ SDS-PAGE/immunoblot (Wiltfang et al., 1991), combines the advantages of specific buffer systems for proteins (Laemmli, 1970) and peptides (Schagger and von Jagow, 1987). It is accordingly possible with this SDS-PAGE method to fractionate with high resolution both proteins and peptides in a homogeneous polyacrylamide resolving gel system. In addition, the electrophoretic separation of $A\beta_{1-40}$ and $A\beta_{1-42}$ have been described (Klafki et al., 1996) using the urea version (Wiltfang et al., 1991) of the latter SDS-PAGE method. Application of this method to cell culture models of familial AD which have been pretreated with inhibitors of APP-cleaving enzymes (γ-secretase) showed through detection of the in vivo radiolabeled $A\beta$ peptides 1-40 and 1-42 that different γ-secretases are involved in the enzymatic production of $A\beta_{1-42}$ (Klafki et al., 1996). It was possible with a modification of this system also to achieve separation between $A\beta_{1-42}$ and $A\beta_{1-43}$ (Wiltfang et al., 1997). The maximum immunological detection sensitivity of the latter method was 50 pg of $A\beta_{1-42}$, which is far from adequate for the applications shown herein. At the same time, the resolving gel matrix has been optimized in the method presented here in order to fractionate additional N-terminally and C-terminally modified $A\beta$ peptides.

The SDS-PAGE can be combined as second analytical dimension with isoelectric focussing (IEF) in the first dimension as 2D-PAGE (O'Farrell, 1975; O'Farrell et al., 1977). This achieves a two-dimensional fractionation of polypeptides and proteins according to the isoelectric point and effective molecular radius. Isoelectric focussing is able to reveal minimal differences in charge on use of wide-span immobilized pH gradients (Gorg et al., 1995; Gorg et al., 1997; Righetti and Bossi, 1997). The two-dimensional $A\beta$ SDS-PAGE/immunoblot can therefore also be employed for high-resolution analysis of post-translational modifications of APP metabolites. It is possible at the same time to achieve a detection sensitivity in the upper femtogram region. Post-translational modifications may influence in a specific manner the aggregation behavior of $A\beta$ peptides and are thus of pathophysiological and diagnostic relevance (Thome et al., 1996; Thome J., 1996; Kuo et al., 1997; Russo et al., 1997; Tamaoka et al., 1997). Of relevance to neurochemical dementia diagnosis is the fact there is a selective increase in the proportion of N-terminally modified $A\beta_{X-42/43}$ to $A\beta_{1-42/43}$, but not in the proportion of N-terminally modified $A\beta_{X-40}$ to $A\beta 1-40$ (Tamaoka et al., 1997). In addition to determining the $A\beta$ peptides, the $A\beta$ SDS-PAGE/immunoblot also allows quantification of sAPPα, that is measured low in the CSF in AD (Sennvik et al., 2000). To determine sAPPα, the urea-containing resolving gel compartment is combined with an upper (cathodic) resolving gel without urea and larger pore size.

The quantitative $A\beta$ SDS-PAGE/immunoblot allows simultaneous and ultrasensitive determination of a range of APP metabolites which have great relevance for the neurochemical early diagnosis and pathogenesis of AD. The method can also be employed in the animal experimental and clinical evaluation of novel drugs which intervene in the metabolism or catabolosim of $A\beta$ peptides.

3 Materials and Methods
3.1 $A\beta$ SDS-PAGE
3.1.1 Material and Reagents

Bio-RAD (Richmond, Calif., USA): Mini Protean II electrophoresis system, acrylamide (order No. 161-0101), N,N'-methylenebisacrylamide (order No. 161-0201); Merck (Darmstadt, Germany): ammonium peroxodisulfate (AMPS, order No. 1201.1000), bromophenol blue (order No. 8122), 0.5 M $H_2SO_4$ (order No. 1.09072.1000), sodium hydroxide pellets analytical grade (NaOH, order No. 6498), activated carbon analytical grade (order No. 1.02186.0250), sucrose (order No. 1.07654.1000)

Paesel+Lorei (Hanau, Germany): Tris ultra pure (order No. 100840)

Biomol (Hamburg, Germany): sodium lauryl sulfate, ultra pure, 2×cryst. (SDS, order No. 51430), bis(2-hydroxyethyl)iminotris(hydroxymethyl)methane (Bis-Tris, order No. 50003), N,N'-bis(2-hydroxyethyl)glycine analytical grade (bicine, order No. 01848); GibcoBRL/Life Technologies (Karlsruhe, Germany): urea (order No. 15716-012);

Serva (Heidelberg, Germany): N,N,N',N'-tetramethylethylenediamine (TEMED, order No. 35925); Sigma (Steinheim, Germany): 2-mercaptoethanol (order No. M-7154); Bachem (Bubendorf, Switzerland): $A\beta_{1-38}$, $A\beta_{1-40}$, $A\beta_{1-42}$ Forschungsinstitut für Molekulare Pharmakologie (Berlin, Germany): $A\beta_{1-33}$, $A\beta_{1-34}$, $A\beta_{1-35}$, $A\beta_{1-37}$, $A\beta_{1-39}$, $A\beta_{2-40}$, $A\beta_{2-42}$, $A\beta_{3-40}$, $A\beta_{3-42}$, $A\beta_{3p-40}$, $A\beta_{3-42}$ Amersham Pharmacia Biotech AB (Buckinghamshire, England) and Serva (Heidelberg, Germany): trypsin inhibitor bovine lung ($M_r$ 6500), mellitin ($M_r$ 2847) and met-lys-bradykinin ($M_r$ 1320) were purchased from Serva and added to the low-molecular-weight (LMW) marker kit from Amersham Pharmacia. The LMW kit is composed of: phosphorylase b ($M_r$ 94000), bovine serum albumin ($M_r$ 67000), ovalbumin ($M_r$ 43000), carbonic anhydrase ($M_r$ 30000), trypsin inhibitor, soybean ($M_r$ 20100) and α-lactalbumin ($M_r$ 14400).

3.1.2 Gel Composition and Electrophoresis

The SDS-PAGE was carried out using the Bio-Rad mini protean II electrophoresis system. The size of the gel compartment used was as follows: resolving gel length about 54 mm; stacking gel length about 5 mm (corresponding to a volume of 250 μl); comb gel height about 12–15 mm; gel thickness 0.50 mm in each case, gel width 85 mm in each case. Resolving and stacking gels for the second analytical dimension in the $A\beta$ 2D-PAGE have a gel thickness of 1.0 mm.

For sample loading, a 15-tooth sample loading column is used (width of teeth about 3 mm, distance between teeth 2 mm). The resulting sample loading well in the comb gel measures about 3×10 mm. The max. amount of sample loaded should not exceed 10 μl in order to be certain of preventing carry-over between the sample wells. The samples are introduced as layer underneath after introduction of the cathode buffer. Electrophoresis: a) 12 mA/0.5 mm of gel thickness with constant current strength over 2 h, b) 1.0 mm gels of the second analytical dimension: 60 volt/1.0 mm gel thickness for 10 min, 120 volt/1.0 mm gel thickness over 1 h 45 min.

The urea version of the bicine/tris SDS-PAGE method of Wiltfang et al. (Wiltfang et al., 1991) was used for the resolving gel compartment and was modified in essential aspects for the presented applications. Table 1 summarizes the concentrated buffers for the gel compartment, cathode buffer, anode buffer and the acrylamide stock solution. The gel composition for the $A\beta$ SDS-PAGE for optimized separation of APP metabolites and Aβ peptides in human or animal biological samples is to be found in table 2.

3.1.3 Sample Preparation for Aβ SDS-PAGE 3.1.3.1 Taking up of CSF Samples

300 μl aliquots of SDS-SB-3 without 2-mercaptoethanol (table 3) are concentrated to the dry substance in 1.5 ml Eppendorf sample vessels ("safe lock") using a Speed-Vac and stored at room temperature until used. The CSF samples are divided into aliquots and processed differently using the SDS-SB-3 which is introduced into the Eppendorf vessels as dry substance:

(a) CSF Frozen Untreated

330 μl of centrifuged CSF is frozen untreated, and stored, in 1.5 ml Eppendorf vessels at −80° C. After thawing and a vortex step, the introduced SDS-SB-3 is taken up with 300 μl of CSF and 2.5% v/v 2-mercaptoethanol and, after a vortex step, heated at 95° C. for 5 min. The Aβ SDSPAGE then takes place.

(b) Pretreatment by SDS/Thermal Denaturation

The SDS-SB-3 which is introduced as dry substance is taken up with 300 μl of centrifuged CSF and, after a vortex step, heated at 95° C. for 5 min (no addition of 2-mercaptoethanol). The SDS/thermally denatured CSF is then stored at −80° C. The Aβ SDS-PAGE is preceded by addition of 2.5% v/v 2-mercaptoethanol to the sample and heating at 95° C. for 5 min.

(c) Concentration of CSF Samples for Determination of Aβ Peptides

After SDS/thermal denaturation, but before addition of 2-mercaptoethanol, the CSF sample, or else other biological samples, can be concentrated to the dry substance using a SpeedVac and taken up with 100 μl of $H_2O_{dd}$ and 2.5% v/v 2-mercaptoethanol (3-fold concentration). Aβ SDS-PAGE is again preceded by heating at 95° C. for 5 min.

The SDS/thermal denaturation before concentration of the sample is intended to avoid proteolysis, precipitation and autoaggregation of the Aβ peptides during the concentration.

The reduced SDS concentration in SDS-SB-3 is necessary because higher SDS concentrations lead, after three-fold concentration of the samples and with a loading volume of about 10 μl, to an impaired migration behavior of the Aβ peptides at the anodic end of the urea-containing resolving gel. However, at the same time, the SDS concentration of 0.5% w/v in SDS-SB-3 is still sufficiently high for complete SDS/thermal denaturation of the sample.

3.1.3.2 Taking up other Biological Samples

If the samples are in liquid form (e.g. cell culture supernatants, cell homogenates) and if the Aβ peptide concentration is sufficiently high it is possible to take up one volume unit of sample with one volume unit of the double concentrated SDS-SB-2 (table 3).

3.1.3.3 Taking up Samples After Immunoprecipitation (IP)

The APP metabolites which have been immobilized using magnetic Dynabeads (see below) are eluted from the antigen binding after the final washing step at 37° C. for 10 min in an ultrasonic bath using SDS-SB-1 or SDS-PB-3 (without 2-mercaptoethanol in each case). Addition of 2-mercaptoethanol to 2.5% w/v is followed by heating at 95° C. for 5 min. When SDS-PB-3 is used, the samples can subsequently be concentrated three-fold again by concentration to the dry substance and taking up with $H_2O_{dd}$ using a SpeedVac.

3.2 Conventional Aβ 2D-PAGE (Carrier Ampholyte IEF)

The carrier ampholyte IEF in round gels of the first analytical dimension and the vertical Aβ SDS-PAGE of the second analytical dimension are carried out using the mini-protean II 2-D cell system from Bio-Rad.

3.2.1 Materials and Reagents for the Carrier Ampholyte IEF

Bio-RAD (Richmond, Calif., USA): Mini-Protean II 2-D cell system, glass tubes (Ø 1 mm), agarose (162–0017); Merck (Darmstadt, Germany): CHAPS (order No. 1.11662.0010), sodium hydroxide pellets analytical grade (NaOH, order No. 6498), bromophenol blue (order No. 8122), phosphoric acid 85% ($H_3PO_4$, order No. 1.00573.1000); Serva (Heidelberg, Germany): Servalyt® pH 5–6 (order No. 42924) pH 4–7 (order No. 42948) pH 3–10 (order No. 42951); Fluka (Buchs, Switzerland): Igepal CA 630 (NP 40, order No. 56741)

GibcoBRL/Life Technologies (Karlsruhe, Germany): urea (order No. 15716-012);

Sigma (Steinheim, Germany): 2-mercaptoethanol (order No. M-7154)

Biomol (Hamburg, Germany): sodium lauryl sulfate, ultra pure, 2×cryst. (SDS, order No. 51430), bis(2-hydroxyethyl)iminotris(hydroxymethyl)methane (bis-tris, order No. 50003), N,N'-bis(2-hydroxyethyl)glycine analytical grade. (bicine, order No. 01848)

3.2.2 Taking up of Samples for the Carrier Ampholyte IEF

The samples are taken up in IEF-SB (table 4a). Dry substance and Dynabeads magnetically immobilized by means of MSP (see below) are directly taken up with IEF-SB immediately before IEF and incubated in an ultrasonic bath at 37° C. for 10 min. To take up CSF samples, one volume unit of CSF is taken up with one volume unit of IEF-SB and incubated in an ultrasonic bath at 37° C. for 10 min.

3.2.3 First Analytical Dimension: Carrier Ampholyte IEF in Round Gels

Glass tubes (Ø b 1mm) are charged with the monomer solution from table 4b for the gel polymerization. The IEF round gels are polymerized to a length of 60 mm. 20 μl of sample after direct taking up in IEF-SB (10 μl of CSF plus 10 μl of IEF-SB) or 10 μl of eluate from the immunoprecipitation in IEF-SB (table 4a) are loaded and covered with a layer of the cathodic electrolyte. This side of the glass tubes is connected to the upper cathodic electrolyte chamber. The composition of anolyte and catholyte for the carrier ampholyte IEF is to be found in table 4c.

Focussing is then carried out at room temperature as follows: 100V×1 h, 200V×11 h, 500V×2 h, 1000V×1 h (Σ4300 V×h).

After IEF, the round gels are ejected from the glass tubes under water pressure and incubated in IEF equilibration buffer (table 4d) at room temperature for 5 min. The IEF gels are then placed on the stacking gel (see above) of the Aβ SDS-PAGE and fixed in their position using the IEF agarose solution (table 4d). A sample well for loading synthetic Aβ peptides or $M_r$ marker proteins for comparison is shaped in the hot agarose using a Teflon tooth.

3.2.4 Second Analytical Dimension: Aβ SDS-PAGE

The Aβ SDS-PAGE took place as stated in table 1 and 2 (resolving gel: 12% T/5% C/8M urea). One comb gel is not polymerized. The gel thickness of the resolving gels used is 1 mm. The electrophoresis takes place at room temperature: 10 min./60V, 90 min/120V.

3.3 Aβ IPG 2D-PAGE 3.3.1 Material and Reagents

GibcoBRL/Life Technologies (Karlsruhe, Germany): urea (order No. 15716-012) Merck (Darmstadt, Germany): CHAPS (order No. 1.11662.0010), bromophenol blue (order No. 8122), glycerol (100%) (order No. 1.04092.1000)

Biomol (Hamburg, Germany): sodium lauryl sulfate, ultra pure, 2×cryst. (SDS, order No. 51430); Serva (Heidelberg, Germany): Serdolit MB-1 (order No. 40701), dithiotreitol (DTT, order No. 20710)

Amersham Pharmacia Biotech AB (AB (Buckinghamshire, England): Pharmalyte pH 3–10 (order No. 17-0456-01), pharmalyte pH 4-6.5 (order No. 17-0452-01), immobiline dry strip 70×3×0.5 mm, pH 4–7 L (order No. 17-6001-10); Sigma (Steinheim, Germany): iodoacetamide (order No. I-6125)

BioRAD (Richmond, Calif., USA): agarose (162–0017)

3.3.2 Taking up of Samples

The samples are taken up in IPG-SB (table 5a). Dry substance and Dynabeads magnetically immobilized by means of MSP (see below) are taken up directly with the IPG-SB immediately before IEF and incubated in an ultrasonic bath at 37° C. for 10 min. Taking up of liquid biological samples: after removal of the mixed bed ion exchanger (Serdolit MB-1), the IPB-SB is divided into aliquots (e.g. 100 µl) in Eppendorf sample vessels and concentrated to the dry substance at room temperature using a SpeedVac. The IPG-SB introduced as dry substance is taken up with sample with the ratio 1:1 by volume (e.g. 100 µl) and, after a vortex step (1 min.), incubated in an ultrasonic bath at 37° C. for 10 min.

3.3.3 IPG-IEF

The IEF using commercial IPG "DRYSTRIPS" took place in accordance with the manufacturer's protocol (Amersham Pharmacia Biotech/brief instructions 71-5009-57, edition AA, 99–04). IPG "DRYSTRIPS" (4–7, linear pH gradient, length 7 cm) were rehydrogenated to a gel thickness of 0.5 mm using the rehydrogenation solution from table 5a at room temperature overnight. The sample loading device ("sample cups") is placed on the basic side of the IPG strips, at about pH 6.5 (cathodic loading) and 30 µl of sample is loaded. The IPG-IEF takes place for 30 min/300V, 30 min/800V, 30 min./1400V and 5 h/2000V (Σ12500 V×h).

3.3.4 Second Analytical Dimension: Aβ SDS-PAGE

The IPG-IEF is followed by equilibration of the "DRYSTRIPS" for 2×10 min. (table 5b). The first equilibration solution contains DTT (50 mg/5 ml), the second solution iodoacetamide (240 mg/5 ml) for neutralization of excess DTT, which otherwise leads to color artefacts on silver staining of the gels. The second equilibration step is unnecessary for the Western immunoblot. The equilibrated IPG "DRYSTRIPS" are fixed on the stacking gel of the Aβ SDS-PAGE using agarose solution (table 5c). A sample well for loading synthetic Aβ peptides or $M_r$ marker proteins for comparison is made in the hot agarose using a Teflon tooth. The electrophoresis takesplace in accordance with 3.1.2.

3.4 Immunoprecipitation 3.4.1 Material and Reagents, Antibodies

Biochrom KG (Berlin, Germany): HEPES (order No. L1603), PBS Dulbecco, without $Ca^{++}$, without $Mg^{++}$ (order No. L182-50); Merck (Darmstadt, Germany): sodium hydroxide pellets analytical grade (NaOH, order No. 6498); sodium chloride (NaCl, order No. 1.01540.0500); Fluka (Buchs, Switzerland): Igepal CA 630 (NP 40, order No. 56741), sodium deoxycholate (Na-DOC, order No. 30968); Biomol (Hamburg, Germany): sodium lauryl sulfate ultra pure, 2×cryst. (SDS, order No. 51430);

Boehringer (Mannheim, Germany): proteinase inhibitor cocktail tablets, complete™ Mini (order No. 1836153); Deutsche Dynal GmbH (Hamburg, Germany): Dynabeads® M280 sheep anti-mouse IgG (order No. 112.02); Biometra (Göttingen, Germany): magnetic separation stand (MPS); Sigma (Steinheim, Germany): bovine albumin (BSA, order No. A-4378), 2-mercaptoethanol (order No. M-7154), sodium azide (Na azide, order No. A-2002); Paesel+Lorei (Hanau, Germany): tris ultra pure (order No. 100840); Schering AG (Berlin, Germany): mAb1E8 (mouse IgG1);

Senetek PLC Drug Delivery Technologies, Inc. (St. Louis, Mo., USA): mAb 6E10, purified mouse IgG1 (order No. 320-02).

3.4.2 Preparation of Dynabeads M-280 (Sheep Anti-mouse IgG)

Shake 250 µl of suspension ($6.7×10^8$ beads/ml) thoroughly without forming a foam and wash with 1 ml of PBS/BSA (0.15 M NaCl in 0.01 M Na phosphate, 0.1% w/v BSA) for 3×5 min. Immobilize beads in the magnetic separation stand (MSP) of Biometra (Göttingen, Germany) and remove supernatant.

3.4.3 Pretreatment of the Biological Samples 0.75 volume units of sample are taken up with 0.25 volume units of protein inhibitor cocktail stock solution (PI stock solution). PI stock solution: dissolve 1 tablet of Complete™ Mini in 1.5 ml $H_2O_{dd}$.

3.4.4 mAb Activation of the Magnetic Microparticles ("Beads") Using the Direct IP Method About $1.675×10^8$ beads (250 µl of prepared bead suspension, see above) are magnetically immobilized on the walls of 1.5 ml Eppendorf cups in the MSP and incubated with 7.5 µg of mAb 6E10 (Senetek Drug Delivery Technologies, Inc., St. Louis, Mo., USA) or 10 µg of mAb 1E8 (Schering AG, Berlin, Germany) in 250 µl of PBS/BSA at 4° C. for 20 h. Then washed with 1 ml of PBS/BSA for 4×30 min and finally taken up in 250 µl of PBS/BSA/0.01% Na azide and stored at 4° C. until used for the immunoprecipitation. The beads activated in this way can be stored for up to 3 months with negligible loss of capacity. Immediately before use in the immunoprecipitation of biological samples, the activated beads are washed with 250 µl of PBS/BSA without addition of Na azide for 3×3 min.

3.4.5 Immunoprecipitation from Human CSF a) Without Detergents

25 µl of activated DynaBeads (about $1.675×10^7$ beads) are mixed with 268 µl of CSF/PI stock solution (200 µl of CSF+68 µl of PI stock solution) and made up to 1 ml with 732 µl of 50 mM HEPES buffer, pH 7.4, in Eppendorf cups. Incubation takes place on a shaking mixer (continuous agitation of the sample) at 4° C. for 20 h. The beads are then immobilized in the MSP stand and the supernatant is removed. Thereafter the beads are washed with 1 ml of PBS/0.1% BSA at room temperature for 4×5 min. Finally, the beads are washed in 1 ml of 10 mM tris/HCl (pH 7.5) at room temperature for 1×3 min. For the Aβ SDS-PAGE, the samples of magnetically immobilized beads are taken up with 25 µl of SDS-PB-1 at 95° C. for 5 min. For the Aβ 2D-PAGE, 25 µl of IEF-SB or IPG-SB are used for taking up, and incubation takes place in an ultrasonic bath at 37° C. for 10 min. 4 µl of sample are loaded for the Aβ SDS-PAGE, corresponding to the amount of Aβ peptides present in a volume of 32 µl of CSF. 10 µl are loaded for the Aβ 2D-PAGE, corresponding to the amount of Aβ peptides present in a volume of 80 µl of CSF.

b) With Detergents ($RIPA_{0.5x}$-IP)

200 µl of CSF are mixed with 200 µl 5-fold concentrated $RIPA_{0.5x}$ buffer (table 6) and made up to 1 ml with 600 µl of $H_2O_{dd}$ in Eppendorf cups. The procedure for the immunoprecipitation corresponds to the method described under A. The $RIPA_{0.5x}$ buffer contains protease inhibitors (table 6).

3.4.6 Immunoprecipitation from Human Brain Tissue ($RIPA_{1x}$-IP)

Brain tissue (about 50 mg) is homogenized with 1 ml $RIPA_{1x}$ buffer (table 6) in 1.5 ml Eppendorf reaction vessels using an ultrasonic probe and then centrifuged at 20,000 g for 5 min (4° C.). The supernatant is removed and the protein content of the homogenate supernatant is adjusted to 3 mg/ml with RIPA$_{1x}$ buffer, and 1 ml of brain homogenate is immunoprecipitated together with 50 µl of activated Dyna-Beads (about 3.35×10$^7$ beads) as described under (a). The RIPA$_{1.0x}$ buffer contains protease inhibitors (table 6).

3.4.7 Immunoprecipitation from Cell Culture Supernatants (RIPA$_{0.5x}$-IP)

400 µl of cell culture supernatant are mixed with 100 µl of 5-fold concentrated RIPA$_{0.5x}$ buffer (alternative: 800 µl of cell culture supernatant with 200 µl of 5-fold concentrated RIPA$_{0.5x}$ buffer) and 25 µl of activated DynaBeads and immunoprecipitated as described under (a). 6 µl of sample are loaded for the Aβ SDS-PAGE, corresponding to the amount of Aβ peptides present in a volume of 96 µl of cell culture supernatant.

3.5 Fixation and Silver Staining 3.5.1 Reagents

Merck (Darmstad, Germany): sodium thiosulfate pentahydrate analytical grade (Na$_2$S$_2$O$_3$, order No. 1.06516.0500), sodium carbonate analytical grade (Na$_2$CO$_3$, order No. 1.06392.1000), glycine buffer substance (order No. 1.04169.0250), formaldehyde min. 37% analytical grade (order No. 1.04003.1000), glutaraldehyde 25% strength (order No. 8.20603.0100), sodium acetate anhydrous (order No. 1.06268.1000);

Paesel+Lorei (Hanau, Germany): silver nitrate analytical grade (order No. 27-100-601);

Central pharmacy of Göttingen University: ethanol 99.9%, denatured 3.5.2 Procedure After Aβ SDS-PAGE or Aβ 2D-PAGE, the peptides and proteins are fixed with glutaraldehyde in borate/phosphate buffer as described by Wiltfang et al. (Wiltfang et al., 1997) at room temp. for 45 min. The procedure for the silver staining is a slight modification of that of Heukeshoven et al. (Heukeshoven and Dernick, 1988) (table 7)

3.6 Western Immunoblot 3.6.1 Material and Reagents, Antibodies

Paesel+Lorei (Hanau, Germany): tris ultra pure (order No. 100840); Sigma (Steinheim, Germany): boric acid (boric acid, order No. B-7901), sodium azide (Na azide, order No. A-2002); J. T. Baker (Deventer, Holland): methanol (order No. 9263); BioRad Laboratories (Hercules, Calif., USA): filter paper extra thick (order No. 1703960), non-fat dry milk (order No. 170-6404); Millipore Corporation (Bedford, Mass., USA): immobilon-P transfer membrane (order No. IPVH000010); Hoefer Pharmacia Biotech Inc. (San Francisco, Calif. USA): SemiPhor semi-dry transfer unit (order No. 80-6211-86); Biochrom KG (Berlin, Germany): PBS Dulbecco, without Ca$^{++}$, without Mg$^{++}$ (order No. L182-50); Schering AG (Berlin, Germany): mAb 1E8 (mouse IgG1); Senetek PLC Drug Delivery Technologies. Inc. (St. Louis. Mo., USA): purified mAb 6E10, mouse IgG1 (order No. 320-02);

Roth (Karlsruhe. Germany): ROTI-BLOCK (order No. A151.1).

3.6.2 Procedure for the Western Immunoblot

Aβ SDS-PAGE or Aβ 2D-PAGE is followed by transfer by means of semidry Western blot and a multiphase buffer system to PVDF detection membranes. The blot buffers are compiled in table 8.

The structure of the blot sandwich from the anode to the cathode is as follows: a layer of filter paper with buffer A, a layer of filter paper and the PVDF membrane with buffer B, gel and finally two layers of filter paper with buffer C. Gels are incubated in buffer C for about 10 sec immediately following the electrophoresis. Extra thick filter paper from BioRad is used as filter paper. After examination of PVDF membranes from various manufacturers, the Immobilon-P membrane from Millipore gave the least background staining and most effective immobilization of the Aβ peptides, especially Aβ$_{1-42}$, within the immunoblot protocol. The Immobilon-P membranes are wetted in accordance with the manufacturer's information with methanol before use, subsequently incubated in H$_2$O$_{dd}$ for 1 min. and then transferred into buffer B. The transfer takes place for 30 min. for Aβ SDS-PAGE (Ø 0.5 mm) or for 45 min for Aβ 2D-PAGE gels (Ø 1.0 mm) at room temperature with 1 mA/cm$^2$.

After completion of the Western blot, the Immobilon-P membrane is washed in H$_2$O$_{dd}$ for about 30 sec. and cooked in PBS (without Tween-20) in a microwave for 3 min. The cooking step is essential in order to achieve the maximum detection sensitivity.

3.6.2.1 Immunoblot 1 (Milk Powder Blocking Step)

The buffers, solutions and antibodies used for immunoblot 1 are summarized in table 9a & b.

Blocking step: in 4 ml of PBS-T-M/cm$^2$ membrane at room temperature for 1 h

Incubation with primary mAb: 15 h at 4° C. and finally 30 min. at room temp. in a 1:4,000 dilution of mAb 1E8 (Schering AG, Berlin, Germany) or in a 1:1,000 dilution of mAb 6E10 (purified: 1 mg/ml; Senetek Drug Delivery Technologies, Inc., St. Louis, Mo., USA) in 0.074 ml of PBS-T-M/cm$^2$ (sealing in plastic film, high frequency agitation with rotary mixer)

Washing step 1: with PBS-T (4 ml/cm$^2$) at room temp. for 3×10 min.

Incubation with secondary mAb: 1 h at room temp. with a 1:3,000 dilution of the secondary mAb (biotinylated anti-mouse IgG, horse, H+L; Vector Laboratories, Burlingame, Calif., USA) in 0.074 ml of PBS-T-M/cm$^2$ of membrane (sealing in plastic film, high frequency agitation with rotary mixer)

Washing step 2: as washing step 1

Streptavidin-avidin enhancement: 1 h at room temperature with 1:3,000 dilution of streptavidin biotinylated horseradish peroxidase complex RPN 1051 (Amersham, Buckinghamshire, England) in PBS-T with 0.26 ml/cm$^2$ of membrane (sealing in plastic film, high frequency agitation with rotary mixer)

Washing step 3: as washing step 1

ECL development: with 0.1 ml/cm$^2$ ECLPlus™ solution (RPN 2132; Amersham, Buckinghamshire, England) at room temp. for 5 min. in accordance with the manufacturer's information. Subsequently removal of excess reagent (between 2 sheets of filter paper for 5 sec.) and wrapping of the wet membrane in cling film.

3.6.2.2 Immunoblot-2 (ROTI-BLOCK)

The buffers, solutions and antibodies used for immunoblot 2 are summarized in table 9a & b.

Blocking step: in 25 ml of 1:10 ROTI-BLOCK/H$_2$O dd at room temperature for 1 h.

Incubation with primary mAb: 15 h at 4° C. and finally 30 min. at room temp. in a 1:4,000 dilution of mAb 1E8 (Schering AG, Berlin, Germany). mAb 6E10 is not compatible with ROTI-BLOCK because of a high background signal.

Washing step 1: with PBS-T (4 ml/cm$^2$) at room temp. for 3×10 min.

Incubation with secondary Ab: 1 h at room temp. with a 1:3,000 dilution of the secondary mAb (biotinylated anti-mouse IgG, horse, H+L; Vector Laboratories, Burlingame, Calif., USA) in 0.074 ml of PBS-T-M/cm$^2$ of membrane (sealing in plastic film, high frequency agitation with rotary mixer)

Washing step 2: as washing step 1

Streptavidin-avidin enhancement: 1 h at room temperature with 1:3,000 dilution of streptavidin biotinylated horseradish peroxidase complex RPN 1051 (Amersham, Buckinghamshire, England) in PBS-T with 0.26 ml/cm² of membrane (sealing in plastic film, high frequency agitation with rotary mixer)

Washing step 3: as washing step 1

ECL development: with 0.1 ml/cm² ECLPlus™ solution (RPN 2132; Amersham, Buckinghamshire, England) at room temp. for 5 min. in accordance with the manufacturer's information. Subsequently removal of excess reagent (between 2 sheets of filter paper for 5 sec.) and wrapping of the wet membrane in cling film.

3.6.3 Quantification of the ECL Signal by Densitometric Film Evaluation

3.6.3.1 Material and Reagents

Amersham Pharmacia Biotech AB (Buckinghamshire, England): ECL$^{Plus}$ Western blotting detection system (order No. RPN 2132), Hyperfilm™ ECL™ (order No. RPN 2103H); Schleicher und Schuell (Dassel, Germany): gel blotting paper (order No. 426690); Tropix (Bedford, Mass., USA): development folders, 14 cm×19 cm (order No. XF030); Biometra (Göttingen, Germany): BioDoc software Epson Germany GmbH (Düsseldorf, Germany): laser scanner Epson GT 9000

3.6.3.2 ECL Development

After the last washing step in PBS-T, the PVDF membrane is placed on a Teflon substrate and excess washing buffer is removed by putting on a layer of KIMWIPES® Lite 200 laboratory wipes. This is followed by incubation with 0.1 ml/cm² ECLPlus™ solution at room temperature for 5 min. In order to remove excess ECLPlus™ solution, the membrane is placed between two layers of gel blotting paper and, for signal detection, transferred into a development folder which ensures optimal detection and prevents the membrane from drying out.

3.6.3.3 Quantification

8 µl portions of the CSF sample were loaded. Each gel carried serial dilutions of a mixture of synthetic Aβ peptides 1-40 and 1-42 (A$\beta_{1-42}$: 5,10,15,25 pg; A$\beta_{1-40}$: 20, 50, 75, 100 pg). The measurements were carried out as triplicate determination. The Aβ peptide concentrations were calculated for each gel on the basis of a calibration series. The mean (n=3) and coefficient of variation (CV) was then calculated. The intraassay coefficient of variation was calculated on the basis of the three single determinations which were determined each on separate gels in the same experiment using identical stock solutions. The interaasasy coefficient of variation was determined on the basis of the A$\beta_{1-42}$ means which were measured in independent experiments (i.e. study days). The outliers found by triplicate determination were not eliminated when calculating the two coefficients of variation, i.e. all Aβ peptide bands technically capable of evaluation were included in the calculation.

In addition, the raw data (area units) of the three bands per lane were collected for A$\beta_{1-40}$, A$\beta_{1-42}$ and A$\beta_{1-38}$ and related to one another as ratios (A$\beta_{1-42}$/A$\beta_{1-40}$, A$\beta_{1-42}$/A$\beta_{1-38}$).

ECL detection after the Western immunoblot (primary mAb: 1E8) took place by exposure of Hyperfilm™ for 5 min. The densitometric evaluation took place using a laser scanner (Epson GT 9000) and evaluation software (Biometra, BioDoc software).

3.6.4 Quantification of the ECL Signal Using a CCD Camera

3.6.4.1 Material and Equipment

Bio-RAD Laboratories (Hercules, Calif., USA): Fluor-S MAX Multilmager System (order No. 170-7720); Quantity One Software (order No. 170-8601)

3.6.4.2 ECL Development

ECL development was carried out as described under 3.6.3.2.

3.6.4.3 Procedure

10 µl portions of CSF sample were loaded. Each gel carried serial dilutions of a mixture of the synthetic Aβ peptides 1-37, 1-38, 1-39, 1-40 and 1-42 (A$\beta_{1-37}$: 5, 10, 20, 40, 80 pg; A$\beta_{1-38}$; 15, 30, 60, 90, 120 pg; A$\beta_{1-39}$: 5, 10, 20, 30, 60 pg; A$\beta_{1-40}$: 25, 50, 100, 200, 300 pg; A$\beta_{1-42}$: 5, 10, 20, 40, 80 pg). The ECL detection using a CCD camera took place with a resolution of 80×80 µm by means of serial exposure times for 5, 20, 60 and 120 seconds. The gels were quantified relative to their respective calibration series using the evaluation software "Quantity One" (Bio-RAD Laboratories, Hercules, Calif., USA).

The measurements were carried out as quadrupicate determination. The Aβ peptide concentrations were calculated for each gel on the basis of its calibration series. The mean (n=4) and coefficient of variation (CV) was then calculated. The intraassay coefficient of variation was calculated on the basis of the four single determinations, which were determined each on separate gels in the same experiment using identical stock solutions. The interaasasy coefficient of variation was determined on the basis of the means which were measured in independent experiments (i.e. study days). Outliers found by quadruplicate determination were not eliminated when calculating the two coefficients of variation, i.e. all Aβ peptide bands technically capable of evaluation were included in the calculation.

3.7 Telencephalic Primary Chick Culture

Eggs of the White Leghorn breed of chickens are incubated in an incubator at 37° C. for 10 days. On day 10, the chick embryo is removed under sterile conditions, and the brain is exposed. The anterior cerebral vesicles are removed, freed of the attached meninges and taken up in HEPES-buffered DMEM. The tissue obtained in this way is subjected to a trypsin digestion for 15 minutes and, after washing with DMEM three times, drawn up through a needle several times. After the homogenate has been centrifuged at 550 g for five minutes, the supernatant is decanted off, the pellet is taken up in cultivation medium (DMEM+5% fetal calf serum+5% chicken serum) and again drawn up through a needle. Following a determination of the cell count using a Neubauer counting chamber, the cell density of the suspension is adjusted to 1.5 million cells/ml, and the latter are plated out into the cultivation vessels to result in a cell density of 375,000 cells/cm². To improve adhesion of the cells, the cultivation vessels have previously been coated for 24 hours with a poly-L solution (0.1 mg/ml poly-L lysine in 0.1M borate/NaOH buffer, sterilized by filtration, pH 8.4). 50% of the medium is changed on the 2nd day of cultivation, and 100% of the medium is changed on the 5th day of cultivation with simultaneous addition of the test substance to be investigated. The incubation times may be up to 48 hours.

3.8 Obtaining CSF

Three to 10 ml of lumbar CSF was obtained by lumbar CSF puncture and collected in polypropylene sample vessels. After centrifugation (1,000 g, 10 min, 4° C.), the samples were stored in 150 µl aliquots in polypropylene vessels (Eppendorf, 1.5 ml) at −80° C. within 24 hours until the determination. The samples must not undergo multiple freezing and thawing.

3.9 Patients

Figure 1:
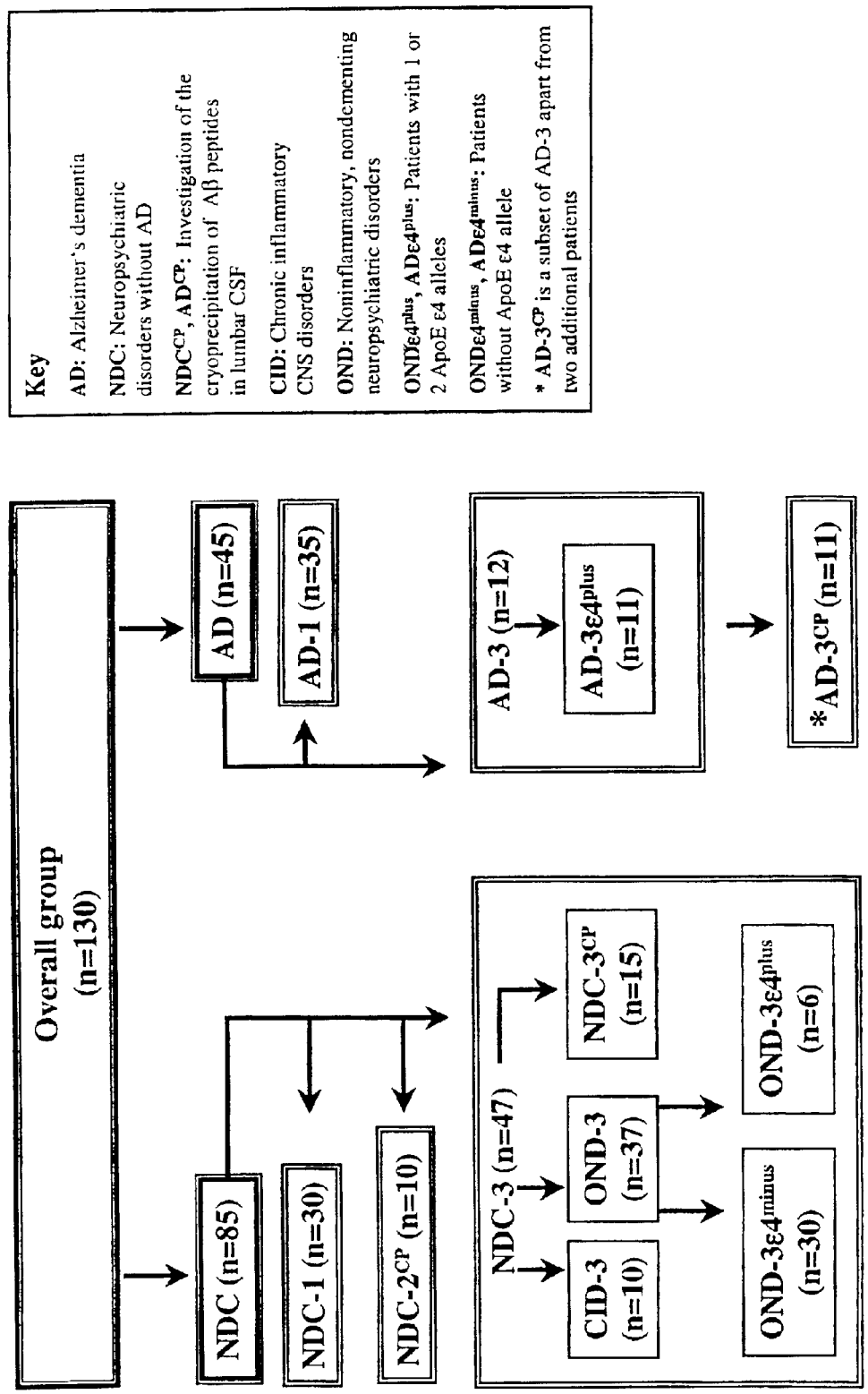
FIG. 1: a flow diagram of the groups of patients in which Aβ peptides were measured in the CSF or plasma by Aβ SDS-PAGE/immunoblot. The groups of patients in a single frame are subsets of their superior groups in double frames. Some patients are present simultaneously in more than one group (cf. tables 5a–d) The NDC-3 subgroups IP plasma-3 (n=5), IP-CSF-3 (n=5) and SDS-CSF-3 (n=5) are not included (cf. 2.9.1).

In total, the lumbar CSF of 130 patients was investigated. Aβ peptides were additionally measured in the blood plasma for five of these patients. The patients were distributed over the two diagnostic supergroups of neuropsychiatric disorders excluding Alzheimer's dementia ("neuropsychiatric desease controls", NDC) and patients with clinically probable (sporadic) Alzheimer's dementia (AD). Determined by the methods, a plurality of NDC and AD groups each with different patients were investigated, and associated groups of patients are identified by consecutive arabic numerals (e.g. NDC-1, AD-1). The NDC-1 and NDC-2 groups also contain patients with dementing disorders of etiology other than AD. The NDC-3 group contains only patients with non-dementing neuropsychiatric disorders. This group has been differentiated into patients with chronic inflammatory disorders of the CNS ("chronic inflammatory CNS disease", CID-3) and the remaining patients with other neuropsychiatric disorders ("other neruopsychiatric diseases", OND-3). A further differentiation was made within the OND-3 and AD-3 group depending on the ApoE ε4 genotype. FIG. 1 summarizes the groups of patients and their hierarchical association. Table 10a–d specifies the patients present simultaneously in more than one group of patients.

The clinical diagnosis took place in accordance with ICD-10. Diagnosis of Alzheimer's dementia was undertaken in accordance with the criteria, which are predominantly used internationally, of the "Work Group of the National Institute of Neurological and Communicative Disorders and Stroke (NINCDS)" and the guidelines of the "Alzheimer's Disease and Related Disorders Association (ARDA)" (McKhann et al., 1984). The samples were all obtained during routine clinical diagnosis. No additional CSF volume was obtained for the measurements presented here. Accordingly, retrospective investigation was possible only if aliquots of CSF were available after completion of routine diagnosis.

3.9.1 NDC-1 and AD-1

Aβ peptides were quantified in lumbar CSF of 65 patients by Aβ SDS-PAGE/immunoblot 1 and densitometric evaluation of films. The sample taking up of the samples previously frozen untreated after CSF puncture and centrifugation followed in accordance with 3.2.2a. The patients' diagnoses and measurements are shown in table 12 and summarized in table 13. Patients simultaneously represented in other groups are to be found in table 10a and 10c.

NDC-1: n=30, age=59.2±12.6 (mean±SD), sex: 19/11 (female/male).

AD-1: n=35, age=69.7±8.8 (mean±SD), sex: 18/17 (female/male).

Ten of the AD-1 and 20 of the NDC-1 patients were investigated comparatively by means of immunoprecipitation (mAb 6E10, IP without detergents) and Aβ SDS-PAGE/immunoblot 1 (cf. table 12 and 13). All the patients in the AD-1 group were investigated comparatively with a commercial ELISA Aβ$_{1-42}$.(cf. table 13).

3.9.2 NDC-2$^{CP}$

In ten patients, the concentration of Aβ$_{1-40}$ and Aβ$_{1-42}$ in the lumbar CSF was investigated as a function of the sample pretreatment by Aβ SDS-PAGE/immunoblot 1 and densitometric evaluation of films. The extent of the reduction caused by cryoprecipitation (CP) in Aβ peptides was also investigated. The patients' samples were divided into aliquots after CSF puncture and centrifugation. One aliquot was pretreated before freezing with SDS/thermal denaturation as described in 3.2.2a, called Aβ$_{1-40}$SDS or Aβ$_{1-42}$SDS hereinafter. The other aliquot was frozen without pretreatment at −80° C., called Aβ$_{1-40}$native or Aβ$_{1-42}$native hereinafter. The patients' diagnoses and measurements are summarized in table 16a and 16b. Patients simultaneously represented in other groups are to be found in table 10a.

NDC-2$^{CP}$: n=10, age=45.8±13.4 (mean±SD), sex: 6/4 (female/male)

3.9.3 NDC-3 and AD-3 with Subgroups

The concentration of Aβ peptides in the lumbar CSF of 49 patients in the NDC-3 group and 12 patients in the AD-3 group was investigated by Aβ SDS-PAGE/immunoblot 2 and CCD camera. The sample taking up of the samples frozen untreated after CSF puncture and centrifugation followed in accordance with 3.2.2a. The patients' diagnoses and measurements are shown in table 19 and summarized in table 20. Patients simultaneously represented in other groups are to be found in table 10b, c and d.

NDC-3: n=47, age=45.2±15.8 (mean±SD), sex: 19/28 (female/male).

AD-3: n=12, age=73.0±7.9 (mean±SD), sex: 9/3 (female/male).

Further subgroups within the NDC-3 group were formed depending on the nature of the sample and sample pretreatment: paired CSF and EDTA plasma samples were obtained for five of the NDC-3 patients. These samples were investigated by immunoprecipitation (RIPA-IP, 1E8) and are called IP-CSF-3 and IP-plasma-3 hereinafter. The concentrations of the Aβ peptides measured without previous immunoprecipitation have been summarized comparatively for the latter five patients as the SDS-CSF-3 group (cf. table 20). The concentration of Aβ$_{1-42}$ in CSF was determined using a commercial ELISA (Hulstaert et al., 1999) comparatively for 27 of the NDC-3 patients. A differentiation was made within the NDC-3 group between patients with chronic inflammatory CNS disorders ("chronic inflammatory CNS disease", CID) and patients with other neuropsychiatric disorders ("other neuropsychiatric disease", OND).

OND-3: n=37, age=45.3±16.4 (mean±SD), sex: 15/22 (female/male).

CID-3: n=10, age=44.9±14.2 (mean±SD), sex: 4/6 (female/male).

The CID-3 group was composed of five patients with multiple sclerosis and five patients with an unclear etiology of the chronic inflammatory CNS process.

The OND-3 group is further differentiated depending on the ApoE ε4 genotype into the groups OND-3ε4$^{plus}$ (n=6) and OND-3ε4$^{minus}$ (n=30). Patients in the OND-3ε4$^{plus}$ group have one or two ε4 alleles, patients in the OND-3ε4$^{minus}$ group lack this allele. Since 11/12 AD-3 patients carry one or two ApoE ε4 alleles, the influence of the ε4 allele on the CSF pattern of the Aβ peptides cannot be eliminated, but ε4-independent and therefore more AD-specific effects were found by comparing the AD-3ε4$^{plus}$ (n=11) and OND-3ε4$^{plus}$ (n=6) groups of patients.

The values for the MMSE examination results for the patients, frequencies of the ApoE ε4 alleles, and absolute and relative Aβ peptide CSF concentrations are summarized for the NCD-3, AD-3, IP-plasma-3, IP-CSF-3, and SDS-CSF-3 groups in table 20.

3.9.4 NDC-3$^{CP}$ and AD-3$^{CP}$

The reduction caused by cryoprecipitation (CP) in Aβ$_{1-42}$ in the lumbar CSF was investigated comparatively for 15 patients in the NDC-3 group and 9 patients in the AD-3 group by Aβ SDS-PAGE/immunoblot 2 and CCD camera. The groups are called NDC-3$^{CP}$ and AD-3$^{CP}$ hereinafter. NDC-3$^{CP}$ is entirely a subgroup of NDC-3. AD-3$^{CP}$ (n=11) contains nine patients of the AD-3 group besides in addition two other patients (NP69, NP197). The sample preparation for determining $A\beta_{1-42}$native and $A\beta_{1-42}$SDS took place as described for the NDC-$2^{CP}$ group.

The patients' diagnoses and measurements are summarized in table 21. Patients simultaneously represented in other groups are to be found in table 10b, c and d.

NDC-$3^{CP}$: n=15, age=44.6±15.0 (mean±SD), sex: 5/10 (female/male).

AD$3^{CP}$: n=11, age=70.9±9.0 (mean±SD), sex: 9/2 (female/male).

3.10 Statistics

The testing for significant differences between independent samples took place by the Mann-Whitney U test and for dependent (paired) samples by the Wilcoxon test. The non-parametric regression analysis took place by the Spearman method (correlation coefficient rho or R). The statistics software employed was Statistika (version 5.0). The iterative calculation of diagnostic specificity and sensitivity for the diagnosis of AD depending on different Aβ peptide limits ws undertaken via a "receiver operating characteristic (ROC) curve" (Metz, 1978). The two-sided significance level was fixed at p<0.05.

Results 4.1 Fractionation and Detection of sAPPa and Aβ Peptides 4.1.1 Aβ-SDS-PAGE It is possible by Aβ SDS-PAGE to separate the following synthetic Aβ peptides through a urea-induced conformational change from cathodic (top) to anodic (bottom):

1-33/1-34
1-35
1-37
1-38
1-39
1-42/2-40/3-40
2-42/3-42
3p-42*/3p-40*

*p=pyroglutamate derivatives;

Aβ peptides where separation is lacking or only partial are in one line. Detection took place by silver staining of the resolving gels.

It is possible by Aβ IPG-2D-PAGE to separate the Aβ peptides 2-40/3-40 from 1-42 because the absence of asparte shifts the isoelectric point by one pH unit from 5.37 to 6.37 (cf. FIG. 2a & c and FIG. 24a).

The same pH change emerges for the Aβ peptides 2-42/3-42 in relation to 1-42. It is possible to differentiate between 2-40/2-42 and 3-40/3-42 via the N-terminally selective mAbs 1E8 and 6E10 (cf. 3.1.2). It is noteworthy that N- and C-terminal modifications of the Aβ peptides which lead to an increased aggregation behavior (N-terminal: absence of aspartate and pyroglutamate formation; C-terminal: extension by hydrophobic amino acids) also lead to an increased electrophoretic mobility in the urea-containing resolving gel system. There is thus an analogy between the structure-activity functions in vitro and in vivo.

Comparatively minor changes in the resolving gel matrix (polyacrylamide pore size, molarity of the urea, pH, temperature and ionic strength) and in the cathodic SDS concentration significantly alter the absolute and relative migration behavior of the Aβ peptides. Changes in the total concentration of acrylamide monomer (T %) or in the proportion of bisacrylamide in the total concentration (% C) by only 1–2% with otherwise constant conditions are sufficient for this. Likewise, a selective reduction in the urea concentration from 8 to 7 mol/l or a reduction in the cathodic SDS concentration from 0.25% (w/v) to 0.1% leads to an altered fractionation.

Figure 3:
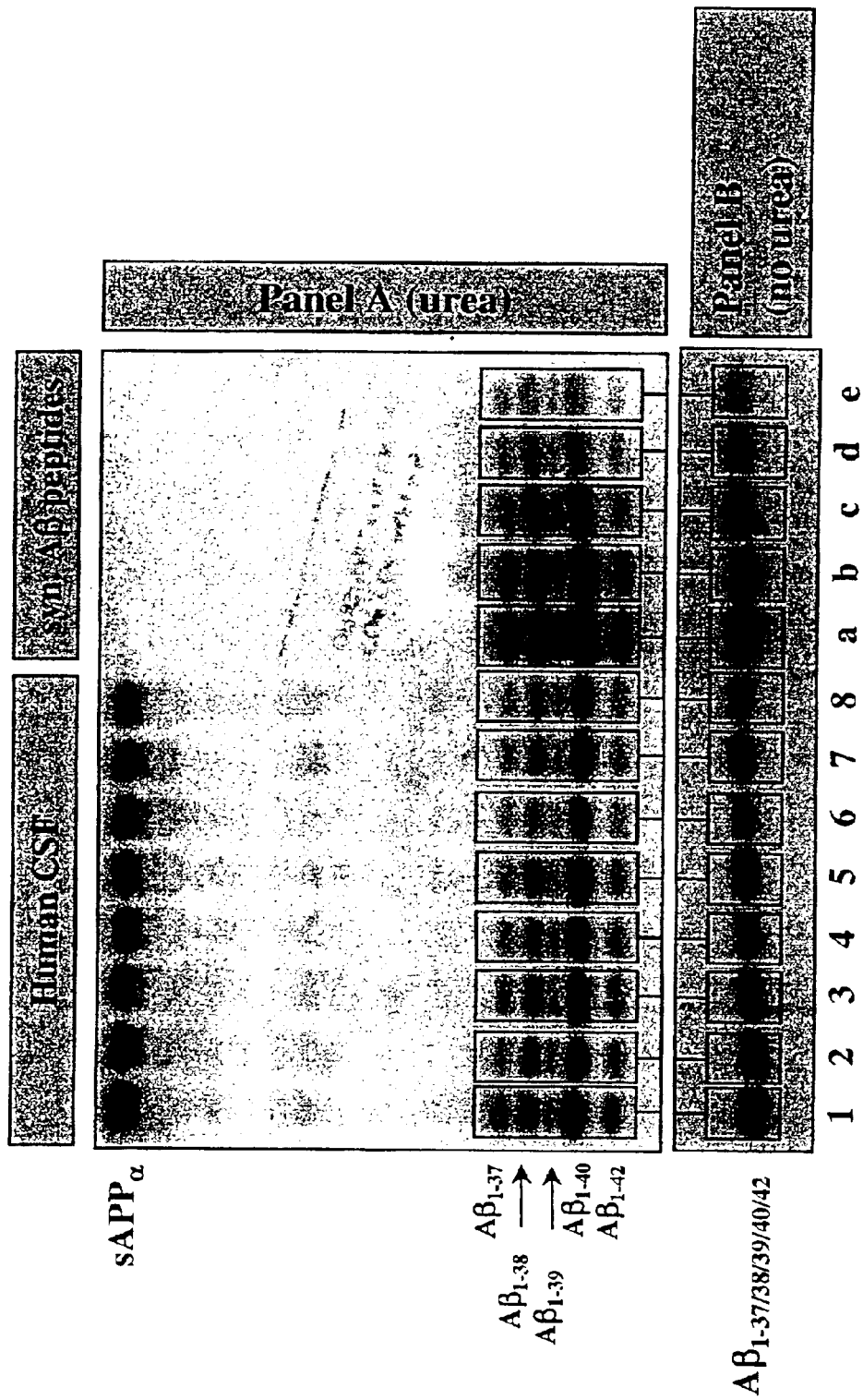
FIG. 3: a determination of Aβ peptides in CSF in NDC-3 by Aβ SDS-PAGE/immunoblot 2 and a comparison between resolving gel with (panel A) and without urea (panel B). The following applies to columns 1 to 8: 10 µl of CSF per patient. The CSF was frozen untreated and then SDS/thermally denatured. The following applies to columns a to e: Mix of synthetic Aβ peptides (dilution series).

By means of Aβ SDS-PAGE, sAPPα is fractionated in the upper (cathodic) compartment in the urea-containing resolving gel, that can be detected by Western immunoblot 1/2 (mAb 1E8) (cf. FIG. 3). Owing the molecular mass of >100,000, sAPPα isoforms are blotted with less efficiency and considerably greater variation, compared with the Aβ peptides, from the small-pore urea-containing resolving gels onto the detection membrane (intraassay coefficient of variation in the CSF>20%). However, the blotting efficiency and fractionation of sAPPα isoforms can be considerably improved if the urea-containing resolving gel system is combined with a cathodic resolving gel compartment not containing urea and with a greater pore size but with the buffer composition otherwise the same (10 T %, 5 C %, no urea). With an unchanged length of the resolving gel in the urea-containing compartment, the quality of the Aβ peptide fractionation is not impaired because the Aβ peptides are still concentrated on migrating through the large-pore compartment within the moving boundary.

Quantification of sAPPα by Aβ SDS-PAGE/immunoblot 2 and CCD camera appears to be very promising for neurochemical dementia diagnosis, because sAPPα was found to be reduced in the CSF in AD and illustrates the α-secretase cut. Thus the Aβ SDS-PAGE/immunoblot allows calculation of sAPPα/Aβ peptide ratios, which represent a measure of the ratio of a-secretase to β/γ secretase activity.

4.1.2 Western Immunoblot 1/2

The mAb 1E8 shows an astonishingly high N-terminal specificity in the Western immunoblot 1/2 because only Aβ peptides truncated by a maximum of one amino acid (aspartate) at the N terminus are detectable in the lower pg range (<200 pg). Accordingly, the Aβ peptides 3-40, 3p-40, 3-42 and 3p-42 are not detected using the mAb 1E8. In these cases, detection is possible by the N-terminally specific mAb 6E10, which is commercially available but with which the detection is about ten to thirty times less sensitive, depending on the blotting conditions.

The detection sensitivity of the Western immunoblot 1 (milk powder block, mAb 1E8) is 1 pg (Aβ1-40) to 2 pg (Aβ1-42) on exposure of the films and 3 pg (Aβ1-40) to 6 pg (Aβ1-42) on signal recording with the CCD camera. The detection sensitivity of the Western immunoblot 2 (ROTI-BLOCK, mAb 1E8) is 0.3 pg (Aβ1-40) to 0.6 pg (Aβ1-42) on exposure of the films and 1 pg (Aβ1-40) to 2 pg (Aβ1-42) on signal recording with the CCD camera. It was possible through development of the Western immunoblot 2 to compensate for the sensitivity of the CCD camera being about three times lower than on exposure of the films. The detection sensitivity of the commercially available N-terminally selective mAb 6E10 in the Western immunoblot with milk powder block is 10 pg (Aβ1-40) to 20 pg (Aβ1-42) on exposure of the films and 30 pg (Aβ1-40) to 60 pg (Aβ1-42) on signal recording with the CCD camera. The mAb 6E10 cannot be used with Rotiblock. It was thus possible to increase the detection sensitivity by up to 30 times compared with the mAb 6E10.

SDS-PAGE resolving gel systems with 8 M urea can, irrespective of the gel dimensions used, be loaded with a maximum of about 5 μl of CSF per mm² surface area of the gel if optimal electrophoretic separation is to be achieved for virtually all the patients' samples. This applies to CSF which has been frozen untreated and then SDS/thermally denatured, or CSF which has been SDS/thermally denatured before the freezing. 5 μl per mm² correspond in the minigel system used to a CSF volume of about 10 μl. The resulting sensitivity is 200 pg/ml for detection of $A\beta_{1-42}$ in human CSF by Aβ SDS-PAGE/immunoblot 2 and CCD camera. A detection sensitivity of at least 200 pg/ml is a precondition for neurochemical dementia diagnosis of AD by determination of the Aβ peptides in the CSF and cannot be achieved for example with the commercially available mAb 6E10.

The sensitivity for detection of $A\beta_{1-42}$ increases to <10 pg/ml on combination of immunoprecipitation (RIPA detergents, mAb 1E8) with Aβ SDS-PAGE/immunoblot 2 and CCD camera. This is precondition for the quantification of Aβ peptides in the plasma by Aβ SDS-PAGE/immunoblot. The intra- and interassay coefficients of variation for the Aβ SDS-PAGE/immunoblot 1 with densitometric evaluation of films are to be found in table 11. The corresponding coefficients of variation for the Aβ SDS-PAGE/immunoblot 2 with CCD camera are to be found in table 18a and b. Intra- and interassay coefficients of variation each of less than 10% were found for the quantification of 20 pg of Aβ peptide.

Quantification using a CCD camera has considerable advantages compared with exposure of films. The light signal can in this case be recorded linearly over 3.8 powers of ten and, in addition, the duration of signal recording can be accurately controlled over a wide range. Accordingly, APP metabolites with a large difference in their signal intensity, such as, for example, sAPPα and $A\beta_{1-42}$, can be quantified over two measurement times (e.g. 10 s and 3 min).

4.2 Patients' Samples

Figure 2:
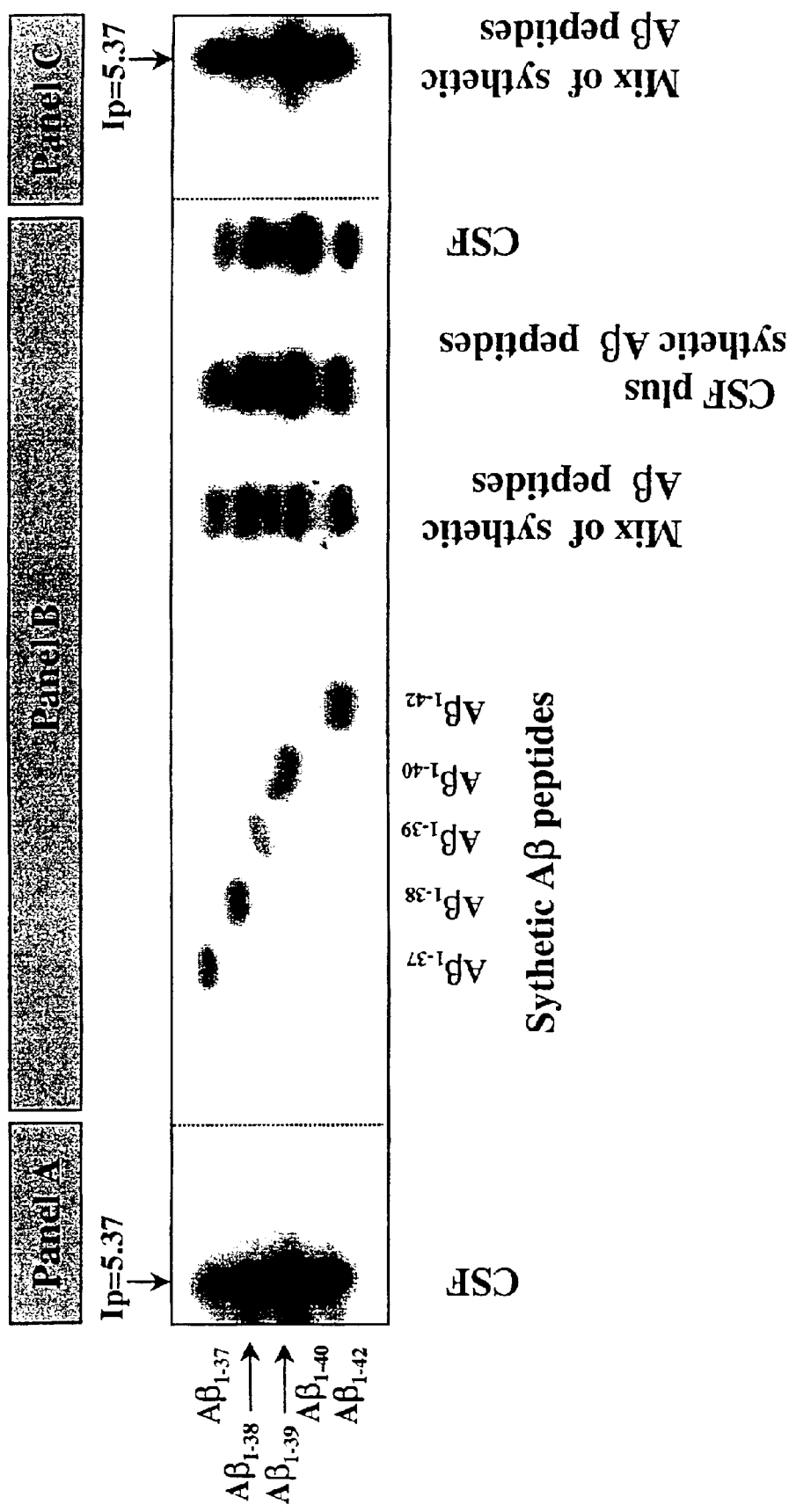
FIG. 2: an Aβ-IPG 2D-PAGE/immunoblot 2 (panel A, C) and Aβ SDS-PAGE/immunoblot 2 (panel B) of synthetic Aβ peptides, human CSF and CSF with addition of synthetic Aβ peptides.

It was previously known that $A\beta_{1-40}$ and $A\beta_{1-42}$ occur frequently and relatively high concentration in human CSF. On the other hand, a characteristic Aβ peptide quintet can frequently be detected in human lumbar CSF by Aβ SDS-PAGE/immunoblot 1/2 both on direct loading after SDS/thermal denaturation and after previous immunoprecipitation using N-terminally selective antibodies (FIG. 3). Three other Aβ peptides are evident above (cathode side) of $A\beta_{1-40}$ and were initially referred to as $A\beta 1-x^a$, $A\beta 1-x^b$ and $A\beta 1-x^c$ and could be identified by Aβ IPG 2D-PAGE/immunoblot with comigration of synthetic Aβ peptides as $A\beta_{1-37/38/39}$ (FIG. 2). The Aβ peptides 1-37, 1-38 and 1-39 are not detectable in the CSF by Aβ SDS-PAGE/immunoblot on carboxy-terminally selective immunoprecipitation against 1-40 and 1-42. Besides the Aβ peptides 1-33, 1-34 and 1-35, it was possible to detect the Aβ peptides 1-37/38/39 in human CSF by MALDI-TOF. The Aβ peptides 1-33/1-34 and 1-35 are usually detectable only at the limit of detection, or are undetectable, in the Aβ SDS-PAGE/immunoblot above (cathode side) of 1-37 in patients' CSF. The Aβ peptides 1-37, 1-38, 1-39, 1-40 and 1-42 are highly and significantly correlated, as is evident from FIG. 10. This indicates a close enzymatic regulation of their production. The synthetic Aβ peptides 1-37, 1-38 and 1-39 were not yet available when the first groups of patients (NCD-1, AD-1, NDC-$2^{CP}$) were investigated. In this case therefore the ratio of $A\beta_{1-42}$ to $A\beta_{1-38}$ was found from the ratios of the area units measured by densitometry for the respective bands in a gel lane. For comparison, the $A\beta_{1-42}/A\beta_{1-40}$ ratio was also expressed via the area units. Since $A\beta_{1-38}$, $A\beta_{1-40}$ and $A\beta_{1-42}$ show, at the same concentration and identical conditions in the Western immunoblot, a different intensity of the ECL signal, the ratios of the area units cannot be equated with the corresponding ratios of the Aβ peptide concentrations found via the calibration line.

In some of the patients with AD, an additional band with the retention factor (Rf) of $A\beta_{2-42}$ is detectable below (anodically) of $A\beta_{1-41}$ by Aβ SDS-PAGE/immunoblot 2 and CCD camera (FIG. 23a). It was possible to identify this band in the CSF in AD as $A\beta_{2-42}$ after previous immunoprecipitation (RIPA-IP, mAb 1E8) by Aβ IPG 2D-PAGE/immunoblot 2 and CCD camera (FIG. 24b). It has not to date been possible to detect $A\beta_{2-42}$ in non-dementing control patients. There is also a massive intracerebral increase in $A\beta_{2-42}$, with a typical distribution in brain regions, in patients with sporadic AD, (cf. 4.2.5). Synthetic $A\beta_{2-42}$ was not yet available for determining Aβ peptides in the CSF for the groups of patients mentioned under 3.9. Accordingly, no quantitative data on $A\beta_{2-42}$ are available for these patients. However, since then another patient group of patients which is not yet mentioned under 3.9 has been measured. $A\beta_{2-42}$ was detectable in some of the patients with AD-4, in some patients with dementing disorders other than AD (nAD-4) and in some patients with non-dementing disorders (NDC-4). In addition, the $A\beta_{1-42}/A\beta_{1-40}$ ratio was significantly reduced in the $A\beta_{2-42}$-positive patients compared with the other patients.

4.2.1 NDC-1 and AD-1

Table 12 gives the clinical data and individual measurements for the patients and table 13 summarizes the statistical characteristics of the AD-1 and NDC-1 groups of patients. The CSF samples were analyzed by Aβ SDS-PAGE/immunoblot 1 and densitometric evaluation of films.

Figure 4:
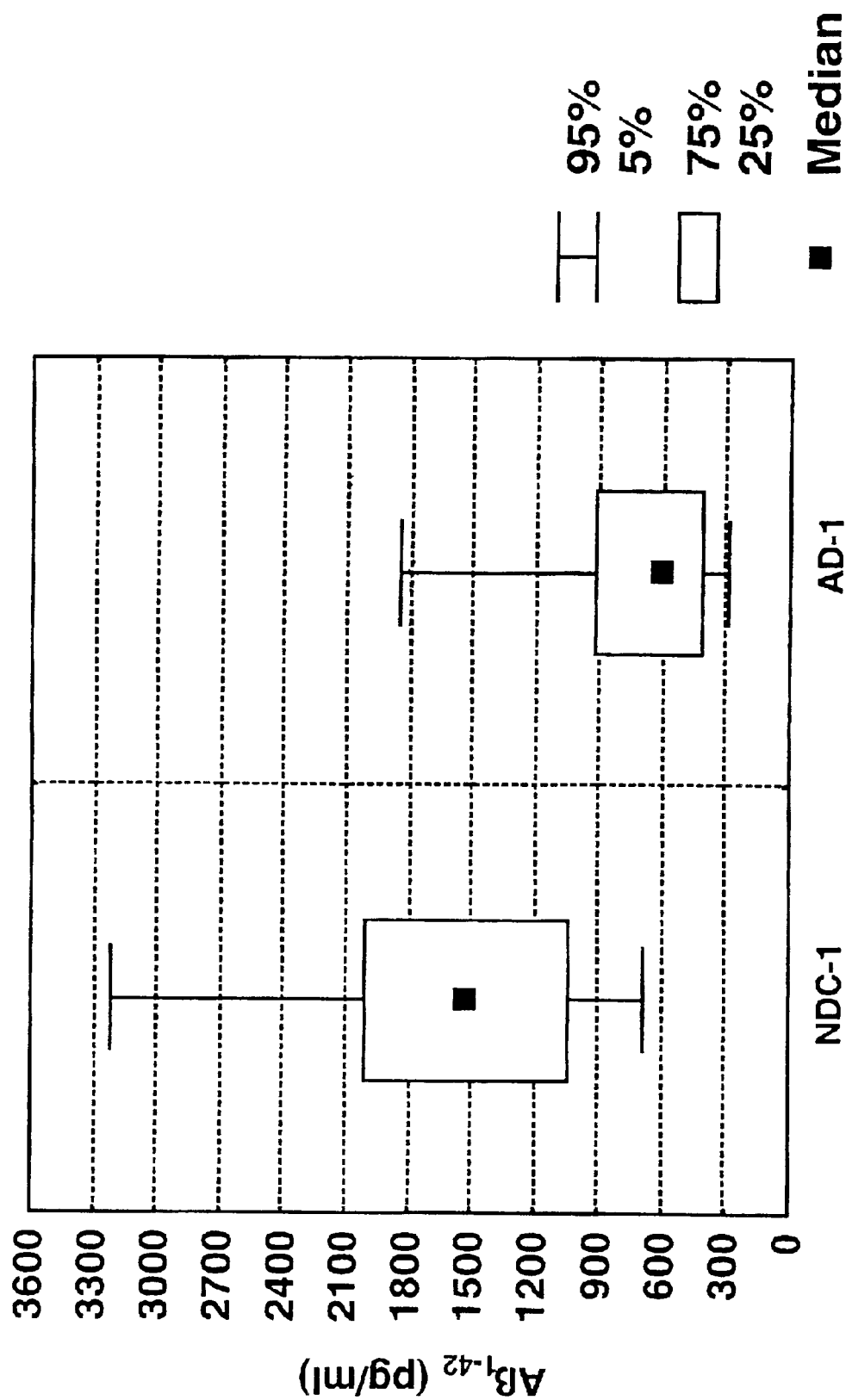
FIG. 4: a plot of Aβ1-42 in CSF in the NDC-1 and AD-1 patient groups, determined by Aβ SDS-PAGE/immunoblot-1 and film evaluation by densitometry.
Figure 5:
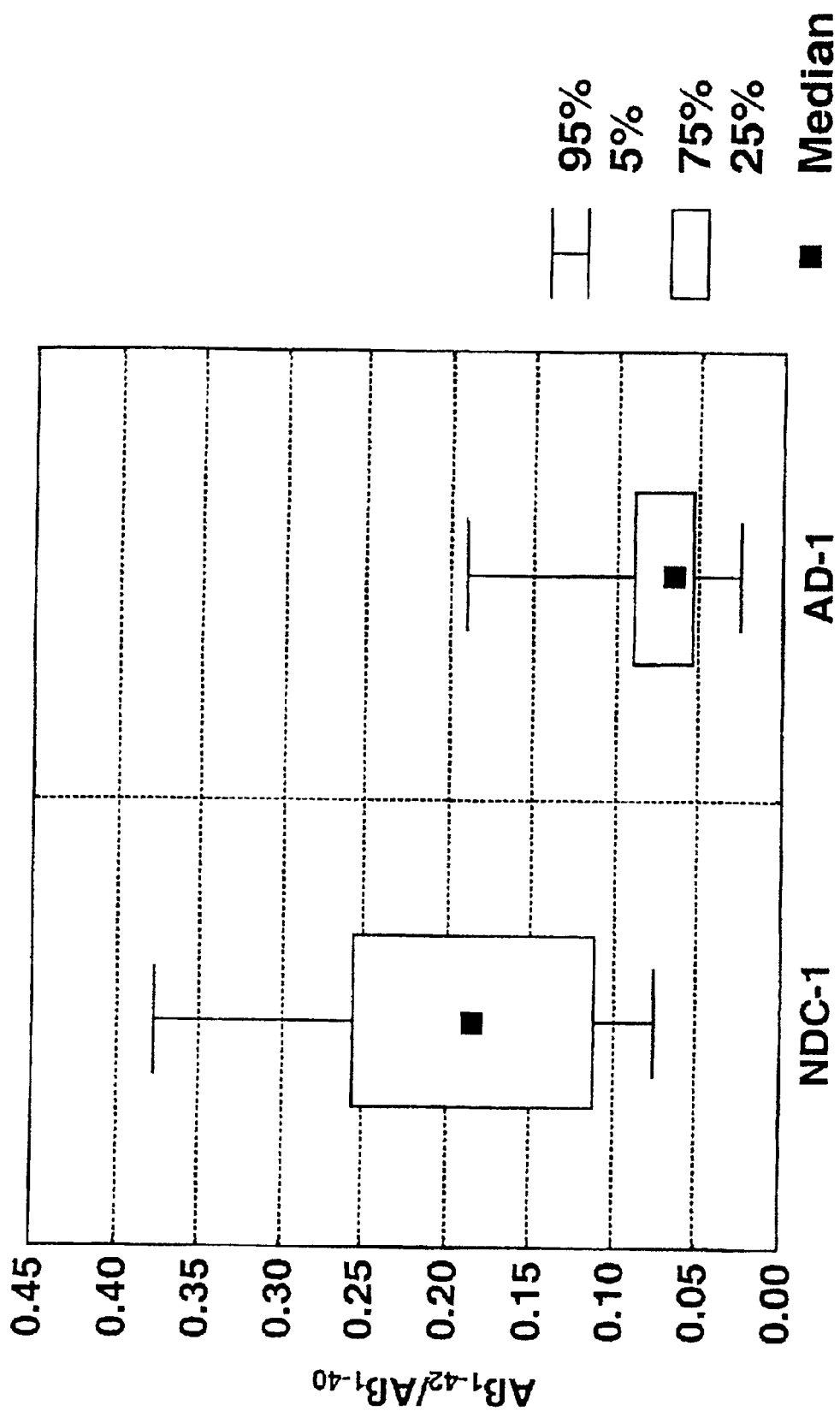
FIG. 5: a plot of the Aβ1-42/Aβ1-40 ratio in CSF in NDC-1 and AD-1, determined by Aβ SDS-PAGE/immunoblot 1 and film evaluation by densitometry.
Figure 6:
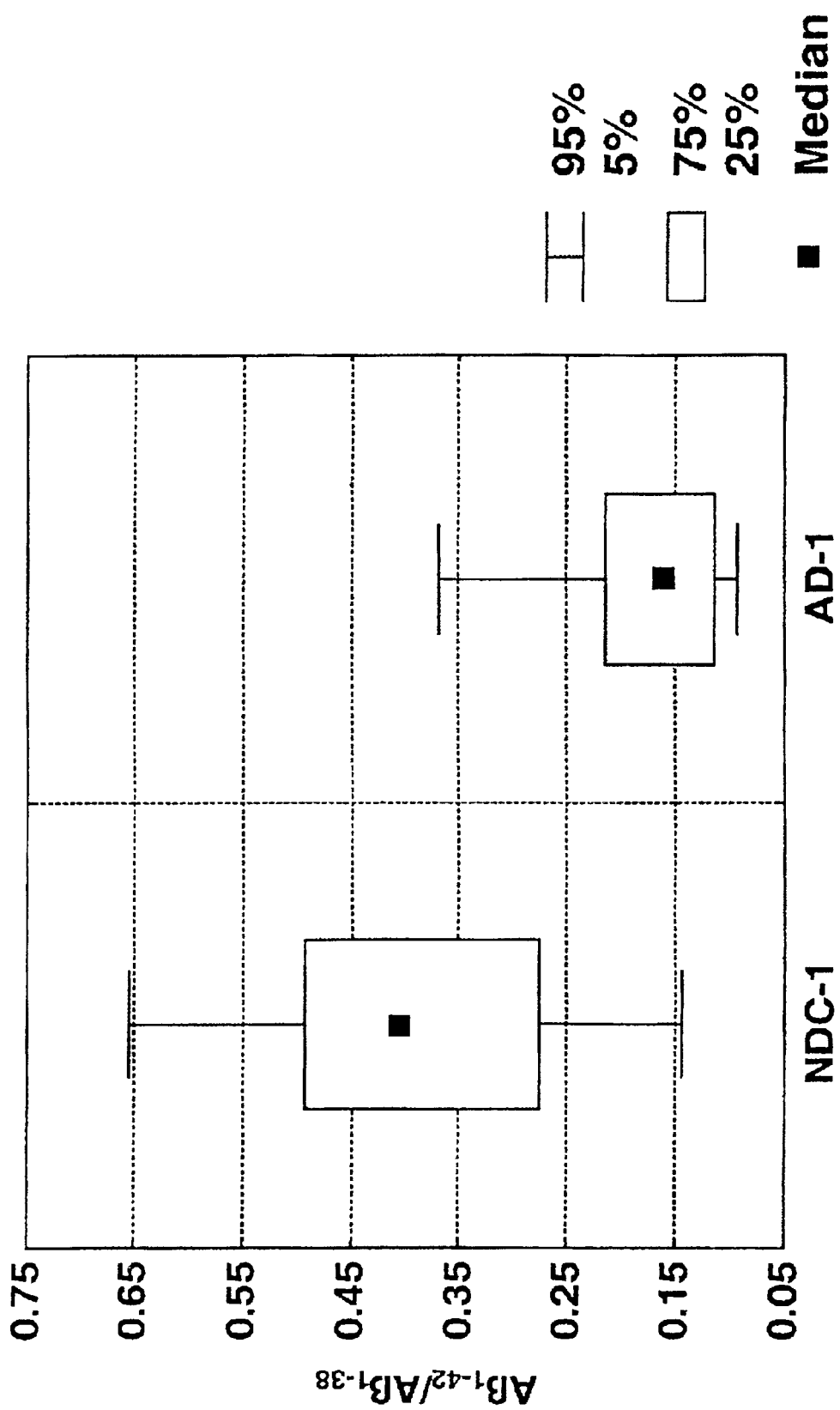
FIG. 6: a plot of the Aβ1-42/Aβ1-38 ratio in CSF in NDC-1 and AD-1, determined by Aβ SDS-PAGE/immunoblot 1 and film evaluation by densitometry.

The significant reduction in Aβ1-42 in human lumbar CSF in patients with AD-1 compared with NDC-1 is evident from FIG. 4. $A\beta_{1-40}$ is likewise significantly reduced in AD-1, but not to the extent evident for $A\beta_{1-42}$ (cf. table 14). Correspondingly, the $A\beta_{1-42}/A\beta_{1-40}$ ratio is also highly significantly reduced (FIG. 5, table 14). The likewise highly significant reduction in the $A\beta_{1-42}/A\beta_{1-38}$ ratio has not been described to date (FIG. 6, table 14). The limits for the AD-3 versus NDC-3 group comparison were found for $A\beta_{1-42}$ and the two latter Aβ peptide ratios via the respective "receiver operating characteristics (ROC)" (table 15). It was possible to differentiate the AD-1 versus NDC-1 groups of patients with a limit of 802.5 pg/ml $A\beta_{1-42}$ with a specificity of 74% and a sensitivity of 87%. The $A\beta_{1-42}/A\beta_{1-40}$ ratio has a diagnostic specificity of 71% and a sensitivity of 93% for differentiating the AD-1 versus NDC-1 groups. The corresponding specificity and sensitivity for the $A\beta_{1-42}/A\beta_{1-38}$ ratio is 84% and 0.86%.

Figure 7:
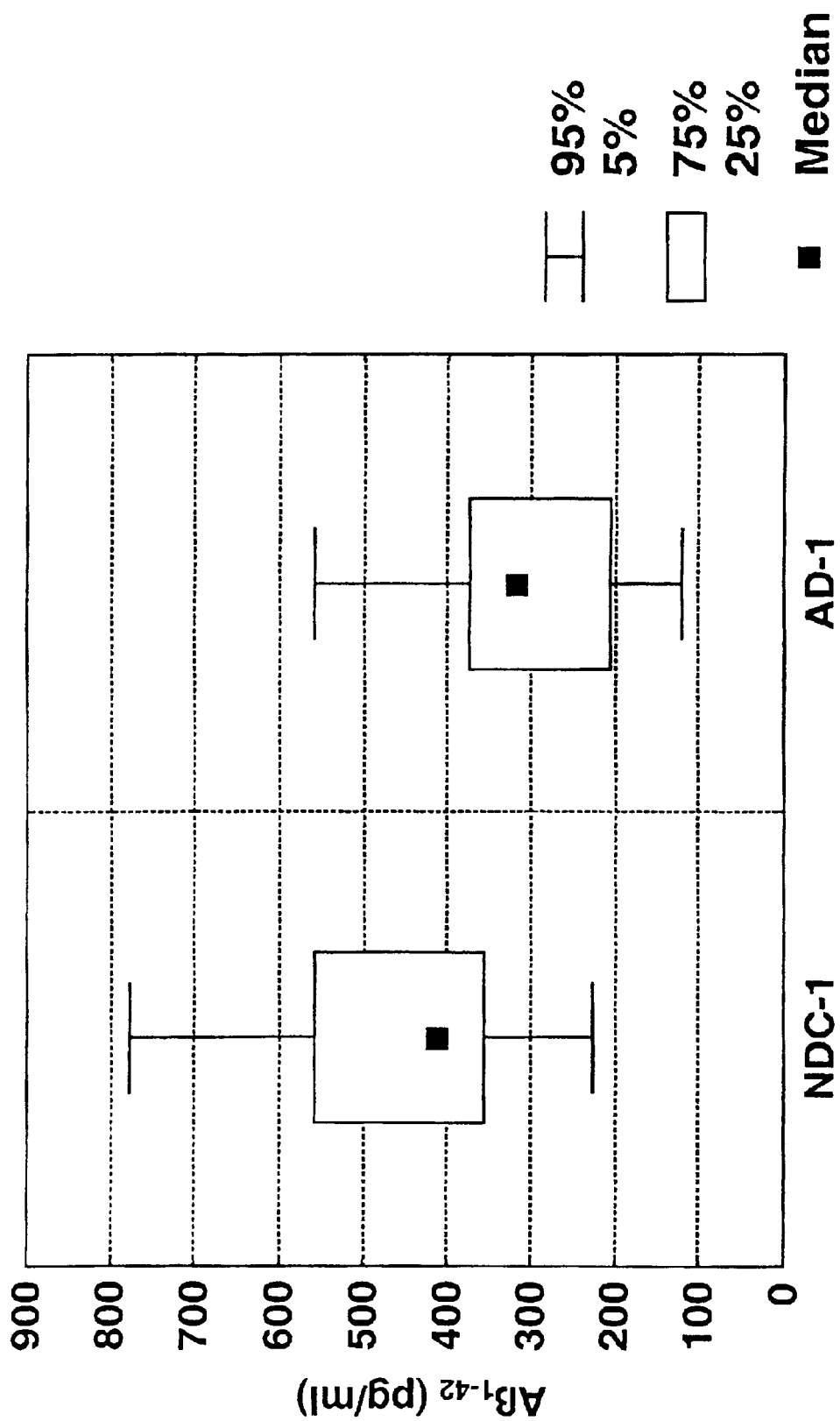
FIG. 7: a plot of a Aβ1-42 in CSF in NDC-1 and AD-1, determined by immunoprecipitation (IP without detergent, mAb 6E10) and Aβ SDS-PAGE/immunoblot 1 with film evaluation by densitometry.

$A\beta_{1-42}$ was investigated comparatively after immunoprecipitation (IP without detergent, mAb 6E10) and Aβ SDS-PAGE/immunoblot 1 with densitometric evaluation of films. As is evident from FIG. 7 and table 14, the differentiation by $A\beta_{1-42}$ of the AD-1 and NDC-1 groups of patients is less good after previous IP. The $A\beta_{1-42}$ concentration found in the CSF after immunoprecipitation and Aβ SDS-PAGE/immunoblot 1 with densitometric evaluation of films in a subgroup of patients with AD-1 agrees well with the concentration found using the commercial ELISA$A\beta_{1-42}$ (Hulstaert et al., 1999) in AD-1 (table 13). At the same time, the ELISA average in AD-1 (412 pg/ml) agrees well with the ELISA medians in AD (428 and 487 pg/ml) found in an international multicenter study (Hulstaert et al., 1999).

Comparison of the concentrations of $A\beta_{1-42}$ in the CSF depending on the method of measurement (SDS/thermal denaturation with Aβ SDS-PAGE/immunoblot 1 versus immunoprecipitation with Aβ SDS-PAGE/immunoblot 1 or ELISA$_{A\beta 1-42}$) makes it clear that considerably more $A\beta_{1-42}$ can be extracted from the CSF by SDS/thermal denaturation than by the antibody-dependent methods (immunoprecipitation and ELISA). The $A\beta_{1-42}$ concentrations in the CSF measured in AD after SDS/thermal denaturation are on average 2.3 times higher compared with immunoprecipitation (IP without detergent, mAb 6E10) and 1.8 times higher compared with the ELISA (without detergent). It is shown hereinafter that this difference between ELISA and Aβ SDS-PAGE/immunoblot is even higher in NDC patients (cf. NDC-3).

4.2.2 NDC-3 and AD-3

Table 19 gives the clinical data and individual measurements for the patients and table 20 summarizes the statistical characteristics of the AD-1 and NDC-1 groups of patients. The CSF samples were analyzed by Aβ SDS-PAGE/immunoblot 2 and CCD camera.

4.2.2.1 Dependence of the Aβ Peptide Concentration in the CSF on the Mode of Sample Preparation CSF aliquots from five patients in the NDC-3 group were investigated comparatively with previous immunoprecipitation (RIPA-IP, mAb 1E8) and with direct taking up of samples (SDS/thermal denaturation) (cf. table 20). The Aβ peptide concentrations resulting after SDS/thermal denaturation are somewhat higher. This effect is marked for $A\beta_{1-38}$ and $A\beta_{1-42}$ but does not reach the level of significance. Accordingly, comparable Aβ peptide levels are measured in CSF with both methods of sample pretreatment when the immunoprecipitation is carried out with detergents. In contrast thereto, the level of $A\beta_{1-42}$ measured in 27 of the NDC-3 patients is about 3 times lower with the commercial ELISA$A\beta_{1-42}$ (without detergent) compared with SDS/thermal denaturation and Aβ SDS-PAGE/immunoblot 2 with CCD camera.

It has been demonstrated hereinbefore (cf. 4.2.1) for patients in the AD-1 group that when the immunoprecipitation is carried out without detergent the measured concentrations are distinctly lower with immunoprecipitation (mAb 6E10) and Aβ SDS-PAGE/immunoblot 1 and comparable with the ELISA$A\beta_{1-42}$.

This indicates that $A\beta_{1-42}$ is present in human CSF in a fraction which is only partly accessible to monoclonal antibodies without previous treatment with detergents.

The detergents employed are able to release peptides from noncovalent protein-peptide bindings—for example caused by hydrophobic interaction. Accordingly, the higher CSF levels of $A\beta_{1-42}$ after use of detergents (SDS-thermal denaturation, RIPA-IP) compared with methods not using detergents (IP without detergent, ELISA$A\beta_{1-42}$) are probably caused by high-affinity binding and epitope masking of $A\beta_{1-42}$ onto other proteins or Aβ peptide aggregates. As expected on use of detergents, the use of the ionic detergent SDS at relatively high concentrations (0.5% w/v) and temperature (95° C.) is even more efficient than the RIPA detergent mix.

It is demonstrated hereinafter that $A\beta_{1-42}$ is particularly sensitive to cryoprecipitation compared with $A\beta_{1-40}$, and shows a disease-specific difference in cryoprecipitation behavior in patients with AD and NDC (cf. 4.2.4). Synthetic $A\beta_{1-42}$, dissolved with comparable concentration in water, by contrast shows distinctly less cryoprecipitation. This makes it probable that the reduction caused by cryoprecipitation in $A\beta_{1-42}$ in human CSF derives predominantly from the aggregate-bound proportion of the peptide. In the case of comparatively hydrophobic aggregates—for example lipoprotein-containing complexes—a loss through cryoprecipitation would not be surprising. In this connection, it is shown hereinafter (4.2.4) that ε4-positive patients in the NDC-3CP group show a particularly high rate of CP-related reduction in $A\beta_{1-42}$ and have CSF levels which are approximately as low as ε4-positive AD-3CP patients. Approximately equally low $A\beta_{1-42}$ CSF levels are also demonstrated hereinafter for patients in the OND-3ε4plus and AD-3ε4plus groups.

4.2.2.2 Aβ Peptides in the Plasma

The Aβ peptide quintet was also detectable in the plasma by immunoprecipitation and Aβ SDS-PAGE/immunoblot with CCD camera. The plasma concentrations are 30 to 60-fold lower compared with the CSF, and each of the two compartments show specific patterns of percentage proportions of Aβ peptides. In particular, the $A\beta_{1-42}/A\beta_{1-38}$ ratio is CNS-specifically different: CSF 0.80 (0.79–0.92), plasma 1.70 (1.69–1.75); median (quartile).

Figure 8:
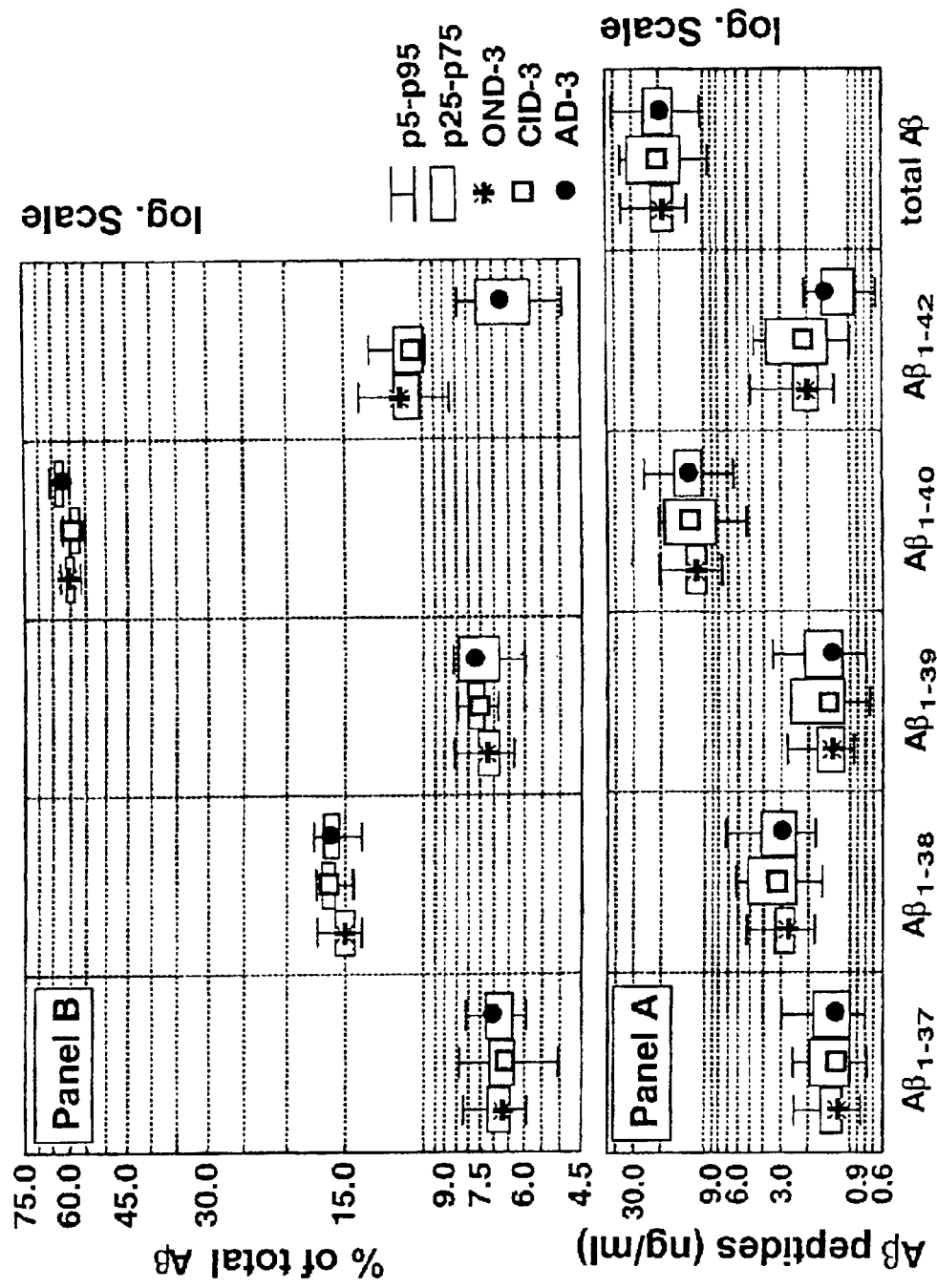
FIG. 8: a plot of Aβ peptide concentrations, determined by Aβ SDS-PAGE/immunoblot 2 in CSF in OND-3, CID-3 and AD-3.

4.2.2.3 Disease-Specific Aβ Peptide Patterns in the CSF and Effect of the ApoE Genotype FIG. 8 shows in section A the concentrations of the Aβ peptides 1-37/38/39/40/42 in human CSF in the OND-3, CID-3 and AD-3 groups of patients. Section B shows the proportion of the respective Aβ peptide species as a percentage of the total of all Aβ peptides. The logarithmic representation was chosen in order to be able to represent comparatively the distinct differences in CSF levels. It is noticeable with the CSF concentrations of the Aβ peptides that the second commonest Aβ peptide in human CSF after $A\beta_{1-40}$ is not $A\beta_{1-42}$ but $A\beta_{1-38}$. In addition, $A\beta_{1-42}$ is reduced in AD-3. The total Aβ peptide concentration in the investigated groups is substantially identical. On the other hand, considerably more distinct differences between the groups become clear on consideration of the percentage proportions of Aβ peptides:

CID-3 and AD-3 show increased proportions of $A\beta_{1-38}\%$ and $A\beta_{1-39}\%$ compared with OND-3

$A\beta_{1-40}\%$ is highly significantly increased in AD-3

$A\beta_{1-42}\%$ is highly significantly reduced in AD-3 and differentiates the AD patients distinctly better than the relevant Aβ peptide concentration.

It is known from the literature that there is often overexpression of $A\beta_{1-40}$ and $A\beta_{1-42}$ in familial forms of AD with APP point mutaions near the β-secretasese cleavage site, whereas with mutations near the γ-secretase cleavage site there is an increase in $A\beta_{1-42}$, and the $A\beta_{1-42}$ to $A\beta_{1-40}$ ratio increases markedly. It can therefore be assumed that disease-specific changes in γ-secretase activity can frequently be illustrated on consideration of the percentage proportions of the Aβ peptides.

Figure 9:
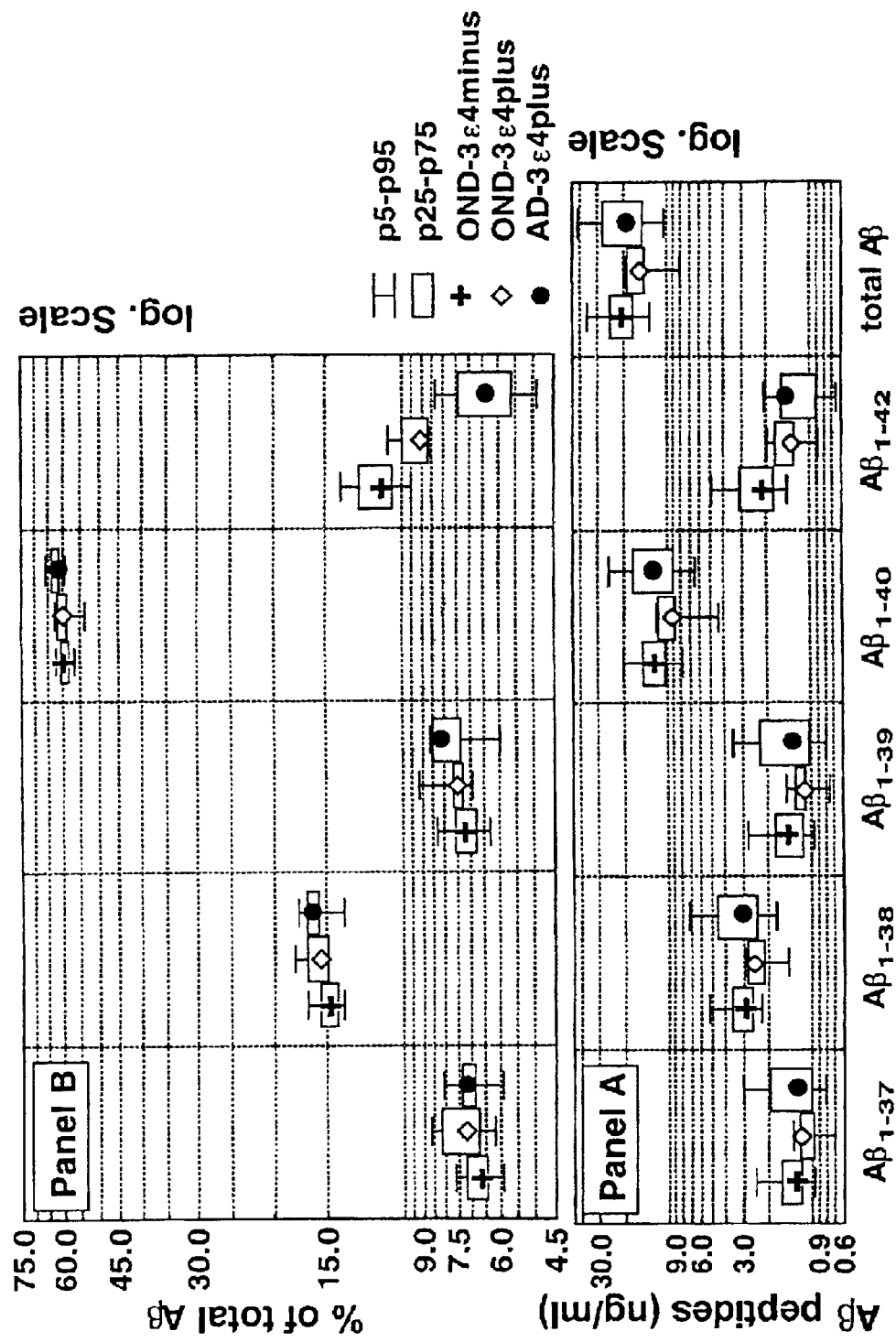
FIG. 9: a plot of Aβ peptide concentrations, determined by Aβ SDS-PAGE/immunoblot 2 in the CSF of patients in the OND-3 and AD-3 groups with one or two ApoE ε4 alleles (AD-3ε4plus, OND-3ε4plus), compared with OND-3 patients without the ApoE ε4 allele (ONDε4minus).

The subgroups OND-3ε4minus, OND-3ε4plus and AD-3ε4plus are compared in FIG. 9A and B as described under FIG. 8. It is thus possible to differentiate between ε4- and AD-dependent effects on the Aβ peptide pattern in the CSF. There is a tendency for all Aβ peptides to be reduced in the CSF in OND-3ε4plus compared with OND-3ε4minus, and correspondingly also the total Aβ peptide concentration (FIG. 9A). Within the Aβ peptide quintet, the reduction in $A\beta_{1-42}$ is particularly marked. On the other hand, there is a selective reduction in $A\beta_{1-42}$ in AD-3ε4plus, although to the same extent as in OND-3ε4plus. The total amount of Aβ peptides is not reduced in this case (FIG. 9A). It is thus not possible for the ε4-positive NDC-3 patients to be separated from the ε4-positive AD-3 patients solely by determination of $A\beta_{1-42}$ in CSF. However, this is possible via the percentage proportions of Aβ peptides (FIG. 9B). Owing to the selective reduction in $A\beta_{1-42}$ in AD-3ε4plus, the reduction in $A\beta_{1-42}\%$ is particularly large in this case, and the AD-3ε4plus group can be separated by this parameter without overlap from the OND-3ε4plus and OND-3ε4minus groups. At the same time, the percentage proportion of $A\beta_{1-40}$ is increased particularly greatly in AD-3ε4plus.

Figure 10:
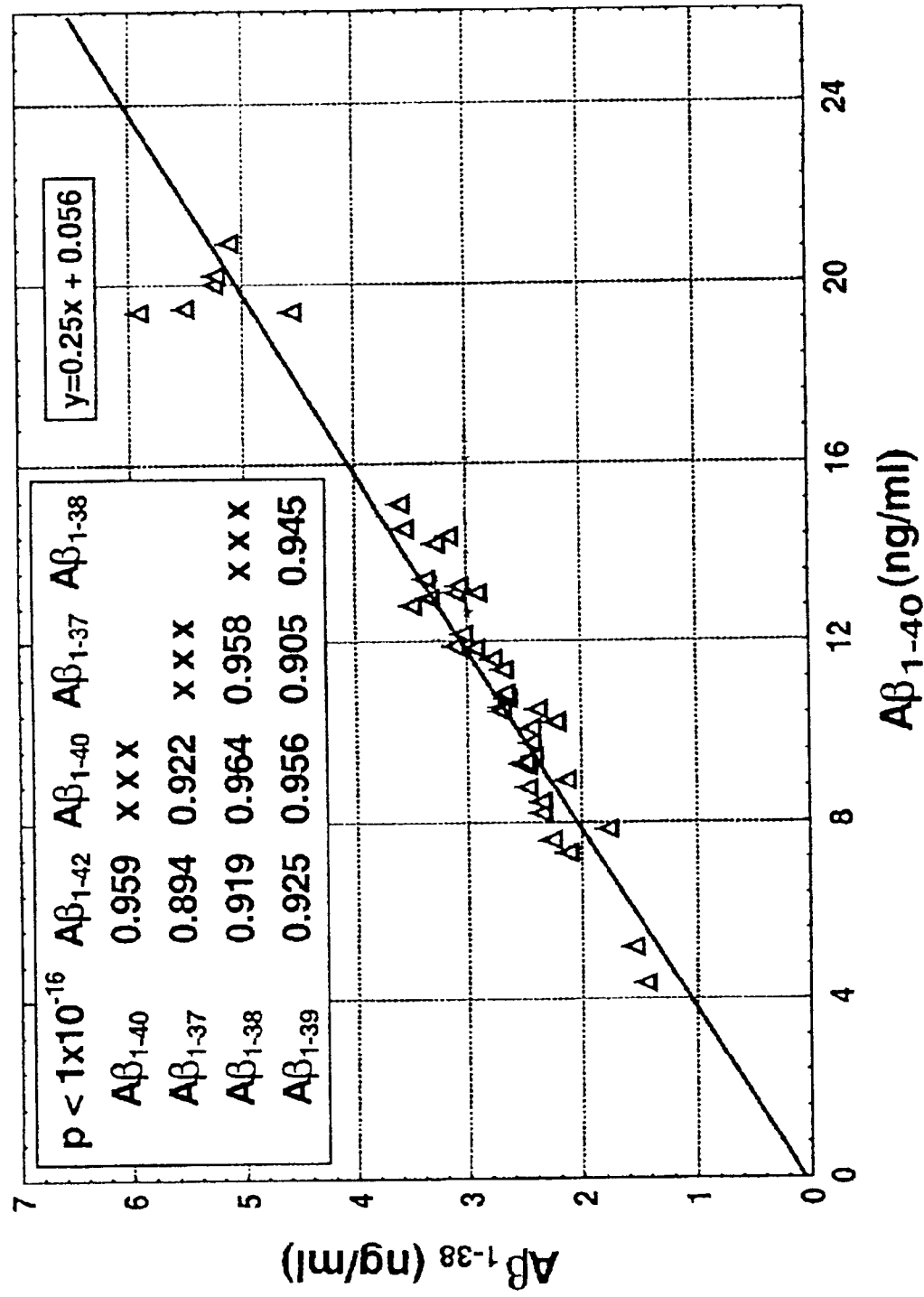
FIG. 10: a correlation of Aβ-38 and Aβ1-40 in CSF in NDC-3 and a correlation matrix of the Aβ peptides

As is evident from the correlation matrix in FIG. 10, the Aβ peptide quintet in the CSF is closely correlated with one another, and the percentage proportions of the Aβ peptides and their total concentration have astonishingly low coefficients of variation for biological parameters. These findings suggest that there is a tight enzymatic regulation of the concentration of the five Aβ peptides by β- and γ-secretase. In this connection, it is demonstrated hereinafter (4.5.2) that, besides $A\beta_{1-40}$ and $A\beta_{1-42}$, there is a particularly pronounced reduction in the production of carboxy-terminally truncated Aβ peptides by synthetic inhibitors of β- and γ-secretase.

4.2.2.4 Disease-Specific Patterns of Percentage Proportions of Aβ Peptides: Description of Individual Cases in the Groups of Patients It can be inferred from FIGS. 11–13 that patients with AD-3 and CID-3 can be differentiated from OND-3 patients via $A\beta_{1-38}\%$, $A\beta_{1-40}\%$ and $A\beta_{1-42}\%$.

Figure 11:
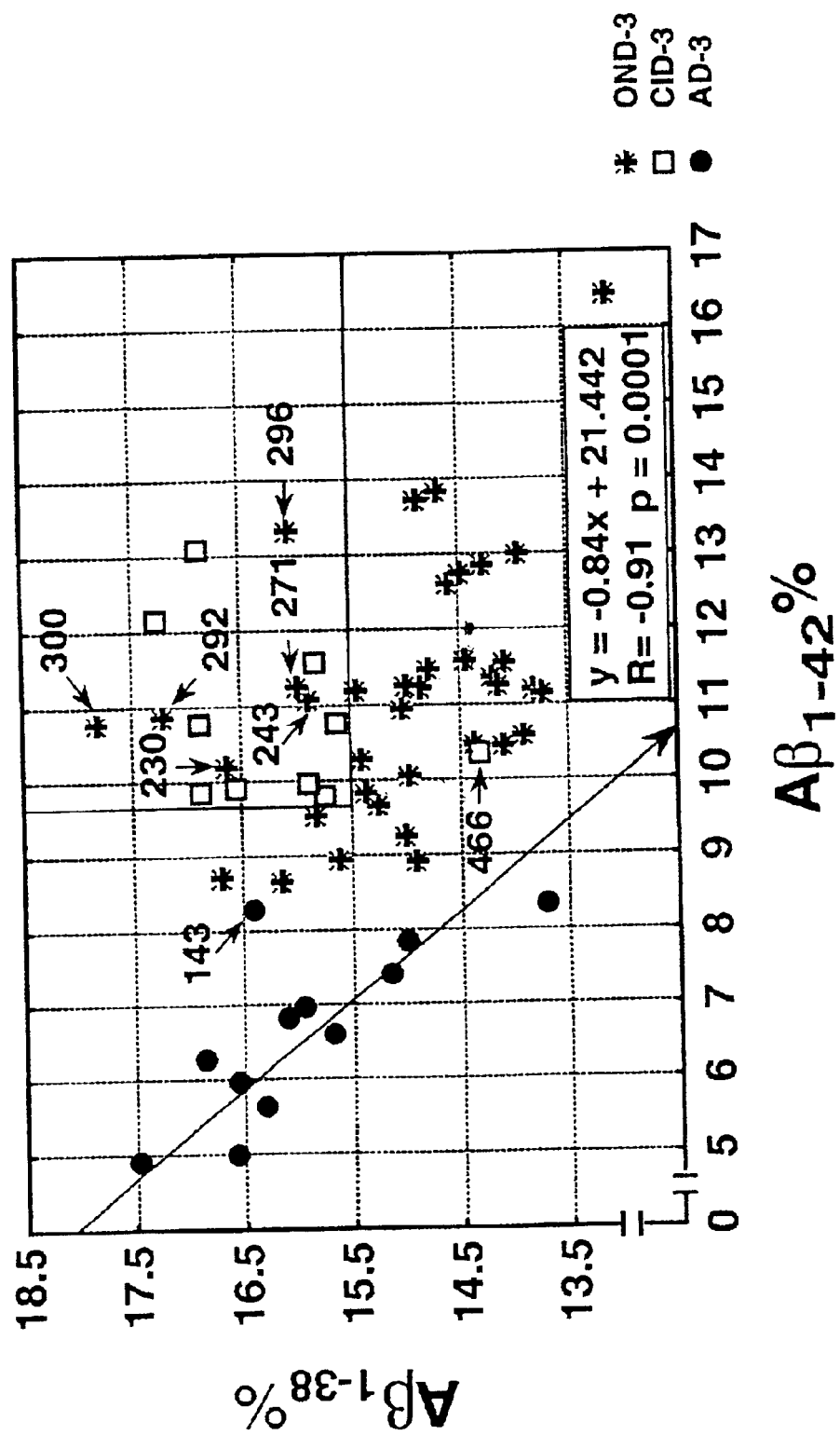
FIG. 11: a plot of Aβ1-38% versus Aβ1-40% in CSF in OND-3, CID-3 and AD-3. The regression line relates to the AD-3 group. The severity of the dementia increases in the direction of the arrow. The limit lines (Aβ1-38%=15.5, Aβ1-42%=9.6) relate to the CID-3 group. Individual patients are identified by their code numbers.

FIG. 11 demonstrates a significant negative correlation between $A\beta_{1-38}\%$ and $A\beta_{1-42}\%$ for AD-3 patients. The AD-3 patient 143 was not included in the calculation of the regression line and is identified here, as also hereinafter (cf. FIGS. 12 & 13), as an outlier. This patient showed clinically an early stage of AD (MMSE 27/30). A depressive pseudodementia had been discussed in the differential diagnosis in the history.

The severity of the dementia increases in the direction of the tip of the arrow on the regression lines. The association between the percentage proportions of Aβ peptides and the severity of the dementia will be dealt with in more detail hereinafter (cf. FIGS. 14 & 15). With a concentration limit of $A\beta_{1-42}\%=8.5$ it is possible to separate the AD-3 group from the CID-3 and OND-3 groups without overlap. The specific association between $A\beta_{1-38}\%$ and $A_{1-42}\%$ in AD suggests, however, that patients with AD can be differentiated even better by a function similar to the regression line between $A\beta_{1-38}\%$ and $A\beta_{1-42}\%$. This has direct relevance for neurochemical diagnosis of AD, since, for example, a patient with $A\beta_{1-42}\%=9.5$ would still be diagnosed as AD via the regression line as limit line if, at the same time, his value for $A\beta_{1-38}\%$ is 13.5, as predicted by the regression line (cf. FIG. 11). A corresponding statement applies to the association, shown hereinafter, between the $A\beta1-30/A\beta_{1-40}$ and $A\beta_{1-42}/A\beta_{1-38}$ ratios (FIG. 16). The concentration limits for differentiating the CID-3 group are: $A\beta_{1-38}\%=15.5$ and $A\beta_{1-42}\%=9.6\%$. Six patients are incorrectly classified as CID-3 in this way. These patients are identified by their coding. It is noteworthy that on detailed analysis of the clinical findings for some of these patients (3/6) retrospectively a chronic inflammatory process becomes probable.

Figure 12:
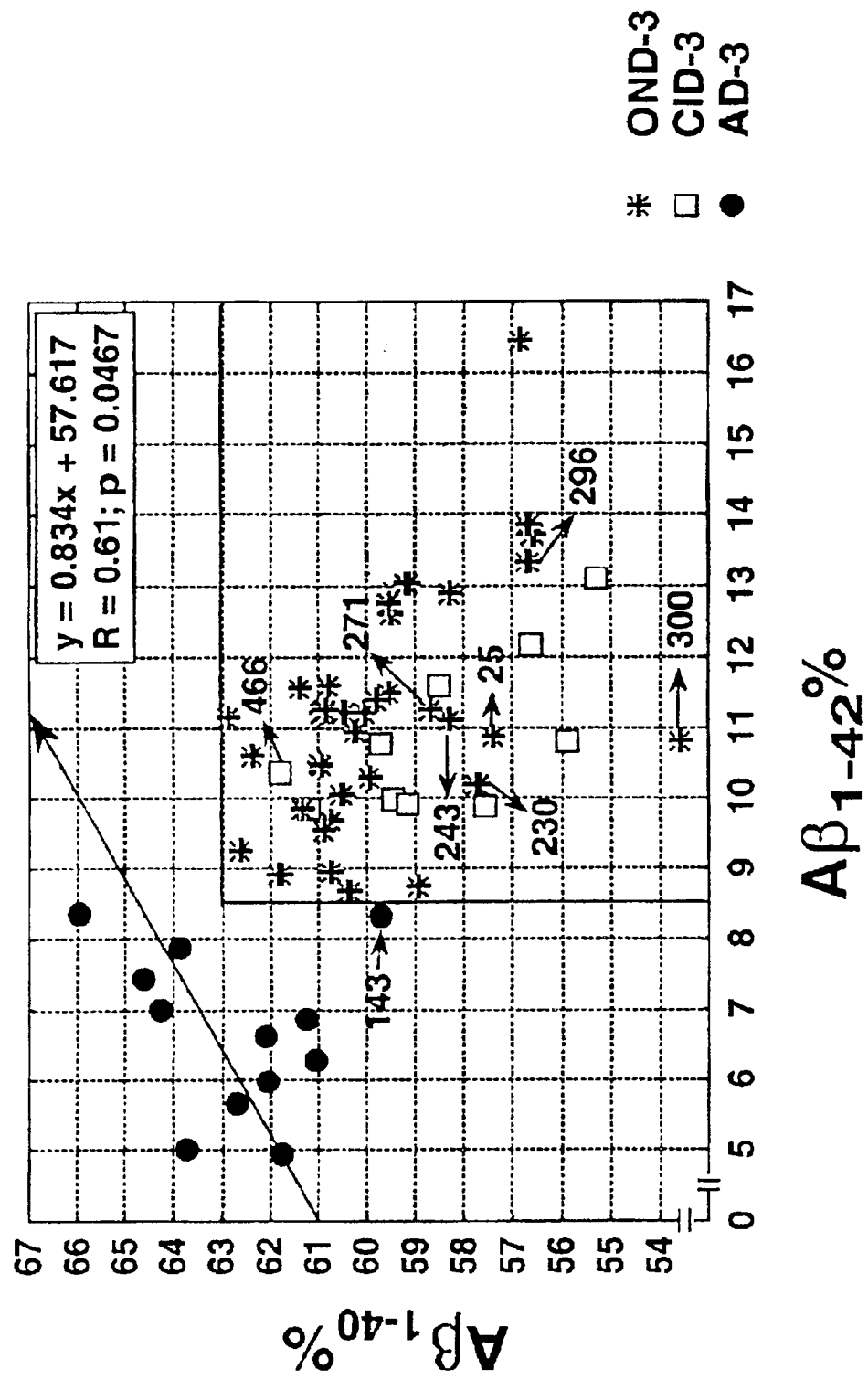
FIG. 12: a plot of Aβ1-40% versus Aβ1-42% in CSF in OND-3, CID-3 and AD-3. The regression line relates to the AD-3 group. The severity of the dementia increases in the direction of the arrow. The limit lines (Aβ40%=63.0, Aβ42%=8.5) relate to the AD-3 group. Individual patients are identified by their code numbers.

FIG. 12 shows $A\beta_{1-40}\%$ as a function of $A\beta_{1-42}\%$. Although an AD-specific correlation between these parameters is significant (without patient 143), it is less close. The severity of the dementia increases in the direction of the arrow.

The concentration limits for AD-3 are: $A\beta_{1-40}\%=63$ and $A\beta_{1-42}\%=8.5$.

Figure 13:
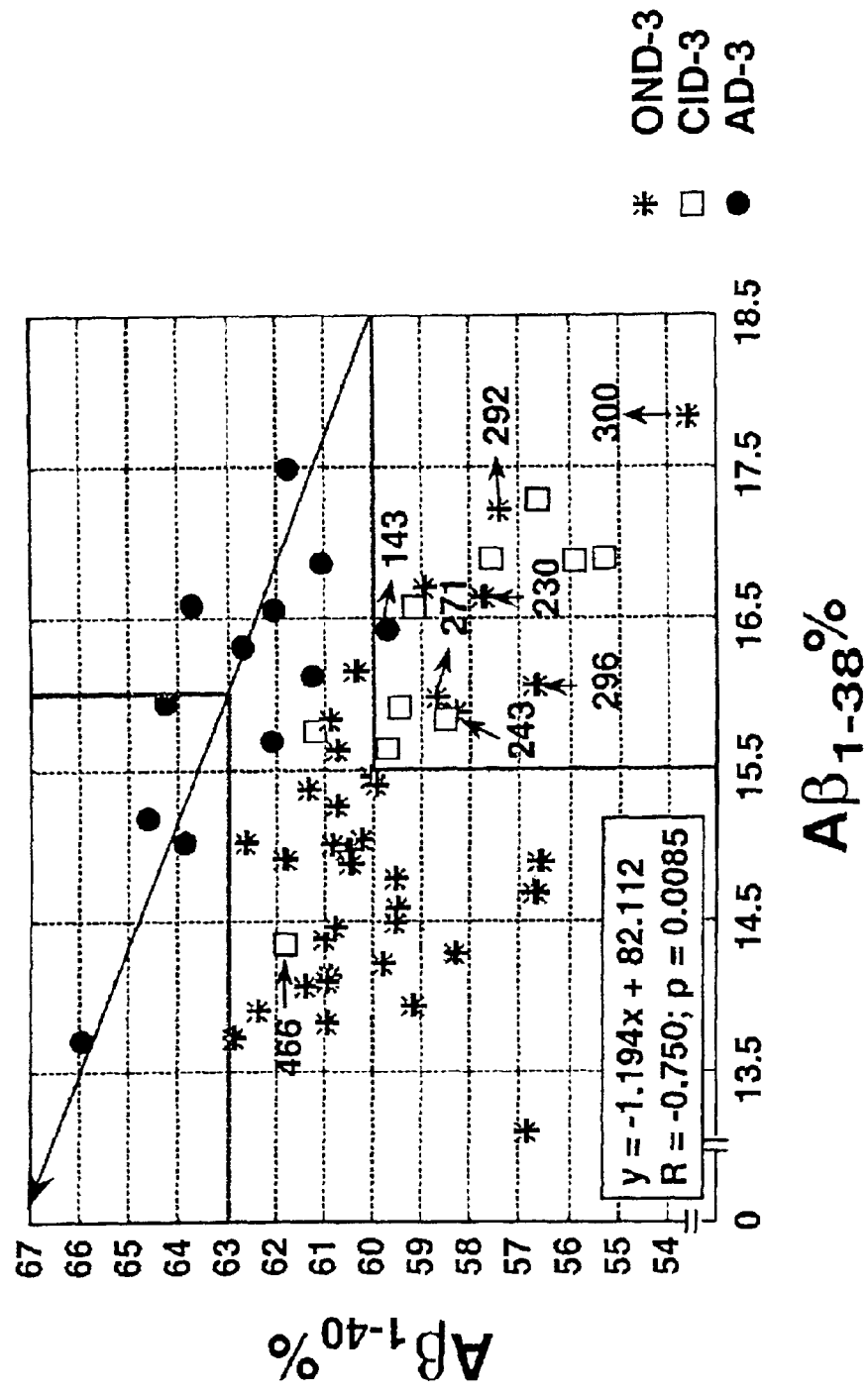
FIG. 13: a plot of Aβ1-40% versus Aβ1-38% in CSF in OND-3, CID-3 and AD-3. The regression line relates to the AD-3 group. The severity of the dementia increases in the direction of the arrow. The limit lines (Aβ38%=15.5, Aβ40%=60.0) relate to the CID-3 group. The broken limit lines (Aβ38%=16.0, Aβ40%=63.0) identify AD-3 patents with severe dementia. Individual patients are identified by their code numbers.

FIG. 13 shows $A\beta_{1-40}\%$ as a function of $A\beta_{1-38}\%$.

The limit lines $A\beta_{1-38}\%=15.5$ and $A\beta_{1-40}\%=60.0$ relate to the CID-3 group. An AD-specific correlation between these parameters is significant (without patient 143). The severity of the dementia increases in the direction of the arrow. The limit lines $A\beta_{1-38}\%=16.0$ and $A\beta_{1-40}\%=63$ define AD-3 patients with severe dementia. It is noteworthy here that no NDC-3 patient is above $A\beta_{1-40}\%=63$ and the intercept of this limit line with the regression line simultaneously predicts the limit line $A\beta_{1-38}\%=16$.

Figure 14:
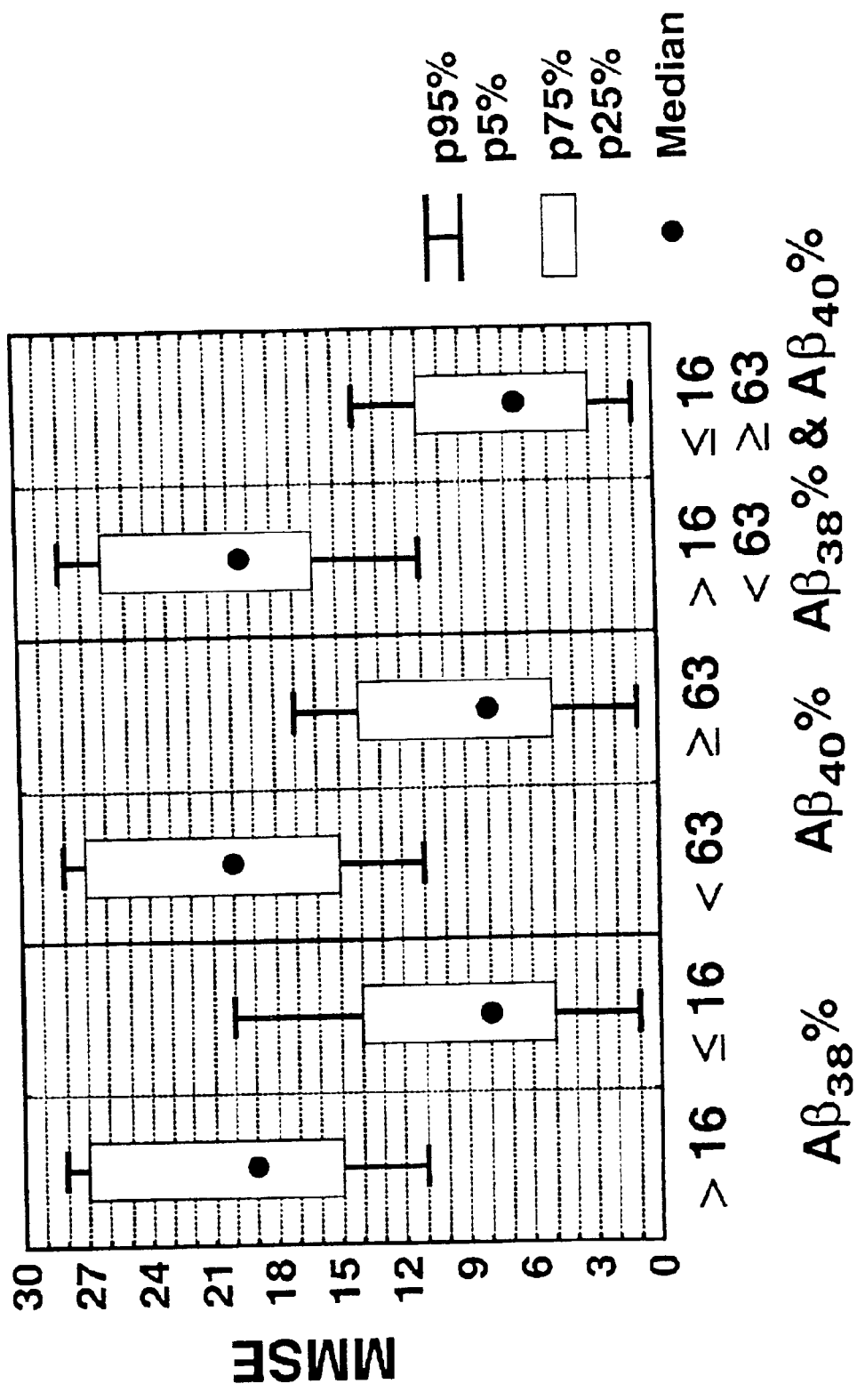
FIG. 14: a box plot of the MMSE examination results in CSF in AD-3 as a function of the proportions of Aβ peptides as percentages of the total Aβ peptide concentration.

It is clear from FIG. 14 that AD-3 patients with $A\beta_{1-38}\%<16.0$ or $A\beta_{1-40}\%>63$ mainly show severe dementia (MMSE≦10), otherwise the severity of the dementia is intermediate to mild (MMSE>10). This association is particularly marked in patients with values simultaneously below and above the two limits (FIG. 14; cf. also FIG. 13).

Figure 15:
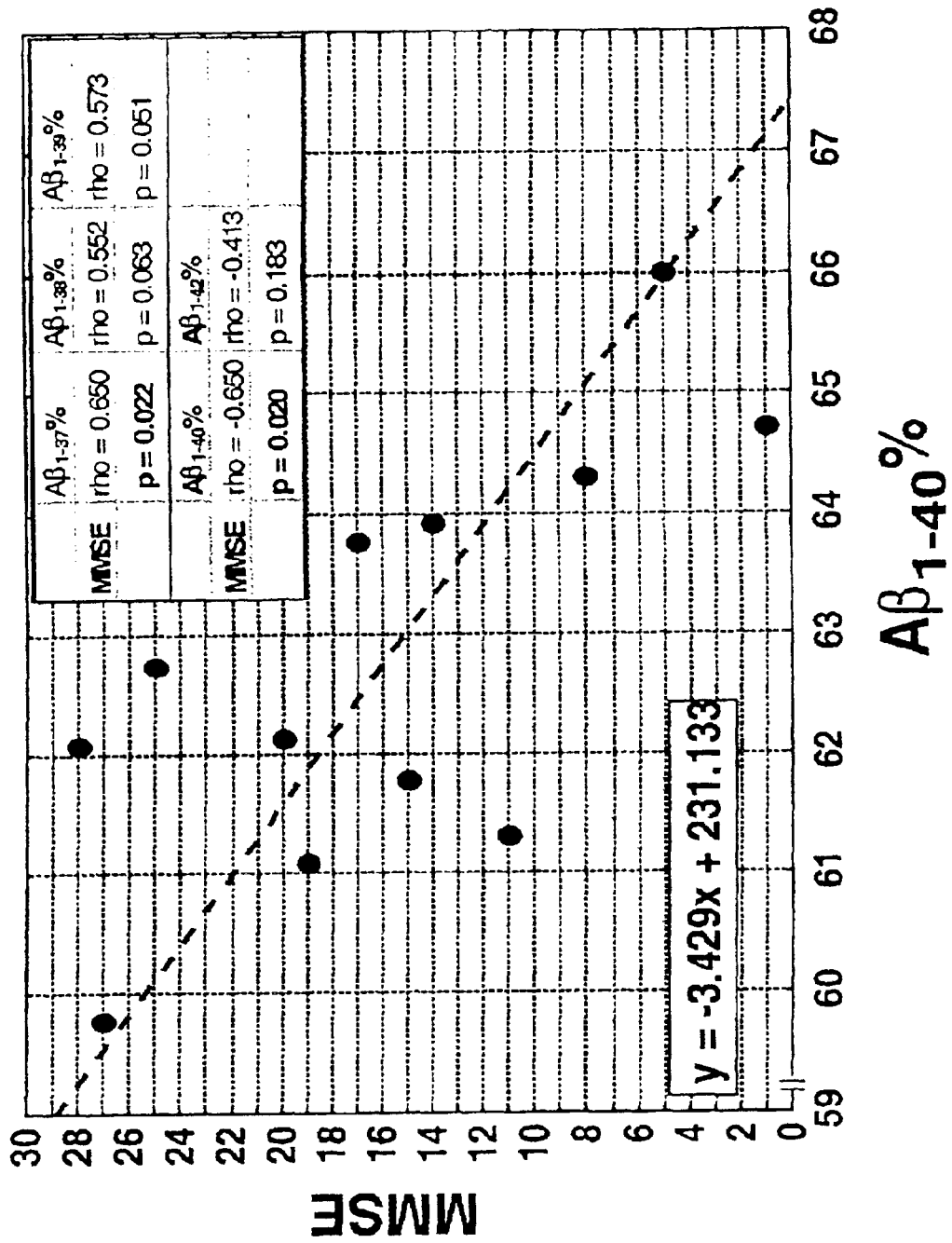
FIG. 15: MMSE examination result as a function of the proportion of Aβ peptide in the CSF as a percentage of the total Aβ peptide concentration in AD-3.
Figure 16:
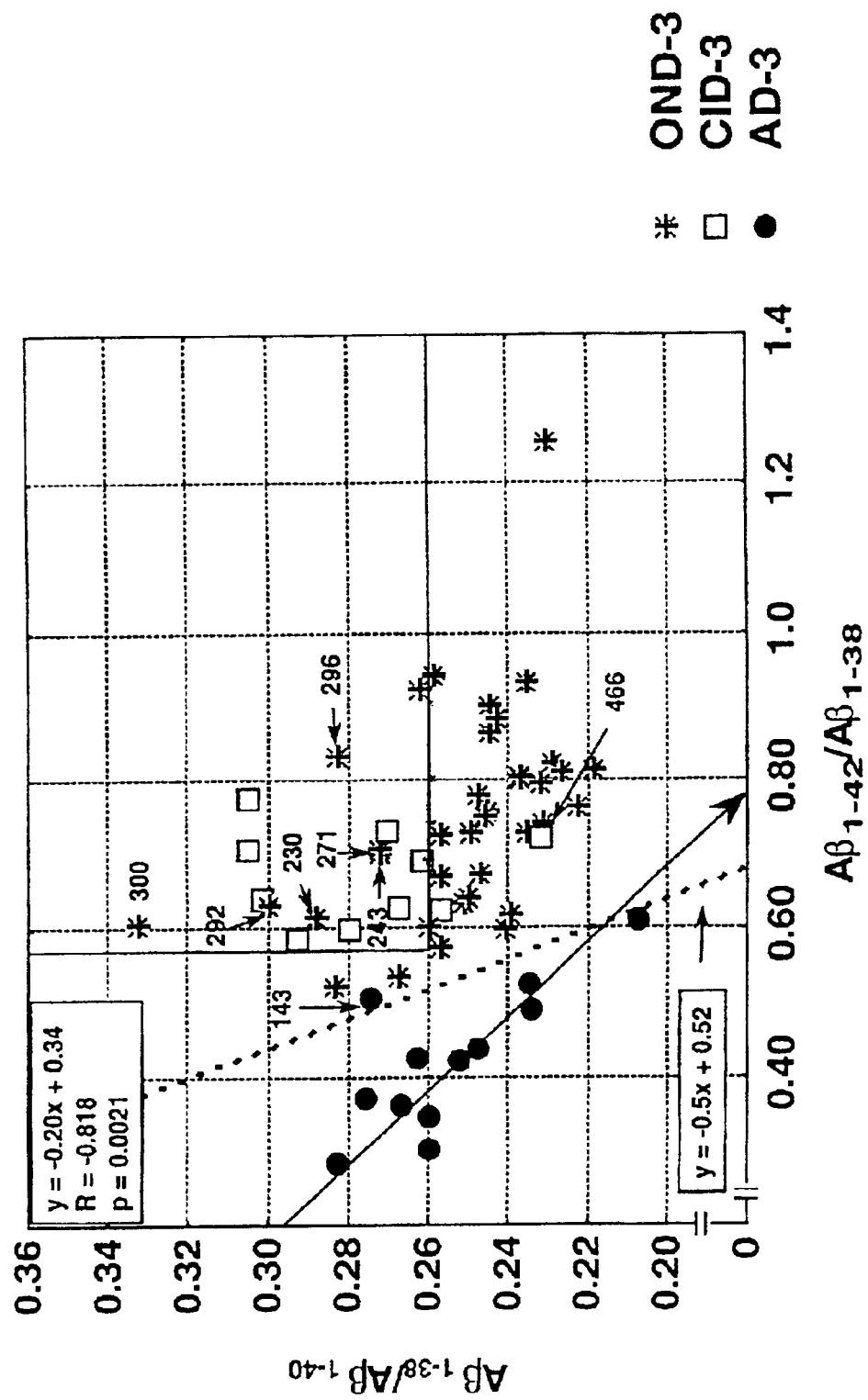
FIG. 16: a plot of Aβ1-38/Aβ1-40 versus Aβ1-42/Aβ1-38 in CSF in OND-3, CID-3 and AD-3. The regression line relates to the AD-3 group. The broken limit line is a parallel to the regression line. The severity of the dementia increases in the direction of the arrow. The limit lines (Aβ1-38/Aβ1-40=0.26, Aβ1-42/Aβ1-38=0.57) relate to the CID-3 group. Individual patients are identified by their code numbers.

The correlation matrix for the association between the percentage proportions of Aβ peptides and severity of the dementia is shown in FIG. 15. Significant associations are found for $A\beta_{1-37}\%$ and $A\beta_{1-40}\%$. It is noteworthy that the group of carboxy-terminally truncated Aβ peptides shows, in contrast to $A\beta_{1-40}\%$, positive correlation coefficients for the latter association. No significant association was found between the absolute concentrations of the Aβ peptides in the CSF and the severity of the dementia, i.e. once again disease-specific associations become clear only on examination of the percentage proportions of Aβ peptides.

4.2.2.5 Disease-specific Patterns of Aβ Peptide Ratios: Description of Individual Cases in the Groups of Patients The Aβ peptide ratios $A\beta_{1-38}/A\beta_{1-40}$, $A\beta_{1-42}/A\beta_{1-38}$ and $A\beta_{1-42}/A\beta_{1-40}$ allow differentiation between the AD-3, CID-3 and OND-3 groups. This has the advantage that it is now necessary to quantify only three Aβ peptides in order to differentiate the three groups of patients, but it leads to a certain loss of diagnostic separation efficiency. It is thus obvious to develop an ELISA triplet ($A\beta_{1-38}$, $A\beta_{1-40}$, $A\beta_{1-42}$) for the neurochemical diagnosis of dementia and identification of patients with chronic inflammatory CNS disorders. It was intended to combine this approach with a detergent-dependent sample preparation (cf. 4.2.4).

FIG. 16 shows $A\beta_{1-38}/A\beta_{1-40}$ as a function of $A\beta_{1-42}/A\beta_{1-38}$. There is a significant and specific association between these two parameters in AD. The severity of the dementia increases in the direction of the tip of the arrow of the regression line (cf. FIG. 18). Patient 143 is again identified as an outlier via the limit line $A\beta_{1-38}/A\beta_{1-40}=-0.5$ ($A\beta_{1-42}/A\beta_{1-38}$)+0.52. The other AD-3 patients are correctly classified and no NDC-3 patient is incorrectly assigned to the AD-3 group. The limit lines $A\beta_{1-38}/A\beta_{1-40}=0.26$ and $A\beta_{1-42}/A\beta_{1-38}=0.57$ relate to the CID-3 group.

Figure 17:
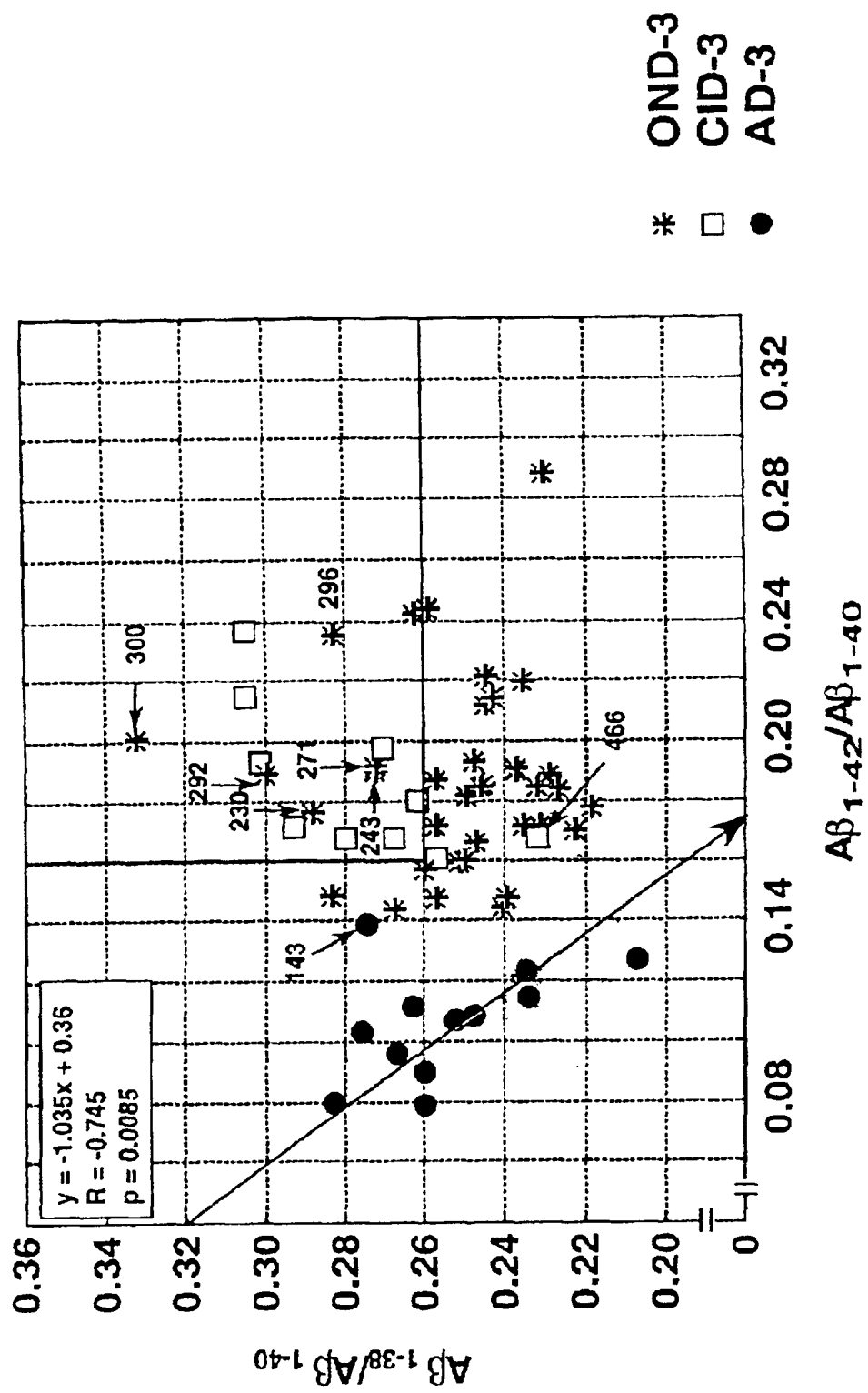
FIG. 17: a plot of Aβ1-38/Aβ1-40 versus Aβ1-42/Aβ1-40 in CSF in OND-3, CID-3 and AD-3. The regression line relates to the AD-3 group. The severity of the dementia increases in the direction of the arrow. The limit lines (Aβ1-38/Aβ1-40=0.26, Aβ1-42/Aβ1-40=0.16) relate to the CID-3 group. Individual patients are identified by their code numbers.

FIG. 17 shows $A\beta_{1-38}/A\beta_{1-40}$ as a function of $A\beta_{1-42}/A\beta_{1-40}$. There is a significant and specific association between these two parameters in AD. The severity of the dementia increases in the direction of the tip of the arrow of the regression line (cf. FIG. 18). All AD-3 patients are correctly classified via the limit line $A\beta_{1-42}/A\beta_{1-42}=0.14$ and no NDC-3 patient is incorrectly assigned to the AD-3 group. The limit lines $A\beta_{1-38}/A\beta_{1-40}=0.26$ and $A\beta_{1-42}/A\beta_{1-40}=0.16$ relate to the CID-3 group.

Figure 18:
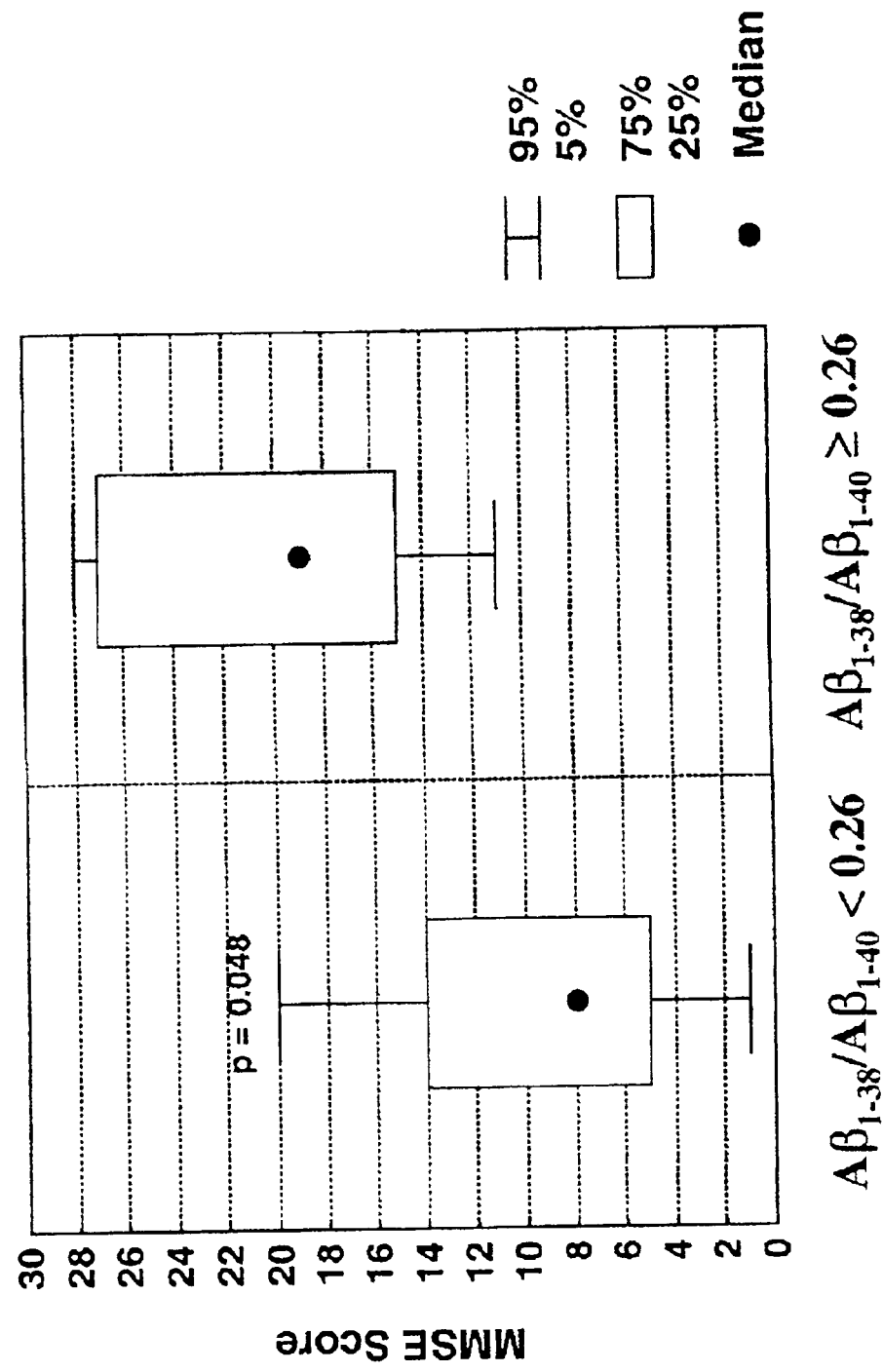
FIG. 18: a box plot of the MMSE examination results in CSF in AD-3 as a function of the Aβ1-38/Aβ1-40 ratio.

FIG. 18 makes it clear that AD-3 patients with an $A\beta_{1-38}/A\beta_{1-40}$ ratio of less than 0.26 on average show severe AD ((MMSE≦10), but otherwise show moderate to mild severity of the dementia (MMSE>10).

4.2.3 NDC-$2^{CP}$

The reduced $A\beta_{1-42}$ concentration in the CSF of patients with AD has to date been found in samples which had already been frozen previously. The first investigation therefore on patients in the NCD-$2^{CP}$ group was whether $A\beta_{1-42}$ in CSF is particularly sensitive to cryoprecipitation compared with other Aβ peptides. In this connection, freshly obtained CSF was divided into aliquots. One aliquot was frozen untreated at −80° C. The other aliquot was used to take up the SDS-SB which had been introduced as dry substance into Eppendorf sample vessels. This aliquot was frozen after SDS/thermal denaturation. Comparative analysis by Aβ SDS-PAGE/immunoblot 1 and densitometric evaluation of films then took place at least 24 hours after storage at −80° C. Ten neuropsychiatric control patients without Alzheimer's dementia were investigated. It was possible to determine $A\beta_{1-40}$ and $A\beta_{1-42}$ in nine of these patients. Evaluation only of $A\beta_{1-40}$ was possible in one patient.

Table 16a makes it clear that a proportion of the peptide is lost owing to cryoprecipitation, selectively accentuated for $A\beta_{1-42}$ with large interindividual variation. The percentage proportion of $A\beta_{1-42}$ which is lost in CSF frozen untreated when the cryoprecipitation is not reduced by pretreatment with SDS/thermal denaturation was calculated as follows:

$$\%\Delta A\beta_{1-42} = ([A\beta_{1-42}\text{native}]_{conc.} - [A\beta_{1-42}\text{SDS}]_{conc.})/[A\beta_{1-42}\text{SDS}] \text{ conc.} \times 100.$$

A value of "−10" for $\%\Delta A\beta_{1-42}$ means, for example, that $A\beta_{1-42}$ was reduced by 10% owing to cryoprecipitation through freezing of untreated CSF compared with the "protective" pretreatment with SDS/thermal denaturation. Since the samples could not be measured before the freezing, it cannot be ruled out that an additional proportion of $A\beta_{1-42}$ is lost in the samples due to cryoprecipitation and cannot be prevented even by pretreatment with SDS/thermal denaturation.

Table 16b makes it clear that $A\beta_{1-42}$ is reduced on average by about 30% owing to CP after freezing of untreated CSF ($\Delta A\beta 42\%$: −29.9±10.9, mean±SD; p=0.005). The maximum observed absolute and percentage declines in $A\beta_{1-42}$ are respectively −798.3 pg and −44.5%. The small decline in $A\beta_{1-40}$ ($\Delta A\beta 40\%$: −3.5±6.3; mean±SD; p=n.s.) is, on the other hand, not significant, but correspondingly the ratio $A\beta_{1-42}/A\beta_{1-40}$ ($\Delta A\beta 42/40\%$: −27.0±10.2; mean±SD; p=0.008).

4.2.4 NDC-$3^{CP}$ and AD-$3^{CP}$

It was subsequently investigated on the NDC-$3^{CP}$ and AD-$3^{CP}$ groups of patients whether disease-specific differences in the cryoprecipitation of $A\beta_{1-42}$ in CSF emerge. $A\beta_{1-42}$ in CSF was quantified by $A\beta$ SDS-PAGE/immunoblot 2 and CCD camera. The differential sample pretreatment took place as stated for the NDC-$2^{CP}$ group.

The concentrations of $A\beta_{1-42}$ as a function of the sample pretreatment are summarized for the two groups of patients in table 21.

Figure 19:
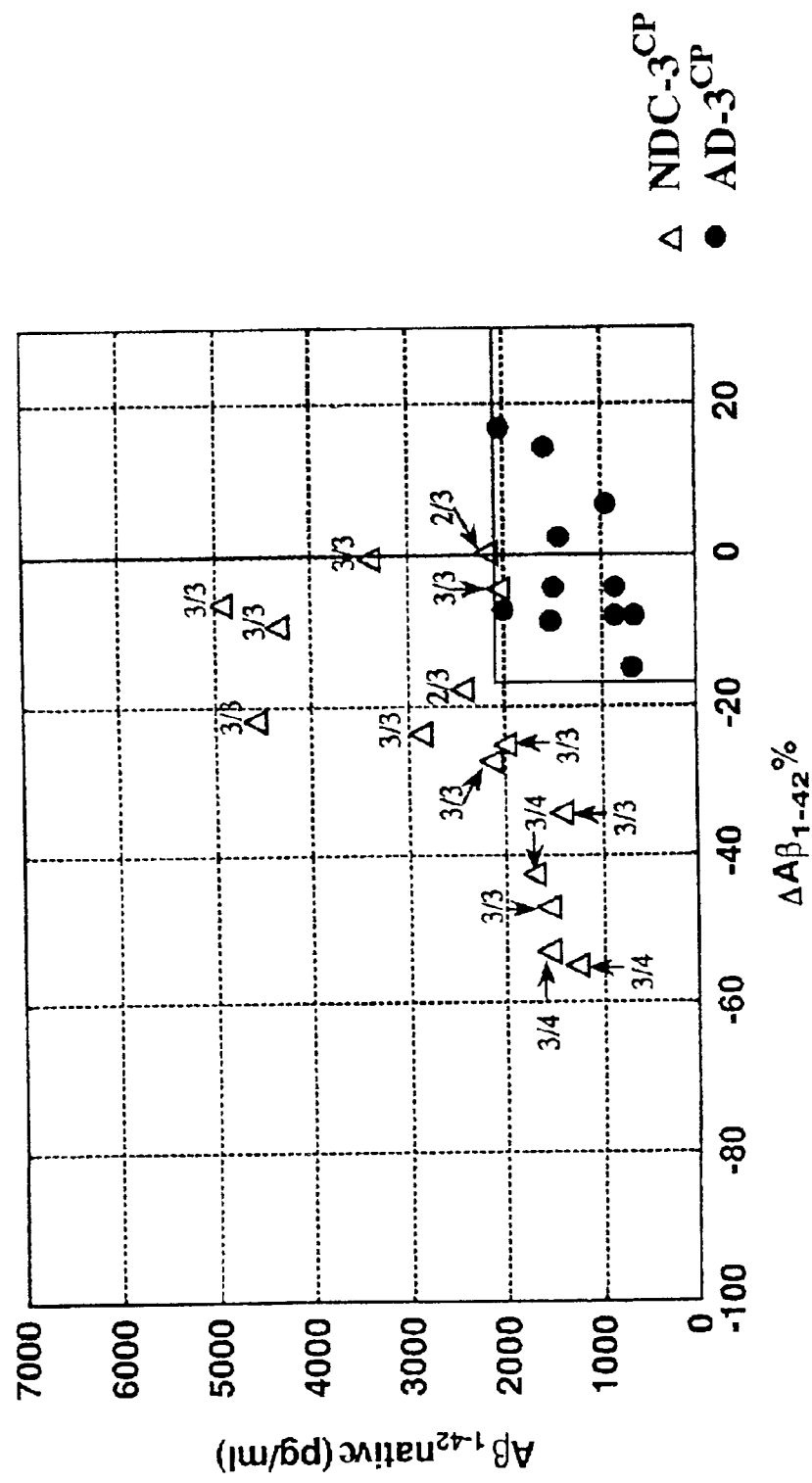
FIG. 19: a plot of Aβ1-42 native in CSF in NDC-3CP and AD-3CP versus ΔAβ1-42%, i.e. as a function of the reduction caused by cryoprecipitation in Aβ1-42. The limit lines (Aβ1-42=2100, ΔAβ1-42%=−17) relate to the AD-3CP group. The zero axis i.e. no reduction caused by cryoprecipitation in Aβ1-42, is indicated by a line. The ApoE genotype is indicated for the NDC-3CP patients. 9/11 of the AD-3CP patients had at least one ApoE ε4 allele. The ApoE ε4 genotype was unavailable for 2/11 of the AD-3CP patients.

FIG. 19 shows the concentrations of $A\beta_{1-42}$ after freezing untreated CSF as a function ($A\beta_{1-42}$native) of the cryoprecipitation. It was possible by determining $A\beta_{1-42}$ in frozen untreated CSF to separate the NDC-$3^{CP}$ and AD-$3^{CP}$ groups of patients significantly (p=0.0013). Nevertheless, FIG. 19 shows a clear overlap of the two groups of patients. According to this, 6/15 patients in the NDC-$3^{CP}$ group have $A\beta_{1-42}$ levels in the CSF below the concentration limit (2100 pg/ml) of the AD-$3^{CP}$ group. On the other hand, only one NDC-$3^{CP}$ patient is incorrectly assigned to the AD-3CP group when the concentration limit of $\Delta A\beta_{1-42}\%$ (−17% to −20%) is additionally taken into account. At the same time, all the patients in the AD-$3^{CP}$ group are correctly assigned.

The average reduction caused by cryoprecipitation in $A\beta_{1-42}$ is −24.6%±18.8 (mean±SD) in NDC-$3^{CP}$, which agrees well with the abovementioned data for the NDC-$2^{CP}$ patients (−29.9±10.9, mean±SD). It is again clear that there is a considerable interindividual variation in the extent of the reduction caused by cryoprecipitation in $A\beta_{1-42}$ in the CSF of NDC-$3^{CP}$ patients. The extent of the reduction caused by cryoprecipitation in $A\beta_{1-42}$ in NDC-$3^{CP}$ patients is apparently determined essentially be the presence of the ApoE $\epsilon 4$ allele; 3 patients of the 4 patients with the greatest reduction caused by CP in $A\beta_{1-42}$ ($\Delta A\beta_{1-42}\% < -40\%$) carry an ApoE $\epsilon 4$ allele (cf. FIG. 19).

By contrast, AD patients show a negligible reduction caused by cryoprecipitation in $A\beta_{1-42}$, and it is evident from FIG. 19 that the $\%\Delta A\beta_{1-42}$ values in this case are scattered around the zero axis (−1.6±10.2, mean±SD). Correspondingly, comparison of the NDC-$3^{CP}$ versus the AD-$3^{CP}$ group is significant for $\Delta A\beta_{1-42}\%$ (p=0.0025). It is noteworthy that reduction caused by CP in $A\beta_{1-42}$ is absent in AD-$3^{CP}$ although 9/11 patients are $\epsilon 4$-positive. The ApoE genotype of two AD-$3^{CP}$ patients is unknown. It is also noticeable that the levels of $A\beta_{1-42}$ in the CSF of AD-$3^{CP}$ and NDC-$3^{CP}$ patients with at least one $\epsilon 4$ allele are about equally low. This association was also clear hereinbefore on comparison of the levels of $A\beta_{1-42}$ in the CSF in the OND-$3\epsilon 4$plus and AD-$3\epsilon 4$plus groups (cf. 4.2.2.3).

Figure 20:
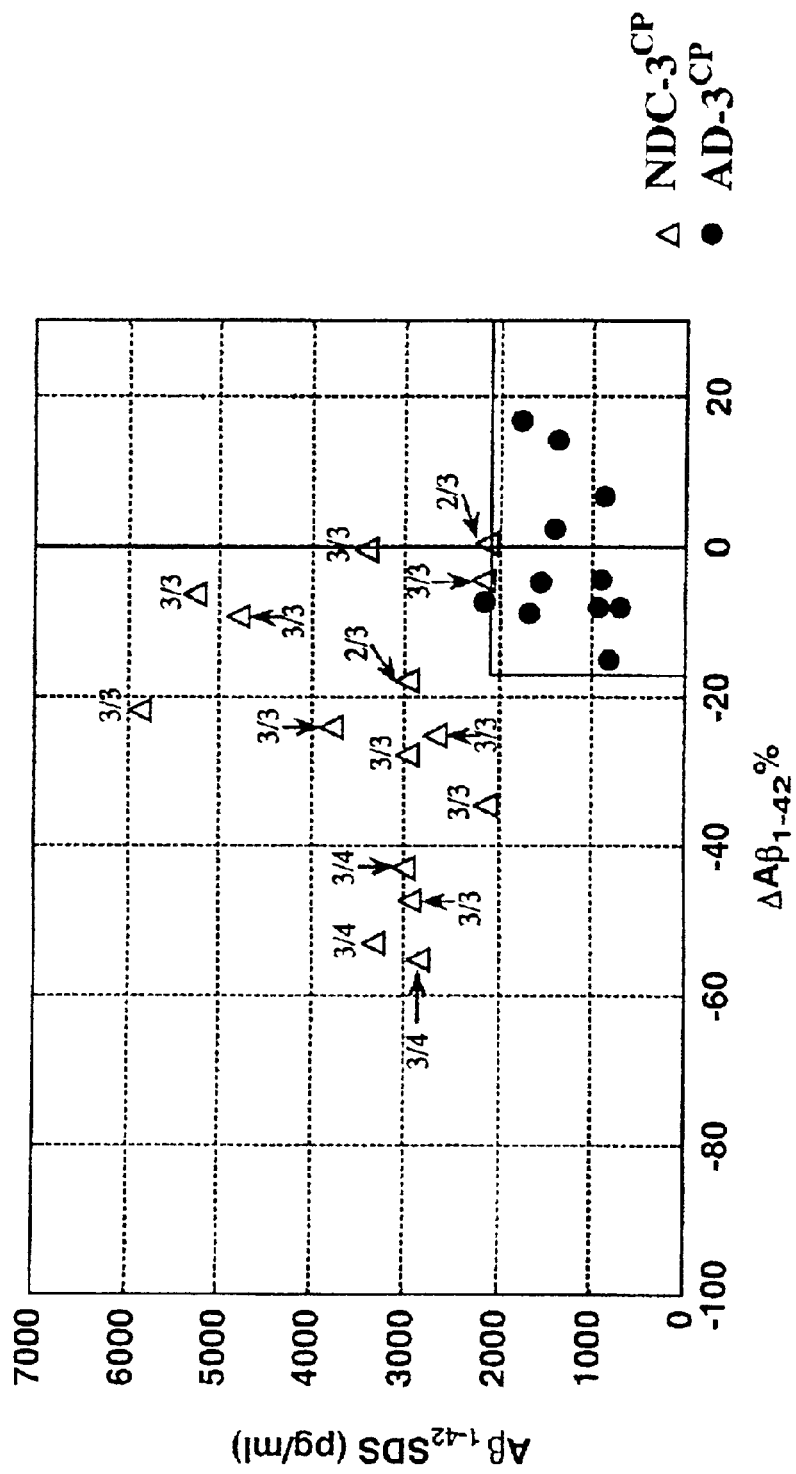
FIG. 20: a plot of Aβ1-42 SDS in CSF in NDC-3CP and AD-3CP as a function of ΔAβ1-42%, i.e. as a function of the reduction caused by cryoprecipitation in Aβ1-42. The limit lines (Aβ1-42=2100, ΔAβ1-42%=−17) relate to the AD-3CP group. The zero axis i.e. no reduction caused by cryoprecipitation in Aβ1-42, is indicated by a line. The ApoE genotype is indicated for the NDC-3CP patients. 9/11 of the AD-3CP patients had at least one ApoE ε4 allele. The ApoE ε4 genotype was unavailable for 2/11 of the AD-4 patients.

At the same time, these two subgroups of patients differ particularly markedly in their reduction caused by CP in $A\beta_{1-42}$. This is particularly large in the $\epsilon 4$-positive NDC-3CP patients and is almost completely absent from the $\epsilon 4$-positive AD-3CP patients. Accordingly, the $\epsilon 4$-positive patients from the AD-$3^{CP}$ group have, in contrast to the $\epsilon 4$-positive patients from the NDC-$3^{CP}$ group, low levels of $A\beta_{1-42}$ in the CSF despite "protective" SDS/thermal denaturation before freezing. Correspondingly, the two groups of AD-$3^{CP}$ and NCD-$3^{CP}$ patients should be differentiated considerably better via determination of $A\beta_{1-42}$ in the CSF after pretreatment with SDS/thermal denaturation ($A\beta_{1-42}$SDS). FIG. 20 confirms this assumption:

The reduction caused by CP in $A\beta_{1-42}$ is reduced by the proportion which can be prevented by the "protective" SDS/thermal denaturation, leading to the NDC-$3^{CP}$ patients now having distinctly higher $A\beta_{1-42}$ levels in the CSF ($A\beta_{1-42}$SDS) on average. The $A\beta_{1-42}$ levels in the CSF in AD-3CP on the other hand remain low, substantially unchanged.

Correspondingly, the level of significance of the comparison of the NDC-$3^{CP}$ versus the AD-$3^{CP}$ group is markedly improved (p=$1.81 \times 10^{-6}$) on differentiation of the groups via $A\beta_{1-42}$SDS. All NDC patients (15/15) and only one AD patient (1/11) are now above the concentration limit of $A\beta_{1-42}$SDS=2100 pg/ml.

As stated above, this effect is particularly pronounced in the carriers of $\epsilon 4$ alleles within the NDC-$3^{CP}$ group. However, FIGS. 19 and 20 make it clear that this effect is not determined exclusively by the presence of the $\epsilon 4$ allele. Some patients with, for example, the ApoE genotype 3/3 likewise show a pronounced reduction caused by CP in $A\beta_{1-42}$, which can be reduced by SDS/thermal denaturation before freezing. In summary, the $A\beta$ peptide limits can be stated to be as follows:

$A\beta_{1-42}$native=2100 pg/ml & $\%\Delta A\beta_{1-42}$=−17%: All AD patients (11/11) are correctly classified and one NDC patient (1/15) is incorrectly classified.

$A\beta_{1-42}$native=2300 pg/ml & $\%\Delta A\beta_{1-42}$=−20%: all AD patients (11/11) are correctly classified and two NDC patients (2/15) are incorrectly classified.

And $A\beta_{1-42}$SDS=2100 pg/ml & $\%\Delta A\beta_{1-42}$=−17%: 10/11 AD-$3^{CP}$ patients are correctly classified and no NDC-$3^{CP}$ patient (0/15) is incorrectly classified.

$A\beta_{1-42}$SDS=2300 pg/ml & $\%\Delta A\beta_{1-42}$=−20%: all AD patients (11/11) are correctly classified and two NDC patients (2/15) are incorrectly classified.

Determination of $\%\Delta A\beta_{1-42}$ in addition to $A\beta_{1-42}$SDS is expected to improve neurochemical AD diagnosis further: With an $A\beta_{1-42}$SDS limit of 2300 pg/ml instead of 2100 pg/ml, three NDC patients (3/15) are incorrectly classified and all AD patients are correctly classified. If the limit $\%\Delta A\beta_{1-42}$=−20% is additionally taken into account, only two NDC patients (2/15) are incorrectly classified and all AD patients are correctly classified. It is thus possible for the $A\beta_{1-42}$SDS threshold concentration to rise by 200 pg/ml without simultaneously reducing the diagnostic specificity.

In summary, it is possible to deduce from the abovementioned findings on the reduction caused by CP in Aβ peptides the following hypotheses: In human CSF, $A\beta_{1-42}$ is present more than $A\beta_{1-40}$ in a fraction which can be reduced in a CP-dependent fashion. $A\beta_{1-42}$ can be released at least partially from this fraction by the use of detergents, and the reduction caused by CP can be reduced. This $A\beta_{1-42}$-binding fraction probably comprises comparatively hydrophobic high molecular weight complexes involving $A\beta_{1-42}$ and probably other proteins (e.g. lipoproteins).

(Note: it was possible to show by analysis of fractions from the gel filtration (SEC-FPLC) of human CSF by means of Aβ SDS-PAGE/immunoblot that a considerable proportion is transported, selectively accentuated for $A\beta_{1-42}$, in a high molecular weight fraction).

In AD—in contrast to NDC—$A\beta_{1-42}$ can scarcely be displaced from this fraction even by strong detergents, indicating an AD-specific composition of this complex. In this case, it would be expected that there would be a specific reduction in $A\beta_{1-42}$ in the CSF in AD even if the samples were to be measured directly after detergent treatment, i.e. without previous freezing. Thus the samples might be stored after detergent treatment at room temperature in the presence of SDS and protease inhibitors (3.1.3.1b, SDS-SB-3) until measured, because they would be very efficiently protected from autoaggregation, precipitation, nonspecific protease activity and microcolonization.

It may be assumed, alternatively, that the reduction in $A\beta_{1-42}$ in AD is essentially due to the fact that the CSF contains less $A\beta_{1-42}$ in total in AD.

When there is high-affinity detergent-stable binding of $A\beta_{1-42}$ to a complex, the peptide increasingly escapes enzymatic catabolism in this binding. This complex therefore also represents a target for the development of medicaments for Alzheimer's dementia, because substances which compete with the binding of Aβ peptides to this complex might increasingly provide Aβ peptides for enzymatic catabolism. The reduction of $A\beta_{1-42}$ in CSF in some of the is patients with Creutzfeldt-Jakob dementia, another amyloidosis or protein folding disease of the CNS, suggests that this complex might have a comparable composition in the two disorders.

The abovementioned findings are also relevant to the early diagnosis or preclinical diagnosis of AD. The question which arises here is whether patients which despite "protective" SDS/thermal denaturation ($A\beta_{1-42}$SDS) show low $A\beta_{1-42}$ levels in the CSF and are simultaneously noteworthy due to a small decrease caused by CP in $A\beta_{1-42}$ ($\Delta A\beta_{1-42}\%$) have a particularly high risk of developing AD. This question might be answered by a prospective study on patients with mild cognitive disorders (ICD10 F06.7), because these patients develop an AD within two years in up to 30% of cases. In such cases a single CSF puncture with subsequent assessment of the course (clinical, neuropsychology, imaging) would be sufficient because the predictive value of the parameters could be determined retrospectively.

This suggests that in principle an A (frozen untreated) and B aliquot (SDS/thermal denaturation before freezing) of the CSF sample should be obtained for each patient. It is sufficient where appropriate for the samples to be cooled for example to 0° C. while monitoring the temperature of the individual sample in a standardized manner.

It will in general be possible to combine the differential sample preparation described above also with ELISA methods or the use of fluorescence correlation spectroscopy (FCS) for determining $A\beta_{1-42}$ in CSF.

The detection sensitivity of the BioSource ELISA for determining $A\beta_{1-42}$ in human CSF is, for example, 10 pg/ml.

This detection sensitivity allows the SDS/thermally denatured CSF to be diluted at least five-fold before the measurement on loading of 100 µl of sample. The resulting concentration of 0.1% SDS (w/v) does not according to our results adversely affect the N-terminal capture antibody used in the first step in this ELISA. This may also be demonstrated analogously for the N-terminally selective antibodies 1E8 and 6E10 employed in the RIPA-IP.

In the FCS with cross correlation using fluorescence-labeled N-terminally and C-terminally selective antibodies, the signal intensity is proportional to the Aβ peptides bound in such aggregates. The sensitivity of the method once again allows the sample after SDS/thermal denaturation to be diluted to SDS concentrations of, for example, 0.1% w/v. If $A\beta_{1-42}$ is bound in a detergent-stable manner to high molecular weight aggregates selectively in AD, pretreatment of the CSF samples with detergents will increase the specificity of the measurement because the Aβ peptides are released from the high molecular weight aggregates in the NDC patients in contrast to the AD patients. The diminished reduction in the fluorescence signal in the FCS (cross correlation) after detergent treatment in patients with AD compared with patients with NDC might thus be relevant for neurochemical diagnosis of AD.

Figure 21A:
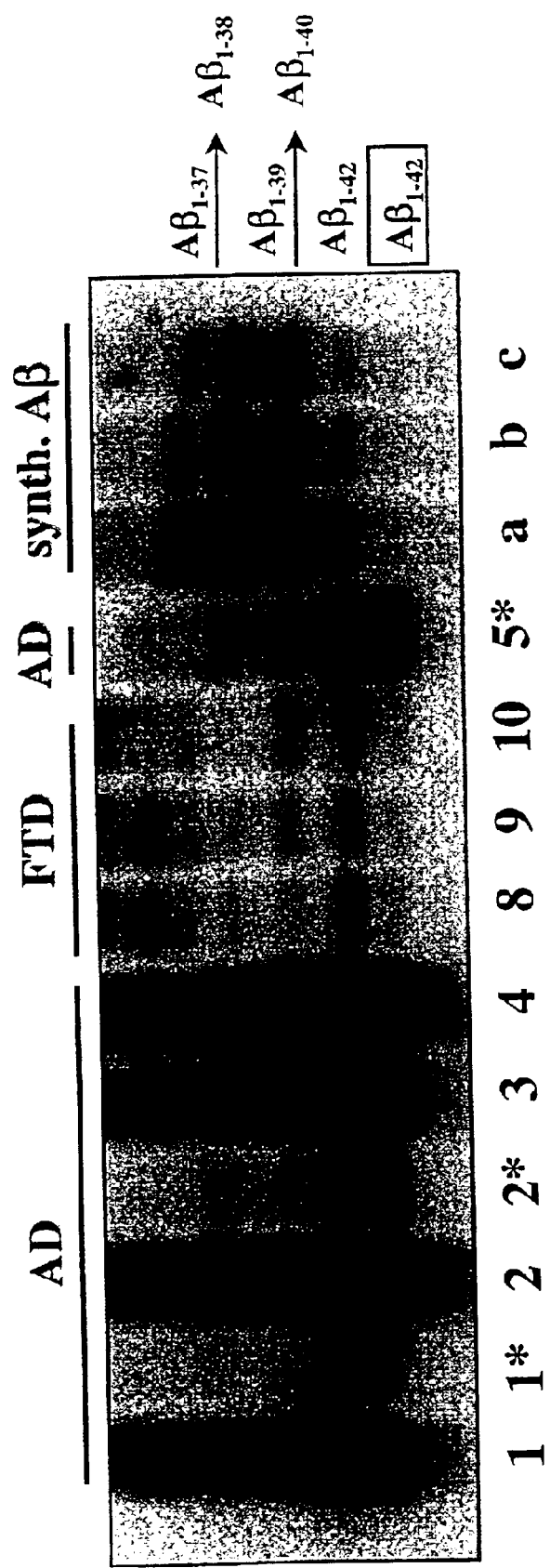
FIG. 21a: an Aβ SDS-PAGE/immunoblot 2: immunoprecipitates (RIPA-IP, mAb 1E8) of RIPA-soluble Aβ peptides from homogenates of temporal cortex in AD compared with frontotemporal dementia (FTD). Volume applied 4 μl. In columns a to c: mix of synthetic Aβ peptides (dilution series). In columns 1 to 4 and 5: temporal cortex in AD. (* the immunoprecipitate in AD was diluted twenty-fold for some patients.) In columns 8 to 10: temporal cortex in FTD.

4.2.5 Brain Homogenates from Patients with AD, Frontotemporal Dementia, Lewy Body Dementia and Controls Brain tissue (frontotemporal cortex, cerebellum) from patients with AD, frontotemporal dementia (FTD), Lewy body dementia (LBD) and non-dementing controls was was homogenized in the presence of RIPA detergent buffer (3.4.6). An immunoprecipitation was subsequently carried out in the presence of RIPA. $A\beta_{1-38}$, $A\beta_{1-40}$, $A\beta_{1-42}$ and $A\beta_{2-42}$ were detectable in the RIPA detergent-extractable fraction of the Aβ peptides (FIGS. 21a,b). $A\beta_{2-42}$ was identified by MALDI-TOF analysis directly from the blot membrane (data not shown), Aβ SDS-PAGE/immunoblot 2 (FIG. 23b) and Aβ IPG 2D-PAGE/immunoblot 2 (FIG. 24c). $A\beta_{2-42}$ is also detected in CSF samples in AD (FIG. 23a) and in cell culture supernatants (FIG. 23a, FIGS. 28a,b).

Figure 21B:
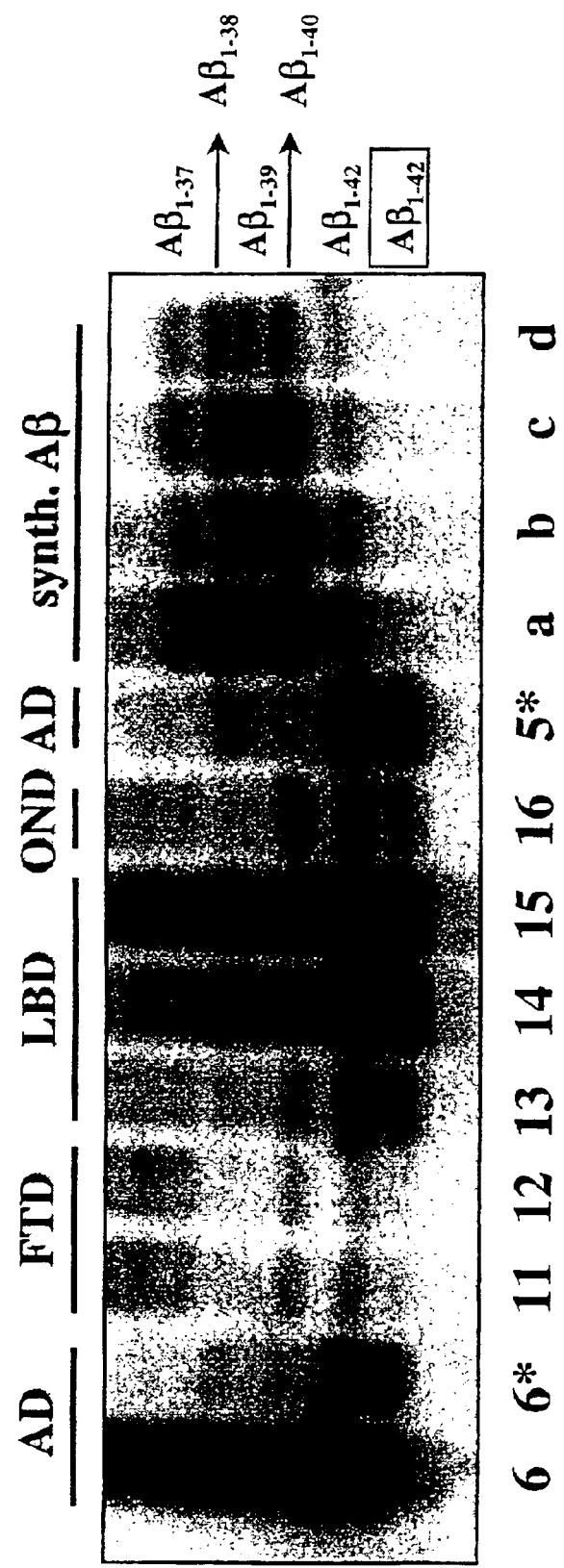
FIG. 21b: an Aβ SDS-PAGE/immunoblot 2: immunoprecipitates (RIPA-IP, mAb 1E8) of RIPA-soluble Aβ peptides from homogenates of temporal cortex in AD compared with frontotemporal dementia (FTD), Lewy body dementia (LBD) and control patients without dementia (NDC). Volume applied 4 μl. In columns

Patients with AD were characterized by comparison with non-dementing controls and patients with FTD by a massive increase in $A\beta_{1-42}$ and $A\beta_{2-42}$. This increase was far more pronounced in the frontotemporal cortex than in the cerebellum (FIG. 22). Patients with LBD showed increases in $A\beta_{1-42}$ and $A\beta_{2-42}$ which depended on a number of Alzheimer-typical β-amyloid plaques additionally present, which were recorded via the CERAD classification (FIG. 21b): patients with LBD CERAD A had distinctly less $A\beta_{1-42}$ and $A\beta_{2-42}$ than patients with LBD CERAD C.

In Alzheimer's dementia it was noteworthy that the $A\beta_{1-38}$ concentrations were comparatively high (FIGS. 21a,b). It was at the same time noteworthy that there was tissue-specific expression of $A\beta_{1-38}$ in AD, because $A\beta_{1-38}$ was distinctly less, or was undetectable, in the cerebellum relative to the frontotemporal cortex and, in addition, a previously uncharacterized band was measurable below $A\beta_{1-38}$ in some patients (FIG. 22). Since the carboxy-terminal cut is effected by γ-secretase(s), this is evidence of a possible tissue-specific difference in expression of γ-secretase(s). Since it is known that few Alzheimer-typical neuropathological changes are found in the cerebellum compared with other regions of the brain in AD, this finding might be of pathophysiological relevance.

The extremely high concentrations of $A\beta_{2-42}$, sometimes at the level of $A\beta_{1-42}$, in an RIPA-extractable brain preparation has not previously been described. In some patients there was additionally a comparatively large increase in $A\beta_{1-40}$.

Thus the Aβ SDS-PAGE/immunoblot can be employed for the neuropathological differential diagnosis of dementing disorders and, where appropriate via biochemical phenotyping, contribute to the differentiation of subgroups of sporadic AD.

4.3 Cisternal CSF from Rabbits and Guinea Pigs.

$A\beta_{1-37/38/39}$ are also detectable in addition to $A\beta_{1-40}$ and $A_{1-42}$ in the cisternal CSF of the adult guinea pig (FIG. 25a) and rabbit (FIG. 25b). The variation in the measurements is distinctly reduced if, in analogy to the patients' samples, the SDS/thermal denaturation is carried out before freezing the samples. This sample pretreatment is relevant for projects for finding active ingredients using guinea pigs or rabbits as animal model because certain effects of substances (e.g. secretase inhibition) can be detected in this way with distinctly fewer animals in each treatment and control group.

4.4 Hippocampal Tissue Sections from the Adult Guinea Pig with Short-Term Culture In short-term cultures of hippocampal tissue sections from the adult guinea pig there is secretion of $A\beta_{1-37}/38/39$ in addition to $A\beta_{1-40}$ and $A\beta_{1-42}$ into the supernatant, and intracellular detection thereof is also possible (FIG. 26).

4.5 Cell Culture 4.5.1 Primary Telencephalic Chick Culture

Since the chick Aβ peptide amine acid sequence and the human sequence agree, a primary neuronal cell culture system was established from the anterior cerebral vesicles of chick embryos (cf. 3.7). It emerged from this that besides $A\beta_{1-40}$ and $A\beta_{1-42}$ there is release of the C-terminally truncated Aβ peptides 1-37/38/39 into the cell culture supernatants, and the relative distribution of the Aβ peptides agrees well with that in human CSF.

4.5.2 Transgenic APP751$_{Sw}$ Neuroglioma Cell Line

A comparative investigation was carried out on the Aβ peptide pattern in neuroglioma cells (H4) which have been transfected with $_{human}$APP751$_{Sw}$. FIGS. 28a&b shows that in this case too besides $A\beta_{1-40}$ and $A\beta_{1-42}$, there is release of the C-terminally truncated Aβ peptides 1-37/38/39 into the cell culture supernatants. $A\beta_{2-42}$ can also be indentified. After treatment with inhibitors of β/γ-secretases (calpain inhibitor I&II, calpeptin, MG132, leupeptin), besides $A\beta_{1-40}$ and $A\beta_{1-42}$ there is also a reduction in the C-terminally truncated Aβ peptides 1-37/38/39 and the N-terminally truncated $A\beta_{2-42}$ (FIGS. 28a,b). FIG. 28b shows the dose-dependent reduction with calpain inhibitor 1.

It can accordingly be assumed that the Aβ peptides 1-37/38/39 are, as known for 1-40/42, also produced by the combined α/γ-secretase cut. The reduction in 2-42 may be due to inhibition of β/γ-secretase activity or to reduced supply of substrate ($A\beta_{1-42}$) for a subsequent N-terminal aminopeptidase (but see below).

It is evident from FIGS. 29a&b that the kinetics of inhibition of the C-terminally truncated Aβ peptides 1-37, 1-38 and 1-39 differ from those for $A\beta_{1-40}$ and $A\beta_{1-42}$. The difference in the kinetics is particularly marked for $A\beta_{1-37}$. This finding indicates that a heterogeneity of γ-secretase activity which is relevant for finding selective γ-secretase inhibitors as active ingredients can be revealed through the Aβ peptide pattern. It is also noteworthy that the paradoxical increase known from the literature in $A\beta_{1-42}$ at low inhibitor concentrations is not correlated with an increase in $A\beta_{2-42}$. This is against secondary production of $A\beta_{2-42}$ from $A\beta_{1-42}$.

A further alternative must be taken into account for the production of $A\beta_{1-37}$. It has recently been described that neutral endopeptidase (NEP) is essentially involved through the combined 10/11 and 37/38 cut in the catabolism of Aβ peptides (Iwata et al., 2000). Thus $A\beta_{1-37}$ might also be produced by the combination of BACE cut and 37/38 NEP cut.

| List of abbreviations: | |
|---|---|
| Aβ | β-amyloid |
| AD | Alzheimer's dementia |
| APP | amyloid precursor protein |
| FAD | familial AD, i.e. caused genetically |
| PS-1 | presenilin 1 |
| PS-2 | presenilin 2, |
| Bis | N,N'-methylenebisacrylamides |
| Bicine | N,N'-bis[2-hydroxyethyl]glycine |
| % T | total acrylamide monomer concentration (w/v) |
| % C | proportion of bis in the total amount of acrylamide monomer (w/w) |
| Aβ SDS-PAGE | β-amyloid sodium lauryl sulfate polyacrylamide gel electropheresis |
| Aβ 2D-PAGE | β-amyloid two-dimensional polyacrylamide gel electrophoresis |
| IPG | immobilized pH gradient |
| Aβ1-n | $A\beta_{1-n}$ |

5. References

Görg A., Boguth G., Obermaier C., Posch A. and Weiss W. (1995) Two-dimensional polyacrylamide gel electrophoresis with immobilized pH gradients in the first dimension (IPG-Dalt): the state of the art and the controversy of vertical versus horizontal systems. *Electrophoresis* 16, 1079–86.

Görg A., Obermaier C., Boguth G., Csordas A., Diaz J. J. and Madjar J. J. (1997) Very alkaline immobilized pH gradients for two-dimensional electrophoresis of ribosomal and nuclear proteins. *Electrophoresis* 18, 328–37.

Heukeshoven J. and Dernick R. (1988) Improved silver staining procedure for fast staining in PhastSystem Development Unit. I. Staining of sodium dodecyl sulfate gels. *Electrophoresis* 9, 28–32.

Hulstaert F., Blennow K., Ivanoiu A., Schoonderwaldt H. C., Riemenschneider M., De Deyn P. P., Bancher C., Cras P., Wiltfang J., Mehta P. D., Iqbal K., Pottel H., Vanmechelen E. and Vanderstichele H. (1999) Improved discrimination of AD patients using beta-amyloid(1-42) and tau levels in CSF. *Neurology* 52, 1555–62.

Ida N., Hartmann T., Pantel J., Schroder J., Zerfass R., Forstl H., Sandbrink R., Masters C. L. and Beyreuther K. (1996) Analysis of heterogeneous A4 peptides in human cerebrospinal fluid and blood by a newly developed sensitive Western blot assay. *J Biol Chem* 271, 22908–14.

Klafki H., Abramowski D., Swoboda R., Paganetti P. A. and Staufenbiel M. (1996) The carboxyl termini of beta-amyloid peptides 1-40 and 1-42 are generated by distinct gamma-secretase activities. *J Biol Chem* 271, 28655–9.

Klafki H. W., Wiltfang J. and Staufenbiel M. (1996) Electrophoretic separation of betaA4 peptides (1-40) and (1-42). *Anal Biochem* 237, 24–9.

Kuo Y. M., Emmerling M. R., Woods A. S., Cotter R. J. and Roher A. E. (1997) Isolation, chemical characterization, and quantitation of A beta 3-pyroglutamyl peptides from neuritic plaques and vascular amyloid deposits. *Biochem Biophys Res Commun* 237, 188–91.

Laemmli U. (1970) Cleavage of structural proteins during the assembly of the head of bacteriophage T4. *Nature* 227, 680–685.

McKhann G., Drachman D., Folstein M., Katzman R., Price D. and Stadlan E. M. (1984) Clinical diagnosis of Alzheimer's disease: report of the NINCDS-ADRDA Work Group under the auspices of Department of Health and Human Services Task Force on Alzheimer's Disease. *Neurology* 34, 939–44.

Metz C. E. (1978) Basic principles of ROC analysis. *Semin Nucl Med* 8, 283–98.

O'Farrell P., Goodman H. and O'Farrell P. (1977) High resolution two-dimensional electrophoresis of basic as well as acidic proteins. *Cell* 12, 113–341.

O'Farrell P. H. (1975) High resolution two-dimensional electrophoresis of proteins. *J Biol Chem* 250, 4007–21.

Righetti P. G. and Bossi A. (1997) Isoelectric focusing in immobilized pH gradients: recent analytical and preparative developments. *Anal Biochem* 247, 1–10.

Russo C., Saido T. C., DeBusk L. M., Tabaton M., Gambetti P. and Teller J. K. (1997) Heterogeneity of water-soluble amyloid beta peptides in Alzheimer's disease and Down's syndrome brains. *FEBS Lett* 409, 411–6.

Schagger H. and von Jagow G. (1987) Tricine-sodium dodecyl sulfate-polyacrylamide gel electrophoresis for the separation of proteins in the range from 1 to 100 kDa. *Anal Biochem* 166, 368–79.

Tamaoka A., Sawamura N., Fukushima T., Shoji S., Matsubara E., Shoji M., Hirai S., Furiya Y., Endoh R. and Mori H. (1997) Amyloid beta protein 42(43) in cerebrospinal fluid of patients with Alzheimer's disease. *J Neurol Sci* 148, 41–5.

Thome J., Kornhuber J., Munch G., Schinzel R., Taneli Y., Zielke B., Rosler M. and Riederer P. (1996) [New hypothesis on etiopathogenesis of Alzheimer syndrome. Advanced glycation end products (AGEs)]. *Nervenarzt* 67, 924–9.

Thome J. M. G., Schinzel R., Kornhuber J., Blum-Degen D., Sitzmann L., Rösler M., Heidland A., Riederer P. (1996) Advanced glycation end products-associated parameters in the peripheral blood of patients with Alzheimer's disease. *Life Sci.* 59, 679–685.

Wiltfang J., Arold N. and Neuhoff V. (1991) A new multiphasic buffer system for sodium dodecyl sulfate-polyacrylamide gel electrophoresis of proteins and peptides with molecular masses 100,000–1000, and their detection with picomolar sensitivity. *Electrophoresis* 12, 352–66.

Wiltfang J., Smirnov A., Schnierstein B., Kelemen G., Matthies U., Klafki H. W., Staufenbiel M., Huther G., Ruther E. and Kornhuber J. (1997) Improved electrophoretic separation and immunoblotting of beta-amyloid (A beta) peptides 1-40, 1-42, and 1-43. *Electrophoresis* 18, 527–32.

Wiltfang J., Otto M., Rüther E., Kornhuber J. (1998) Klinisch-chemische Früh-und Differentialdiagnostik der Alzheimer Demenz, *psycho* 24, 726–31.

Wiltfang J., Esselmann H., Smirnov A., Maler M. J., Bleich S., Otto M., Bibl M., Rüther E., Kornhuber J. (2000) Therapieansätze in der Alzheimer-Demenz, *Notfallmedizin* 26, 246–51.

TABLE 1

Stock solutions and buffers for the Aβ SDS-PAGE

| Solution | Composition |
| --- | --- |
| Resolving gel buffer | 1.6 M Tris, 0.4 M H$_2$SO$_4$ |
| Stacking gel buffer | 0.8 M Bistris, 0.2 M H$_2$SO$_4$ |
| Comb gel buffer | 0.72 M Bistris, 0.32 M Bicine |
| Cathode buffer | 0.2 M Bicine, 0.1 M NaOH, 0.25% w/v SDS |
| Anode buffer | 0.2 M Tris, 0.05 M H$_2$SO$_4$ |
| 1% SDS | 1% (w/v) SDS |
| 10% SDS | 10% (w/v) SDS |
| Acrylamide/Bis 60% T/3% C[1] | 58.2% (w/v) Acrylamide, 1.8% (w/v) Bis |
| Acrylamide/Bis 60% T/5% C[1] | 57% (w/v) Acrylamide, 3% (w/v) Bis |

[1]The acrylamide stock solution is stirred with AG 501-X8D mixed bed ion exchanger matrix (Bio-Rad, RichmNDC, CA, USA) for 30 min, filtered and stored in the dark at room temperature.

TABLE 2

Composition of comb, stacking and resolving gels for the Aβ SDS-PAGE

| Solution | Comb gel 9% T/5% C | Stacking gel 6% T/5% C | Resolving gel 12% T/5% C/ 8 M urea |
| --- | --- | --- | --- |
| Comb gel buffer | 2000 μl | | |
| Stacking gel buffer | | 2000 μl | |
| Resolving gel buffer | | | 2500 μl |
| Acrylamide/Bis (60% T/3% C) | 400 μl | 400 μl | |
| Acrylamide/Bis (60% T/5% C) | | | 2000 μl |
| Urea | | | 4.80 g |
| 1% (w/v) SDS | 1000 μl | 1000 μl | |
| 10% (w/v) SDS | | | 250 μl |
| H$_2$O | 600 μl | 600 μl | ad 10 ml (ca. 1.51 ml) |
| 10% AMPS | 24 μl | 24 μl | 40 μl |
| TEMED | 8 μl | 8 μl | 5 μl |
| Bromophenol blue, 1% (w/v) | 15 μl | | |

TABLE 3

Composition of the buffers for the taking up of samples (SDS-SB)

| Reagent | SDS-SB-1* | SDS-SB-2* | SDS-SB-3* |
| --- | --- | --- | --- |
| Bistris | 0.36 M | 0.72 M | 0.120 M |
| Bicine | 0.16 M | 0.32 M | 0.053 M |
| Sucrose | 15.0% (w/v) | 30.0% (w/v) | 5.0% (w/v) |
| SDS | 1.0% (w/v) | 2.0% (w/v) | 0.5% (w/v) |
| Bromophenol blue | 0.004% (w/v) | 0.008% (w/v) | 0.002% (w/v) |
| Proteinase inhibitor cocktail tablets | | | 1 Tabl./10 ml |

*boil with 2.5% (v/v) 2-mercaptoethanol at 95° C. for 5 min immediately before Aβ SDS-PAGE

TABLE 4a

Composition of the IEF-SB

| Reagent | IEF-SB |
|---|---|
| Urea | 8 M |
| CHAPS | 0.27% (w/v) |
| NP-40 | 0.13% (v/v) |
| Servalyt pH 3–10 (40%) | 1% (v/v) |
| Servalyt pH 4–7 or pH 5–6 | 1% (v/v) |
| 2-Mercaptoethanol | 5% (v/v) |

TABLE 4b

Composition of the carrier ampholyte IEF round gel

| Solution | Volume | IEF round gel |
|---|---|---|
| Acrylamide/Bis (60% T/3% C) | 89 µl | 5.4% T/3% C |
| $H_2O_{dd}$ | 280 µl | |
| Urea | 480 mg | 8 M |
| 2% (w/v) CHAPS | 135 µl | 0.27% |
| 2% (w/v) NP-40 | 65 µl | 0.13% |
| Servalyt pH 3–10 (40%) | 25 µl | 1% |
| Servalyt pH 5–6 or 4–7 | 25 µl | 1% |
| 1% (w/v) AMPS | 20 µl | |
| 10% (v/v) TEMED | 10 µl | |

TABLE 4c

Composition of anolyte and catholyte for the carrier ampholyte IEF

| Solution | Composition |
|---|---|
| Catholyte | 20 mM NaOH |
| Anolyte | 10 mM $H_3PO_4$ |

TABLE 4d

Composition of the IEF equilibration buffer and of the IEF agarose solution

| Reagent | IEF equilibration buffer | IEF agarose solution |
|---|---|---|
| Bicine | 0.16 M | 0.16 M |
| Bistris | 0.36 M | 0.36 M |
| SDS | 1% (w/v) | 1% (w/v) |
| Bromophenol blue | | 0.004% (w/v) |

TABLE 5a

Composition of IPG-SB (lysis buffer) and IPG rehydrogenation buffer

| Reagent | IPG-SB (lysis buffer) | IPG rehydrogenation solution |
|---|---|---|
| Urea | 9.0 M | 8.0 M |
| Serdolit MB-1 | 1.0% (w/v) | 1.0% (w/v) |
| CHAPS | 2.0% (w/v) | 0.5% (w/v) |
| DTT | 1.0% (w/v) | 0.2% (w/v) |
| Pharmalyte pH 3–10 (40%) | 0.8% (v/v) | 0.8 (v/v) |

TABLE 5b

Composition of the IPG equilibration buffer

| Reagent | IPG equilibration buffer |
|---|---|
| Urea | 6.0 M |
| Glycerol (100%) | 20.0% (w/v) |
| SDS | 2.0% (w/v) |
| Bistris | 0.36 M |
| Bicine | 0.16 M |

1. Incubate in IPG equilibration buffer with 1% (w/v) DTT at room temperature shaking gently for 10 min
2. Incubate in IPG equilibration buffer with 4.8% (v/v) iodoacetamide at room temperature shaking gently for 10 min

TABLE 5c

Composition of the IPG agarose solution

| Reagent | IPG agarose solution |
|---|---|
| Agarose | 1.0% (w/v) |
| SDS | 0.25% (w/v) |
| Bromophenol blue | 0.002% (w/v) |
| Bistris | 0.36 M |
| Bicine | 0.16 M |

TABLE 6

Composition of the RIPA buffer

| Reagent | *$RIPA_{1x}$ | *$RIPA_{0.5x}$ |
|---|---|---|
| HEPES/NaOH pH 7.4 | 50 mM | 50 mM |
| NP40 | 1.0% (v/v) | 0.5% (v/v) |
| Na deoxycholate | 0.5% (w/v) | 0.25% (w/v) |
| SDS | 0.1% (w/v) | 0.05% (w/v) |
| NaCl | 150 mM (w/v) | 150 mM (w/v) |

*Addition: 1 tablet of protease inhibitor mix per 10 ml of $RIPA_{0.5x}$ or $RIPA_{1x}$ buffer

TABLE 7

Silver staining after glutaraldehyde fixation

| Solutions | Time (min) |
|---|---|
| cold (4° C.) $H_2O_{dd}$ | 3 × 10 |
| 30% (v/v) EtOH, 10% (v/v) Hac[1] | 1 × 60 |
| 30% (v/v) EtOH, 0.5 M sodium acetate 0.5% (v/v) glutaraldehyde, 0.2% $Na_2S_2O_3$ | 1 × 60 |
| cold (4° C.) $H_2O_{dd}$ | 3 × 15 |
| 0.1% (w/v) $AgNO_3$, 0.02% (v/v) formaldehyde | 1 × 60 |
| 2.5% (w/v) $Na_2CO_3$, 0.02% (v/v) formaldehyde | 5–10 |
| 0.05 M (w/v) glycine | 30 |

[1]Gels after glutaraldehyde fixation (Wiltfang et al., 1997, Electrophoresis 18: 527–32) can be stored in this solution at 4° C. if the silver staining is to be carried out later.
The Aβ peptides and proteins investigated here can also be fixed directly in EtOH/Hac.

TABLE 8

Composition of the blot buffers for the Western immunoblot

| Reagent | Blot buffer A | Blot buffer B | Blot buffer C |
|---|---|---|---|
| Tris | 0.21 M | 25 mM | 25 mM |
| Methanol | 30% (v/v) | 30% (v/v) | |
| SDS | | | 0.025% (w/v) |
| pH | 10.4 | 10.4 | 9.0* |

*adjusted with 0.5 M boric acid

TABLE 9a

Stock solutions for the immunoblot

| Solution | Composition |
|---|---|
| $PBS_{10\times}$ (10× conc.) | 95.5 g phosphate-buffered NaCl to 1000 ml $H_2O_{dd}$ |
| PBS-T (0.075% v/v Tween-20 in PBS) | 75 ml Tween-20 ad 1000 ml $PBS_{1\times}$ |
| PBS-T-M | 2.5 g milk powder ad 100 ml PBS-T |

TABLE 9b

Buffers, solutions and antibodies for Western immunoblots 1 and 2

| Immunoblot step | Time | Western Immunoblot 1 | Western Immunoblot 2 |
|---|---|---|---|
| Blocking of nonspecific binding sites | 1 h | 2.5% (w/v) milk powder in PBS-T | 10% (v/v) Roti-Block in $H_2O_{dd}$ |
| Incubation with primary mAb at 4° C. overnight | 15 h | a) mAb 1E8, 1:4000 in milk powder PBS-T; mAb 6E10, 1:1000 in milk powder PBS-T | a) mAb 1E8, 1:4000 in 10% (v/v) Roti-Block/$H_2O_{dd}$ |
| Washing step | 3 × 10 min | PBS-T | PBS-T |
| Incubation with secondary Ab at room temperature | 1 h | Biotinylated anti-mouse antibody, 1:3000 in in milk powder PBS-T | Biotinylated anti-mouse antibody, 1:3000 in PBS-T |
| Washing step | 3 × 10 min | PBS-T | PBS-T |
| Incubation with streptavidin-POD at room temperature | 1 h | Streptavidin-POD complex, 1:3000 in PBS-T | Streptavidin-POD complex, 1:3000 in PBS-T |
| Washing step | 3 × 10 min | PBS-T | PBS-T |

TABLE 10a–d

Constitution of the groups with intersections of patients in common. NDC-3$^{CP}$ is entirely a subgroup of NDC-3. AD-3$^{CP}$ is substantially a subgroup of AD-3

| Table 5a) | NDC1 (n = 30) |
|---|---|
| NDC-2$^{CP}$ (n = 10) | Intersection (n = 2): NP55, NP57 |
| Table 5b) | NDC-3 (n = 47) |
| NDC-3$^{CP}$ (n = 15; subset of NDC-3) | Intersection (n = 15): NP213, NP344, NP345, NP352, NP355, NP356, NP364, NP374, NP402, NP412, NP419, NP421, NP457, NP490, NP 526 |
| Table 5c) | AD-1 (n = 35) |
| AD-3 (n = 12) | Intersection (n = 3): NP37, NP52, NP66 |
| AD-3$^{CP}$ (n = 11) | Intersection (n = 3): NP52, NP66, NP69 |
| Table 5d) | AD-3 (n = 12) |
| AD-3$^{CP}$ (n = 11; intersection plus NP69/NP197) | Intersection (n = 9): NP45, NP52, NP58, NP66, NP111, NP143, NP190, NP319, NP320 |

TABLE 11

Aβ SDS-PAGE/immunoblot 1 of synthetic Aβ peptides after the samples have been directly taken up in SDS-PAGE sample buffer and ECL detection by exposure of films: inter- and intraassay coefficients of variation

| Aβ peptides | Interassay-CV* | Intraassay-CV* |
|---|---|---|
| $A\beta_{1-40}$ (100 pg) | 8.5 | 4.8 |
| $A\beta_{1-40}$ (75 pg) | 8.7 | 6.1 |
| $A\beta_{1-40}$ (50 pg) | 10.8 | 5 |
| $A\beta_{1-40}$ (20 pg) | 15.4 | 8.8 |
| $A\beta_{1-42}$ (25 pg) | 10.9 | 11.1 |
| $A\beta_{1-42}$ (15 pg) | 11.7 | 16.5 |
| $A\beta_{1-42}$ (10 pg) | 19.6 | 16.4 |
| $A\beta_{1-42}$ (5 pg) | 15.1 | 22.4 |
| $A\beta_{1-42}/A\beta_{1-40}$ (25pg/100pg) | 6.9 | 7.5 |
| $A\beta_{1-42}/A\beta_{1-40}$ (15 pg/75 pg) | 11 | 12.5 |
| $A\beta_{1-42}/A\beta_{1-40}$ (10 pg/50 pg) | 15.6 | 14.3 |
| $A\beta_{1-42}/A\beta_{1-40}$ (5 pg/25 pg) | 16.7 | 19.1 |

*CV: Coefficient of variation (mean/SD × 100; %); outliers have not been eliminated.

TABLE 12

Aβ SDS-PAGE/immunoblot 1 of Aβ peptides in human CSF in NDC-1 and AD-1

| Diagnosis | P code | D Code | Age | Sex | $A\beta_{1-40}$ (ng/ml) | $A\beta_{1-42}$ (pg/ml) | $A\beta_{1-42}$ IP$ (pg/ml) | $A\beta_{42}/A\beta_{40}$* | $A\beta_{42}/A\beta_{38}$* |
|---|---|---|---|---|---|---|---|---|---|
| Tonoclonic epileptic seizure | NP6 | NDC | 49 | fem. | 10.24 | 1916.3 | 499.6 | 0.2895 | 0.4937 |
| Tonoclonic epileptic seizure | NP7 | NDC | 77 | fem. | 12.97 | 1203.3 | 268.3 | 0.1863 | 0.295 |
| Tonoclonic epileptic seizure | NP9 | NDC | 71 | male | 14.71 | 2744.2 | 815.7 | 0.3408 | 0.5239 |
| Inflam. CNS process, etiology uncl. | NP10 | NDC | 72 | male | 13.21 | 2658.3 | 596.7 | 0.2666 | 0.42 |
| Brain stem ischemia | NP12 | NDC | 79 | male | 12.61 | 2579.2 | 504.2 | 0.2567 | 0.4065 |
| Cerebral ischemia | NP13 | NDC | 69 | fem. | 14.36 | 1970.4 | 312.8 | 0.1506 | 0.2355 |
| Neuropathy, etiology uncl | NP17 | NDC | 61 | fem. | 6.61 | 2009.2 | 669.6 | 0.2569 | 0.4919 |
| Depression | NP21 | NDC | 58 | fem. | 11 | 3217.5 | 738.3 | 0.4164 | 0.7197 |
| Chlamydia-associated vasculitis | NP22 | NDC | 56 | fem. | 6.01 | 1962.9 | 350.2 | 0.2765 | 0.5004 |
| Depression with psychotic features | NP25 | NDC | 67 | fem. | 6.61 | 1844.2 | 392.1 | 0.2603 | 0.5099 |
| Inflam. CNS process, etiology uncl. | T17 | NDC | 37 | fem. | 3.38 | 802.5 | | 0.1023 | 0.2575 |
| Acute organic psychosis | T27 | NDC | 42 | male | 2.93 | 1237.1 | | 0.109 | 0.3375 |
| Catatonic schizophrenia | T28 | NDC | 42 | fem. | 2.35 | 979.2 | | 0.1041 | 0.3071 |
| Vascular dementia | T29 | NDC | 62 | male | 6.32 | 2631.3 | | 0.2358 | 0.4547 |
| Cerebral ischemia | T38, NP55 | NDC | 59 | fem. | 7.28 | 3350.8 | | 0.2496 | 0.4924 |
| Catatonic syndrome | T40, NP57 | NDC | 59 | fem. | 3.19 | 1356.3 | | 0.1267 | 0.3424 |
| Parkinsonism dementia complex | A59 | NDC | 78 | fem. | 10.36 | 734.2 | 230.4 | 0.0861 | 0.1446 |
| Parkinsonism dementia complex | A185 | NDC | 74 | male | 5.5 | 1007.1 | 376.6 | 0.2123 | 0.4624 |
| Depression-assoc. pseudodementia | A209 | NDC | 36 | fem. | 9.01 | 1475.8 | 619.5 | 0.2501 | 0.4627 |
| Subcortical encephalopathy-assoc dementia | A266 | NDC | 68 | male | 7.48 | 689.6 | 222.5 | 0.076 | 0.1649 |
| Parkinsonism dementia complex | A340 | NDC | 75 | fem. | 10.32 | 1645.4 | 387 | 0.1606 | 0.2753 |
| Parkinsonism dementia complex | A368 | NDC | 67 | male | 8.36 | 967.9 | 364.3 | 0.1114 | 0.209 |
| Depression-assoc. pseudodementia | A456 | NDC | 67 | fem. | 4.9 | 1329.6 | 362.1 | 0.1428 | 0.3644 |
| Parkinsonism dementia complex | A473 | NDC | 44 | fem. | 5.6 | 1590.8 | 431 | 0.1833 | 0.4918 |
| Parkinsonism dementia complex | A546 | NDC | 77 | fem. | 5.1 | 1602.9 | 518.9 | 0.1919 | 0.4068 |
| Parkinsonism dementia complex | A582 | NDC | 77 | fem. | 10.79 | 2918.3 | 490 | 0.3774 | 0.6543 |
| Vascular dementia | T5 | NDC | 97 | male | 5.09 | 1040.6 | | 0.1331 | |
| Vascular dementia | T13 | NDC | 73 | male | 4.85 | 546.7 | | 0.0697 | 0.1237 |
| Pick's disease dementia | T23 | NDC | 53 | male | 2.55 | 1064.2 | | 0.1112 | 0.3601 |
| Vascular dementia | T24 | NDC | 61 | male | 4.44 | 1248.8 | | 0.1065 | 0.2668 |
| Alzheimer's dementia | A72 | AD | 60 | fem. | 2.69 | 620 | 120.3 | 0.1301 | 0.4299 |
| Alzheimer's dementia | A130 | AD | 75 | fem. | 6.02 | 611.7 | 131.4 | 0.0827 | 0.1799 |
| Alzheimer's dementia | A139 | AD | 53 | fem. | 6.99 | 666.7 | 206.3 | 0.1204 | 0.2879 |
| Alzheimer's dementia | A193 | AD | 71 | fem. | 2.44 | 274.6 | 338.2 | 0.0427 | 0.2047 |
| Alzheimer's dementia | A257 | AD | 67 | male | 6.86 | 615.4 | 296.6 | 0.0685 | 0.1535 |
| Alzheimer's dementia | A279 | AD | 56 | fem. | 9.42 | 1868.8 | 363.5 | 0.1899 | 0.3691 |
| Alzheimer's dementia | A291 | AD | 81 | fem. | 3.55 | 411.9 | 530.5 | 0.047 | 0.2108 |
| Alzheimer's dementia | A391 | AD | 76 | male | 6.65 | 654.6 | 559.1 | 0.0612 | 0.1525 |
| Alzheimer's dementia | A454 | AD | 59 | male | 11.67 | 706.3 | 287.6 | 0.123 | 0.2307 |
| Alzheimer's dementia | A477 | AD | 65 | fem. | 27.94 | 1357.9 | 373 | 0.1784 | 0.3132 |
| Alzheimer's dementia | T1 | AD | 70 | male | 5.21 | 536.7 | | 0.0628 | 0.1145 |
| Alzheimer's dementia | T2 | AD | 70 | male | 5.99 | 1108.8 | | 0.0868 | 0.162 |
| Alzheimer's dementia | T3 | AD | 72 | fem. | 4.53 | 440 | | 0.0639 | 0.1542 |
| Alzheimer's dementia | T4 | AD | 68 | fem. | 5.97 | 925.8 | | 0.1153 | 0.2101 |
| Alzheimer's dementia | T6 | AD | 86 | fem. | 5.56 | 498.1 | | 0.061 | |
| Alzheimer's dementia | T7 | AD | 77 | male | 3.91 | 319.2 | | 0.0361 | 0.0934 |
| Alzheimer's dementia | T8 | AD | 76 | male | 5.22 | 607.1 | | 0.0807 | 0.1438 |
| Alzheimer's dementia | T9 | AD | 83 | male | 8.35 | 1844.2 | | 0.192 | 0.3362 |
| Alzheimer's dementia | T10 | AD | 65 | male | 2.34 | 419.2 | | 0.0746 | 0.1616 |
| Alzheimer's dementia | T11 | AD | 61 | fem. | 4.85 | 481.3 | | 0.0555 | 0.1032 |
| Alzheimer's dementia | T12 | AD | 76 | fem. | 4.57 | 356.3 | | 0.0535 | 0.1038 |
| Alzheimer's dementia | T14 | AD | 71 | male | 2.67 | 377.5 | | 0.0656 | 0.2175 |
| Alzheimer's dementia | T15 | AD | 63 | male | 3.75 | 290 | | 0.0509 | 0.1134 |
| Alzheimer's dementia | T16 | AD | 85 | fem. | 4.21 | 515.8 | | 0.0647 | 0.139 |
| Alzheimer's dementia | T18 | AD | 66 | fem. | 6.56 | 542.9 | | 0.0577 | 0.1007 |
| Alzheimer's dementia | T19 | AD | 76 | male | 4.03 | 586.9 | | 0.0465 | |
| Alzheimer's dementia | T20 | AD | 82 | fem. | 5.43 | 1628.3 | | 0.1186 | 0.2001 |
| Alzheimer's dementia | T21 | AD | 59 | fem. | 4.67 | 1036.3 | | 0.0774 | 0.1445 |
| Alzheimer's dementia | T22 | AD | 56 | male | 2.33 | 780 | | 0.0897 | 0.1393 |
| Alzheimer's dementia | T26 | AD | 78 | male | 4.43 | 735.4 | | 0.0509 | 0.1012 |
| Alzheimer's dementia | T30, NP52 | AD | 68 | fem. | 4.49 | 1065.8 | | 0.0773 | 0.1807 |
| Alzheimer's dementia | T32, NP66 | AD | 66 | fem. | 4.32 | 1206.7 | | 0.0809 | 0.2132 |
| Alzheimer's dementia | T33, NP69 | AD | 65 | male | 1.93 | 475 | | 0.0553 | |
| Alzheimer's dementia | T34, NP35 | AD | 75 | male | 3.77 | 300 | | 0.0253 | |
| Alzheimer's dementia | T35, NP37 | AD | 70 | male | 3.56 | 378.8 | | 0.0222 | 0.0624 |

$Aβ SDS-PAGE/immunoblot after immunoprecipitation
*Ratio of area units

TABLE 13

Aβ SDS-PAGE/immunoblot 1 of Aβ peptides in human lumbar CSF in NDC-1 and AD-1 after the samples have been directly taken up in SDS-PAGE sample buffer or after previous immunoprecipitation (subgroup). In addition, the $A\beta_{1-42}$ concentration in the CSF in AD-1 was measured using a commercial ELISA $_{A\beta1-42}$; statistical characteristics: valid N, mean, 95% confidence interval, median, lower/upper quartile, standard deviation

|  | Group | Valid N | Mean | Confid. −95% | Confid. +95% | Median | Lower quartile | Upper quartile | S.D. |
|---|---|---|---|---|---|---|---|---|---|
| AGE | AD | 35 | 69.7 | 66.7 | 72.7 | 68.0 | 64.7 | 76.0 | 8.7 |
|  | NDC | 30 | 63.5 | 58.2 | 68.9 | 66.9 | 56.3 | 74.4 | 14.2 |
| $A\beta_{1-40}$ | AD | 35 | 5.6 | 4.1 | 7.1 | 4.6 | 3.7 | 6.0 | 4.4 |
| (ng/ml) | NDC | 30 | 7.6 | 6.2 | 9.0 | 6.6 | 4.9 | 10.4 | 3.7 |
| $A\beta_{1-42}$ | AD | 35 | 721.2 | 575.0 | 867.5 | 607.1 | 419.2 | 925.8 | 425.7 |
| (pg/ml) | NDC | 30 | 1677.5 | 1384.0 | 1970.9 | 1533.3 | 1040.6 | 2009.2 | 785.9 |
| $A\beta_{1-42}$, IP, | AD | 10 | 320.7 | 215.0 | 426.4 | 317.4 | 206.3 | 373.0 | 147.7 |
| (pg/ml)$^\$$ | NDC | 20 | 457.5 | 380.4 | 534.6 | 411.6 | 356.1 | 557.8 | 164.8 |
| $A\beta_{1-42}$ ELISA$^1$ (pg/ml) | AD | 35 | 412.4 | 361.1 | 463.7 | 371.0 | 316.0 | 445.0 | 149.3 |
| $A\beta_{1-37}$ | AD | 35 | 1031.8 | 794.0 | 1269.6 | 840.3 | 660.0 | 1243.3 | 692.3 |
| (FE*) | NDC | 30 | 1517.8 | 1173.1 | 1862.5 | 1299.7 | 759.7 | 2375.0 | 923.1 |
| $A\beta_{1-38}$ | AD | 35 | 3975.3 | 3445.1 | 4505.5 | 3931.7 | 2977.3 | 4907.7 | 1543.5 |
| (FE*) | NDC | 30 | 5123.3 | 4420.2 | 5826.3 | 5035.3 | 3421.7 | 6658.3 | 1882.8 |
| $A\beta_{1-39}$ | AD | 35 | 942.8 | 749.5 | 1136.2 | 923.0 | 545.7 | 1186.7 | 562.7 |
| (FE*) | NDC | 30 | 1389.1 | 1101.9 | 1676.2 | 1178.7 | 726.0 | 2115.0 | 769.0 |
| $A\beta_{1-40}$ | AD | 35 | 8499.1 | 7841.0 | 9157.3 | 8293.0 | 7545.5 | 9335.0 | 1916.0 |
| (FE*) | NDC | 30 | 9748.3 | 9007.0 | 10489.5 | 9689.8 | 8556.0 | 11384.0 | 1985.2 |
| $A\beta_{1-42}$ | AD | 35 | 732.7 | 539.7 | 925.6 | 563.3 | 416.3 | 811.7 | 561.6 |
| (FE*) | NDC | 30 | 2003.1 | 1556.7 | 2449.5 | 1864.2 | 908.7 | 2593.7 | 1195.5 |
| $A\beta_{42}/$ | AD | 35 | 0.0803 | 0.0657 | 0.0948 | 0.0656 | 0.0535 | 0.0897 | 0.0424 |
| $A\beta_{40}$** | NDC | 30 | 0.1947 | 0.1603 | 0.2291 | 0.1848 | 0.1112 | 0.2569 | 0.0922 |
| $A\beta_{42}/$ | AD | 31 | 0.1847 | 0.1532 | 0.2163 | 0.1616 | 0.1145 | 0.2132 | 0.0861 |
| $A\beta_{38}$** | NDC | 29 | 0.3853 | 0.3302 | 0.4404 | 0.4065 | 0.2753 | 0.4919 | 0.1448 |

$^\$$Aβ SDS-PAGE/immunoblot after immunoprecipitation (mAb 6E10)
*Area units
**Ratio of area units
[1]Hulstaert et al., 1999, Neurology 52: 1555–62.

TABLE 14

Comparison of the AD-1 and NDC-1 patient groups by the Mann-Whitney U test

|  | AD-1 (n) | NDC-1 (n) | p level |
|---|---|---|---|
| AGE | 35 | 30 | 0.1098 |
| $A\beta_{1-40}$ | 35 | 30 | 0.0055 |
| $A\beta_{1-42}$ | 35 | 30 | 1.23E−07 |
| $A\beta_{1-42}$ IP$^\$$ | 10 | 20 | 0.0387 |
| $A\beta_{42}/A\beta_{40}$* | 35 | 30 | 4.77E−08 |
| $A\beta_{42}/A\beta_{38}$* | 31 | 29 | 3.49E−07 |

$^\$$Aβ SDS-PAGE/immunoblot after immunoprecipitation (mAb 6E10)
*Ratio of area units

TABLE 15

Synopsis of the diagnostic characteristics (specificity, sensitivity, max. Youden index, concentration limits) for für $A\beta_{1-42}$ and relevant Aβ peptide ratios for differentiating the AD-1 and NDC-1 patient groups.

|  | Limit | Specificity | Sensitivity | Maximum Youden index |
|---|---|---|---|---|
| $A\beta_{1-42}$ (pg/ml) | 802.5 | 0.74 | 0.87 | 0.61 |
| $A\beta_{42}/A\beta_{40}$* | 0.086 | 0.71 | 0.93 | 0.65 |
| $A\beta_{42}/A\beta_{38}$* | 0.231 | 0.84 | 0.86 | 0.70 |

*Ratio of area units

TABLE 16a

Aβ SDS-PAGE/immunoblot 1 on $A\beta_{1-42}$ and $A\beta_{1-40}$ in CSF, NDC-2$^{CP}$ group: Comparison of cryoprecipitation after freezing of untreated CSF samples (native*) versus pretreatment with SDS/thermal denaturation (SDS**).

| Patients | Diagnosis | $A\beta_{1-42}$SDS** pg/ml | $A\beta_{1-40}$SDS** pg/ml | $A\beta_{42}/A\beta_{40}$SDS** | $A\beta_{1-42}$native* pg/ml | $A\beta_{1-40}$native* pg/ml | $A\beta_{42}/A\beta_{40}$native* |
|---|---|---|---|---|---|---|---|
| NP51 | Anxiety disorder | 1543.0 | 7830.0 | 0.1971 | 856.3 | 7473.0 | 0.1146 |
| NP53 | Epilepsy | 1888.0 | 7869.0 | 0.2399 | 1348.3 | 7714.0 | 0.1748 |
| NP47 | Homer syndrome | 1588.7 | 7753.3 | 0.2049 | 991.7 | 7156.7 | 0.1386 |
| NP48 | Depression | 1926.3 | 7911.3 | 0.2435 | 1128.0 | 6821.7 | 0.1654 |
| NP54 | Prolapsed disc (TS) | 1387.3 | 5257.0 | 0.2639 | 1277.0 | 5032.7 | 0.2537 |

TABLE 16a-continued

Aβ SDS-PAGE/immunoblot 1 on $A\beta_{1-42}$ and $A\beta_{1-40}$ in CSF, NDC-$2^{CP}$ group: Comparison of cryoprecipitation after freezing of untreated CSF samples (native*) versus pretreatment with SDS/thermal denaturation (SDS**).

| Patients | Diagnosis | $A\beta_{1-42}$SDS** pg/ml | $A\beta_{1-40}$SDS** pg/ml | $A\beta_{42}/A\beta_{40}$SDS** | $A\beta_{1-42}$native* pg/ml | $A\beta_{1-40}$native* pg/ml | $A\beta_{42}/A\beta_{40}$native* |
|---|---|---|---|---|---|---|---|
| NP55 | Cerebral ischemia | 2578.0 | 7985.0 | 0.3229 | 1707.0 | 8103.7 | 0.2106 |
| NP56 | Depression | 2183.3 | | | 1437.7 | | |
| NP57 | Catatonic sydrome | 1477.7 | 4292.0 | 0.3443 | 1261.7 | 4744.3 | 0.2659 |
| NP59 | Primary progressive dementia, etiology uncl. | 2285.3 | 8377.7 | 0.2728 | 1734.7 | 7942.0 | 0.2184 |
| NP60 | Neurosarcoidosis | 965.7 | 6818.0 | 0.1416 | 653.0 | 6411.7 | 0.1018 |
| Mean | | 1782.3 | 7121.5 | 0.2479 | 1239.5 | 6822.2 | 0.1827 |
| SD | | 457.1 | 1332.6 | 0.0592 | 328.8 | 1150.6 | 0.0553 |
| CV | | 25.6 | 18.7 | 23.9 | 26.5 | 16.9 | 30.3 |

TABLE 16b

Absolute and percentage reduction caused by cryoprecipitation in $A\beta_{1-40}$, $A\beta_{1-42}$ in the Aβ peptide ratio for the NDC-$2^{CP}$ group (table of differences from table 10a)

| Patients | Diagnosis | $\Delta A\beta_{1-42}$ | $\Delta A\beta_{1-42}\%$* | $\Delta A\beta_{1-40}$ | $\Delta A\beta_{1-40}\%$* | $\Delta A\beta_{42}/A\beta_{40}$ | $\Delta A\beta_{42}/A\beta_{40}\%$* |
|---|---|---|---|---|---|---|---|
| NP51 | Anxiety disorder | −686.7 | −44.5 | −357.0 | −4.6 | −0.0825 | −41.9 |
| NP53 | Epilepsy | −539.7 | −28.6 | −155.0 | −2.0 | −0.0651 | −27.1 |
| NP47 | Homer syndrome | −597.0 | −37.6 | −596.7 | −7.7 | −0.0663 | −32.4 |
| NP48 | Depression | −798.3 | −41.4 | −1089.7 | −13.8 | −0.0781 | −32.1 |
| NP54 | Prolapsed disc (TS) | −110.3 | −8.0 | −224.3 | −4.3 | −0.0102 | −3.8 |
| NP55 | Cerebral ischemia | −871.0 | −33.8 | 118.7 | 1.5 | −0.1122 | −34.8 |
| NP56 | Depression | −745.7 | −34.2 | | | | |
| NP57 | Catatonic syndrome | −216.0 | −14.6 | 452.3 | 10.5 | −0.0784 | −22.8 |
| NP59 | Primary progressive dementia, etiology uncl. | −550.7 | −24.1 | −435.7 | −5.2 | −0.0544 | −19.9 |
| NP60 | Neurosarcoidosis | −312.7 | −32.4 | −406.3 | −6.0 | −0.0398 | −28.1 |
| MW | | −542.8 | −29.9 | −299.3 | −3.5 | −0.0652 | −27.0 |
| SD | | 241.8 | 10.9 | 410.0 | 6.3 | 0.0272 | 10.2 |
| VK | | 44.5 | 36.6 | 137.0 | 180.8 | 41.7 | 37.9 |

*$\Delta A\beta_{Peptide}\% = (A\beta_{Peptide}\text{Native} - A\beta_{Peptide}\text{SDS}) / A\beta_{Peptide}\text{SDS} * 100$:
Negative (positive) $\Delta A\beta_{1-42}$ or $\Delta A\beta_{1-40}$ means lower (higher) Aβ peptide concentration in the CSF sample which has been frozen untreated relative to pretreatment of the sample with SDS/thermal denaturation

TABLE 17

The level of significance of the reduction caused by cryoprecipitation in the Aβ peptides was determined for the NDC-$2^{CP}$ group by the Wilcoxon test for paired samples (cf. table 10a):

| $A\beta_{1-42}$SDS versus $A\beta_{1-42}$native | $A\beta_{1-40}$SDS versus $A\beta_{1-40}$native | $A\beta_{42}/A\beta_{40}$SDS versus $A\beta_{42}/A\beta_{40}$native | |
|---|---|---|---|
| 10 | 9 | 9 | n |
| 0.0051 | 0.0858 | 0.0077 | p level |

TABLE 18a

Intraassay coefficient of variation for Aβ SDS-PAGE/immunoblot 2 using Rotiblock and ECL detection by CCD camera. The Aβ peptides were each loaded in quadruplicate on each Western immunoblot (M1–M4).

| | 80 pg | | | | | 20 pg | | | | |
|---|---|---|---|---|---|---|---|---|---|---|
| | $A\beta_{1-38}$ | $A\beta_{1-40}$ | $A\beta_{1-42}$ | $A\beta_{42}/A\beta_{40}$ | $A\beta_{42}/A\beta_{38}$ | $A\beta_{1-38}$ | $A\beta_{1-40}$ | $A\beta_{1-42}$ | $A\beta_{42}/A\beta_{40}$ | $A\beta_{42}/A\beta_{38}$ |
| Intraassay CV M1 | 5.47 | 4.47 | 4.28 | 2.32 | 2.14 | 5.34 | 5.92 | 3.15 | 6.22 | 7.48 |

TABLE 18a-continued

Intraassay coefficient of variation for Aβ SDS-PAGE/immunoblot 2 using Rotiblock and ECL detection by CCD camera. The Aβ peptides were each loaded in quadruplicate on each Western immunoblot (M1–M4).

|  | 80 pg | | | | | 20 pg | | | | |
|---|---|---|---|---|---|---|---|---|---|---|
|  | $A\beta_{1-38}$ | $A\beta_{1-40}$ | $A\beta_{1-42}$ | $A\beta_{42}/A\beta_{40}$ | $A\beta_{42}/A\beta_{38}$ | $A\beta_{1-38}$ | $A\beta_{1-40}$ | $A\beta_{1-42}$ | $A\beta_{42}/A\beta_{40}$ | $A\beta_{42}/A\beta_{38}$ |
| Intraassay CV M2 | 6.19 | 4.05 | 5.90 | 4.02 | 4.68 | 4.41 | 8.88 | 8.97 | 3.67 | 7.92 |
| Intraassay CV M3 | 5.75 | 5.39 | 2.59 | 5.43 | 5.52 | 12.82 | 4.12 | 1.27 | 3.01 | 12.21 |
| Intraassay CV M4 | 6.16 | 6.79 | 2.87 | 4.28 | 4.53 | 2.20 | 4.90 | 4.86 | 2.63 | 5.27 |
| Mean intraassay CV | 5.89 | 5.18 | 3.91 | 4.01 | 4.22 | 6.19 | 5.95 | 4.56 | 3.88 | 8.22 |
| SD intraassay CV | 0.30 | 1.05 | 1.32 | 1.11 | 1.26 | 3.99 | 1.80 | 2.84 | 1.40 | 2.51 |

TABLE 18b

Interassay coefficient of variation for Aβ SDS-PAGE/immunoblot 2 using Rotiblock and ECL detection by CCD camera. The measurements are based on the volume data sets of a band after background correction and correspond to the means (mean) of a quadruplicate determination on each Western immunoblot (cf. table xx). The Western immunoblots (M1–M4) correspond to independently performed electrophoreses.

|  | 80 pg | | | | | 20 pg | | | | |
|---|---|---|---|---|---|---|---|---|---|---|
|  | $A\beta_{1-38}$ | $A\beta_{1-40}$ | $A\beta_{1-42}$ | $A\beta_{42}/A\beta_{40}$ | $A\beta_{42}/A\beta_{38}$ | $A\beta_{1-38}$ | $A\beta_{1-40}$ | $A\beta_{1-42}$ | $A\beta_{42}/A\beta_{40}$ | $A\beta_{42}/A\beta_{38}$ |
| Mean M1 | 46452.20 | 52114.60 | 28568.20 | 0.55 | 0.62 | 6817.50 | 7106.25 | 2963.50 | 0.42 | 0.44 |
| Mean M2 | 46415.80 | 51925.00 | 27217.20 | 0.52 | 0.59 | 6622.50 | 6774.00 | 3253.75 | 0.48 | 0.49 |
| Mean M3 | 51619.25 | 55606.75 | 30266.50 | 0.55 | 0.59 | 7430.75 | 7544.25 | 3028.00 | 0.40 | 0.41 |
| MW M4 | 45169.00 | 50431.50 | 29304.00 | 0.58 | 0.65 | 7511.00 | 8251.60 | 3767.60 | 0.46 | 0.50 |
| Total Mean | 47414.06 | 52519.46 | 28838.98 | 0.55 | 0.61 | 7095.44 | 7419.03 | 3253.21 | 0.44 | 0.46 |
| SD | 2482.22 | 1897.91 | 1113.28 | 0.02 | 0.03 | 382.77 | 552.89 | 315.93 | 0.03 | 0.04 |
| Interassay CV | 5.24 | 3.61 | 3.86 | 3.81 | 4.23 | 5.39 | 7.45 | 9.71 | 7.09 | 8.02 |

TABLE 19

Aβ SDS-PAGE/immunoblot 2 Aβ peptides in human CSF in NDC-3 and AD-3

| P CODE | Age | Sex | Diagnosis | D Code | MMSE[1] | $A\beta_{1-42}$ ELISA[2] (ng/ml) | $A\beta_{1-37}$ (ng/ml) | $A\beta_{1-38}$ (ng/ml) | $A\beta_{1-39}$ (ng/ml) | $A\beta_{1-40}$ (ng/ml) | $A\beta_{1-42}$ (ng/ml) |
|---|---|---|---|---|---|---|---|---|---|---|---|
| NP207 | 76 | M | Polyneuropathy | NDC (OND) | 29 |  | 1.20 | 2.68 | 1.44 | 11.38 | 1.95 |
| NP208 | 65 | F | Meningoencephalitis | NDC (ONO) | 30 |  | 1.68 | 3.37 | 1.48 | 13.44 | 2.14 |
| NP213 | 32 | M | Depressive disorder with psychotic features | NDC (OND) | 30 | 0.72 | 1.23 | 2.66 | 1.33 | 10.72 | 2.07 |
| NP230 | 38 | F | Epilepsy | NDC (OND) | 30 |  | 1.08 | 2.36 | 1.10 | 8.18 | 1.44 |
| NP231 | 42 | M | Epilepsy | NDC (OND) | 30 |  | 1.34 | 3.04 | 1.46 | 12.19 | 2.21 |
| NP234 | 28 | F | Embolic transient ischemic brain stem attacks | NDC (OND) | 30 |  | 1.13 | 2.42 | 1.15 | 9.43 | 1.39 |
| NP235 | 19 | M | Psychotic disorder (unspecified) and mild cognitive disorder | NDC (OND) | 28 |  | 1.64 | 3.28 | 1.77 | 14.24 | 4.12 |
| NP237 | 76 | F | Subcortical arteriosclerotic encephalopathy | NDC (OND) | 30 |  | 1.22 | 2.47 | 1.10 | 8.73 | 1.29 |
| NP243 | 47 | F | Depressive disorder | NDC (OND) | 29 |  | 1.21 | 2.53 | 1.13 | 9.28 | 1.77 |
| NP271 | 31 | M | Meniere's disease | NDC (OND) | 30 |  | 1.60 | 3.49 | 1.48 | 12.82 | 2.46 |
| NP272 | 52 | M | Benign paroxysmal postural vertigo | NDC (OND) | 30 |  | 1.23 | 2.71 | 1.11 | 10.53 | 1.97 |
| NP274 | 59 | M | Multiple sclerosis | NDC (CID) | 27 |  | 1.02 | 2.14 | 0.96 | 7.29 | 1.25 |
| NP120 | 30 | M | Generalized anxiety disorder | NDC (OND) | 30 | 1.17 | 2.29 | 4.56 | 2.23 | 19.38 | 4.26 |
| NP121 | 37 | M | Benzodiazepine dependence | NDC (OND) | 30 | 0.81 | 1.12 | 2.40 | 1.09 | 10.47 | 1.97 |
| NP123 | 61 | F | Subcortical arteriosclerotic encephalopathy | NDC (OND) | 30 | 0.91 | 1.58 | 3.57 | 1.68 | 14.54 | 3.08 |
| NP238 | 54 | M | Severe cradiocerebral trauma with hydrocephalus and post-traumatic epilepsy | NDC (OND) | 25 |  | 0.85 | 1.77 | 0.96 | 7.82 | 1.44 |
| NP245 | 36 | M | Tension headache | NDC (OND) | 30 |  | 0.99 | 2.23 | 1.00 | 10.20 | 1.81 |
| NP268 | 63 | M | Chronic inflammatory CNS disorder | NDC (CID) | 30 |  | 0.77 | 1.56 | 0.74 | 5.18 | 1.00 |
| NP276 | 38 | M | Subcortical arteriosclerotic encephalopathy | NDC (OND) | 30 |  | 1.34 | 2.93 | 1.48 | 11.87 | 1.97 |
| NP278 | 56 | M | Post-traumatic epilepsy | NDC (OND) | 24 |  | 2.46 | 5.26 | 2.76 | 20.02 | 4.85 |
| NP101 | 67 | M | Depressive disorder and mild cognitive disorder | NDC (OND) | 30 |  | 1.29 | 2.91 | 1.46 | 13.09 | 2.22 |
| NP110 | 39 | M | Depressive disorder | NDC (OND) | 30 | 0.94 | 1.45 | 3.11 | 1.76 | 13.10 | 2.49 |
| NP119 | 45 | F | Depressive disorder | NDC (OND) | NA | 1.27 | 2.24 | 5.12 | 2.99 | 20.93 | 4.62 |
| NP290 | 19 | M | Manic episodes with psychotic | NDC (OND) | 30 |  | 1.26 | 2.71 | 1.27 | 10.53 | 1.81 |

TABLE 19-continued

Aβ SDS-PAGE/immunoblot 2 Aβ peptides in human CSF in NDC-3 and AD-3

| | | | | | | | | | | | |
|---|---|---|---|---|---|---|---|---|---|---|---|
| | | | features in Type 1 bipolar affective psychosis | | | | | | | | |
| NP292 | 70 | F | Brain metastasis | NDC (OND) | 27 | | 0.96 | 2.27 | 0.95 | 7.57 | 1.43 |
| NP296 | 51 | M | Motor neurone disease | NDC (OND) | 30 | | 2.31 | 5.51 | 2.46 | 19.46 | 4.58 |
| NP297 | 46 | F | Multiple sclerosis | NDC (CID) | 30 | 0.83 | 1.33 | 3.33 | 1.46 | 12.96 | 2.08 |
| NP300 | 31 | F | Sinus thrombosis with recurrent transient ischemic attacks | NDC (OND) | 30 | 0.18 | 0.70 | 1.45 | 0.74 | 4.35 | 0.88 |
| NP309 | 39 | F | Neurological disorder (unspecified) without dementia | NDC (OND) | 30 | 0.47 | 1.24 | 2.71 | 1.11 | 10.42 | 1.63 |
| NP352 | 45 | F | Chronic inflammatory CNS disorder | NDC (CID) | 29 | 0.67 | 2.51 | 5.92 | 2.63 | 19.38 | 4.59 |
| NP428 | 17 | F | Cranial trauma | NDC (OND) | NA | 0.43 | 1.16 | 2.47 | 1.11 | 9.24 | 1.33 |
| NP330 | 56 | M | Motor neurone disease | NDC (OND) | NA | 0.73 | 1.09 | 2.45 | 1.15 | 10.08 | 2.16 |
| NP344 | 36 | F | Somatoform (conversion neurotic) disorder | NDC (OND) | 28 | 0.59 | 1.18 | 2.67 | 1.23 | 10.86 | 2.01 |
| NP345 | 34 | M | Panic disorder with agoraphobia | NDC (OND) | NA | 0.68 | 1.60 | 3.59 | 1.87 | 15.11 | 2.88 |
| NP355 | 31 | F | Cerebral transient ischemic attacks | NDC (OND) | 30 | 0.78 | 2.54 | 5.23 | 2.73 | 20.22 | 4.93 |
| NP356 | 65 | F | Polycythemia vera with transient ischemic attacks | NDC (OND) | 30 | 0.64 | 0.97 | 2.15 | 1.10 | 8.92 | 1.29 |
| NP364 | 58 | M | Epilepsy | NDC (OND) | 28 | 0.79 | 1.40 | 3.08 | 1.59 | 13.28 | 2.45 |
| NP374 | 43 | M | Chronic inflammatory CNS disorder | NDC (CID) | 30 | 0.76 | 1.12 | 2.49 | 1.17 | 9.32 | 1.56 |
| NP402 | 66 | F | Hemicrania | NDC (OND) | 30 | 0.51 | 1.15 | 2.78 | 1.28 | 11.62 | 1.71 |
| NP412 | 48 | M | Depressive disorder associated with subcortical arterlosclerotic encephalopathy | NDC (OND) | 30 | 0.54 | 1.07 | 2.44 | 1.06 | 9.75 | 1.56 |
| NP419 | 46 | M | Chronic inflammatory CSN disorder | NDC (CID) | NA | 0.39 | 0.93 | 2.36 | 1.11 | 8.43 | 1.41 |
| NP421 | 60 | M | Chronic inflammatory CSN disorder with primary progressive aphasia | NDC (CID) | 30 | 0.54 | 1.34 | 3.12 | 1.42 | 11.90 | 2.15 |
| NP456 | 42 | F | Chronic inflammatory CSN disorder | NDC (CID) | 27 | 0.6754 | 1.93 | 5.09 | 2.56 | 18.81 | 3.72 |
| NP457 | 24 | M | Depressive episodes in Type 1 bipolar affective psychosis | NDC (OND) | 30 | 0.7451 | 1.23 | 2.93 | 1.78 | 12.65 | 2.16 |
| NP466 | 25 | F | Chronic inflammatory CSN process | NDC (CID) | 30 | 0.7456 | 1.16 | 3.3 | 1.94 | 14.24 | 2.38 |
| NP490 | 20 | M | Chronic inflammatory CSN process | NDC (CID) | 30 | 0.7196 | 2.33 | 6.18 | 2.64 | 20.27 | 4.35 |
| NP526 | 61 | M | Depressive disorder associated with subcortical arteriosclerotic encephalopathy | NDC (OND) | 29 | 0.82 | 1.62 | 4.53 | 2.28 | 18.40 | 3.40 |
| NP37 | 71 | M | Alzheimer's dementia | AD | 17 | | 1.37 | 3.11 | 1.37 | 11.94 | 0.94 |
| NP45 | 76 | F | Alzheimer's dementia | AD | 5 | | 1.04 | 2.40 | 1.05 | 11.55 | 1.48 |
| NP52 | 68 | F | Alzheimer's dementia | AD | 11 | | 1.65 | 3.73 | 2.00 | 14.21 | 1.59 |
| NP66 | 87 | F | Alzheimer's dementia | AD | 1 | | 1.22 | 3.08 | 1.34 | 13.05 | 1.50 |
| NP112 | 77 | F | Alzheimer's dementia | AD | 14 | | 1.23 | 2.95 | 1.36 | 12.58 | 1.55 |
| NP190 | 79 | F | Alzheimer's dementia | AD | 19 | | 0.80 | 1.77 | 0.85 | 6.40 | 0.66 |
| NP143 | 55 | M | Alzheimer's dementia | AD | 27 | | 0.88 | 1.75 | 0.79 | 6.38 | 0.89 |
| NP58 | 83 | F | Alzheimer's dementia | AD | 20 | | 2.27 | 4.92 | 2.61 | 19.46 | 2.07 |
| NP319 | 72 | F | Alzheimer's dementia | AD | 28 | | 1.01 | 2.42 | 1.25 | 9.08 | 0.87 |
| NP320 | 70 | F | Alzheimer's dementia | AD | 25 | | 1.97 | 4.50 | 2.26 | 17.28 | 1.55 |
| NP111 | 84 | F | Alzheimer's dementia | AD | 15 | | 3.02 | 7.18 | 3.49 | 25.39 | 2.02 |
| NP126 | 74 | M | Alzheimer's dementia | AD | 8 | | 1.38 | 3.38 | 1.33 | 13.63 | 1.48 |

| P CODE | Total Aβ[3] (ng/ml) | $Aβ_{1-37}$[4] (%) | $Aβ_{1-38}$[4] (%) | $Aβ_{1-39}$[4] (%) | $Aβ_{1-40}$[4] (%) | $Aβ_{1-42}$[4] (%) | $R_{42/40}$[5] | $R_{42/38}$[5] | $R_{38/40}$[5] | ApoE[6] |
|---|---|---|---|---|---|---|---|---|---|---|
| NP207 | 18.66 | 6.44 | 14.37 | 7.71 | 61.01 | 10.47 | 0.1717 | 0.7290 | 0.2355 | 3/3 |
| NP208 | 22.11 | 7.61 | 15.26 | 6.71 | 60.78 | 9.66 | 0.1590 | 0.6332 | 0.2511 | 3/3 |
| NP213 | 18.00 | 6.82 | 14.77 | 7.38 | 59.54 | 11.48 | 0.1928 | 0.7772 | 0.2481 | 3/3 |
| NP230 | 14.16 | 7.62 | 16.64 | 7.79 | 57.76 | 10.19 | 0.1764 | 0.6124 | 0.2881 | 3/3 |
| NP231 | 20.24 | 6.62 | 15.02 | 7.20 | 60.23 | 10.93 | 0.1815 | 0.7277 | 0.2495 | 3/3 |
| NP234 | 15.52 | 7.30 | 15.82 | 7.43 | 60.73 | 8.93 | 0.1471 | 0.5720 | 0.2571 | 3/3 |
| NP235 | 25.04 | 6.56 | 13.10 | 7.05 | 56.85 | 16.43 | 0.2891 | 1.2543 | 0.2305 | 2/3 |
| NP237 | 14.82 | 8.21 | 16.70 | 7.43 | 58.94 | 8.72 | 0.1480 | 0.5224 | 0.2833 | 3/4 |
| NP243 | 15.92 | 7.61 | 15.88 | 7.10 | 58.31 | 11.10 | 0.1903 | 0.6988 | 0.2724 | 3/3 |
| NP271 | 21.84 | 7.33 | 15.97 | 6.76 | 58.68 | 11.25 | 0.1916 | 0.7041 | 0.2722 | 3/3 |
| NP272 | 17.55 | 7.00 | 15.44 | 6.33 | 60.03 | 11.20 | 0.1866 | 0.7252 | 0.2573 | 3/3 |
| NP274 | 12.65 | 8.04 | 16.89 | 7.57 | 57.63 | 9.87 | 0.1713 | 0.5848 | 0.2931 | 3/4 |
| NP120 | 32.72 | 7.00 | 13.94 | 6.83 | 59.22 | 13.01 | 0.2197 | 0.9338 | 0.2354 | 3/3 |
| NP121 | 17.05 | 6.58 | 14.07 | 6.42 | 61.38 | 11.55 | 0.1881 | 0.8208 | 0.2292 | NA |
| NP123 | 24.45 | 6.47 | 14.58 | 6.86 | 59.48 | 12.60 | 0.2119 | 0.8642 | 0.2452 | 3/3 |
| NP238 | 12.83 | 6.60 | 13.82 | 7.45 | 60.93 | 11.20 | 0.1838 | 0.8106 | 0.2267 | 2/3 |
| NP245 | 16.22 | 6.11 | 13.73 | 6.14 | 62.87 | 11.15 | 0.1773 | 0.8120 | 0.2184 | 3/3 |
| NP268 | 9.26 | 8.36 | 16.88 | 8.03 | 55.94 | 10.78 | 0.1928 | 0.6388 | 0.3018 | 3/3 |
| NP276 | 19.80 | 6.85 | 14.96 | 7.58 | 60.58 | 10.05 | 0.1660 | 0.6716 | 0.2471 | 2/4 |
| NP278 | 35.34 | 6.97 | 14.87 | 7.81 | 56.64 | 13.71 | 0.2421 | 0.9218 | 0.2626 | 3/3 |
| NP101 | 20.97 | 6.17 | 13.90 | 6.96 | 62.40 | 10.58 | 0.1695 | 0.7610 | 0.2227 | 3/3 |

TABLE 19-continued

Aβ SDS-PAGE/immunoblot 2 Aβ peptides in human CSF in NDC-3 and AD-3

| | | | | | | | | | | |
|---|---|---|---|---|---|---|---|---|---|---|
| NP110 | 21.92 | 6.62 | 14.20 | 8.03 | 59.79 | 11.36 | 0.1901 | 0.8002 | 0.2375 | 3/3 |
| NP119 | 35.90 | 6.23 | 14.27 | 8.34 | 58.30 | 12.87 | 0.2208 | 0.9017 | 0.2448 | 2/3 |
| NP290 | 17.57 | 7.18 | 15.40 | 7.22 | 59.93 | 10.28 | 0.1715 | 0.6673 | 0.2570 | 3/3 |
| NP292 | 13.19 | 7.31 | 17.21 | 7.22 | 57.41 | 10.86 | 0.1891 | 0.6307 | 0.2996 | 3/3 |
| NP296 | 34.32 | 6.72 | 16.06 | 7.17 | 56.71 | 13.33 | 0.2351 | 0.8303 | 0.2831 | 3/3 |
| NP297 | 21.16 | 6.30 | 15.75 | 6.68 | 61.26 | 9.82 | 0.1603 | 0.6234 | 0.2571 | 3/3 |
| NP300 | 8.12 | 8.64 | 17.83 | 9.16 | 53.59 | 10.78 | 0.2012 | 0.6048 | 0.3326 | 3/4 |
| NP309 | 17.11 | 7.27 | 15.82 | 6.48 | 60.91 | 9.52 | 0.1564 | 0.6019 | 0.2598 | 2/3 |
| NP352 | 35.02 | 7.17 | 16.89 | 7.50 | 55.34 | 13.10 | 0.2368 | 0.7759 | 0.3052 | 3/3 |
| NP428 | 15.30 | 7.58 | 16.15 | 7.23 | 6O.38 | 8.66 | 0.1434 | 0.5362 | 0.2675 | 3/4 |
| NP330 | 16.93 | 6.46 | 14.48 | 6.77 | 59.54 | 12.75 | 0.2142 | 0.8808 | 0.2432 | 3/3 |
| NP344 | 17.94 | 6.58 | 14.86 | 6.85 | 60.50 | 11.21 | 0.1853 | 0.7545 | 0.2457 | 3/3 |
| NP345 | 24.85 | 6.43 | 14.44 | 8.72 | 60.82 | 11.59 | 0.1905 | 0.8023 | 0.2375 | 3/3 |
| NP355 | 35.65 | 7.11 | 14.68 | 7.67 | 56.71 | 13.83 | 0.2439 | 0.9424 | 0.2589 | 3/3 |
| NP356 | 14.42 | 6.70 | 14.90 | 7.62 | 61.85 | 8.91 | 0.1441 | 0.5960 | 0.2410 | 3/4 |
| NP364 | 21.80 | 6.41 | 14.13 | 7.31 | 60.91 | 11.24 | 0.1845 | 0.7951 | 0.2320 | 2/3 |
| NP374 | 15.66 | 7.14 | 15.91 | 7.48 | 59.49 | 9.98 | 0.1677 | 0.6272 | 0.2674 | 3/4 |
| NP402 | 18.55 | 6.20 | 15.00 | 8.90 | 62.66 | 9.24 | 0.1475 | 0.6161 | 0.2395 | 3/4 |
| NP412 | 15.88 | 6.76 | 15.36 | 8.69 | 61.36 | 9.82 | 0.1601 | 0.6394 | 0.2504 | 3/3 |
| NP419 | 14.24 | 6.51 | 16.57 | 7.80 | 59.21 | 9.91 | 0.1674 | 0.5963 | 0.2798 | 3/3 |
| NP421 | 19.92 | 6.72 | 15.64 | 7.12 | 59.75 | 10.77 | 0.1803 | 0.6887 | 0.2518 | 3/3 |
| NP456 | 32.13 | 6.01 | 15.83 | 8.04 | 58.54 | 11.58 | 0.1978 | 0.7308 | 0.2706 | 4/4 |
| NP457 | 20.75 | 5.93 | 14.10 | 8.59 | 6O.95 | 10.43 | 0.1712 | 0.7372 | 0.2316 | 2/3 |
| NP466 | 23.02 | 5.06 | 14.33 | 8.44 | 61.82 | 10.35 | 0.1674 | 0.7212 | 0.2317 | 3/3 |
| NP490 | 35.77 | 6.51 | 17.27 | 7.37 | 56.68 | 12.17 | 0.2146 | 0.7039 | 0.3049 | 3/3 |
| NP526 | 30.23 | 5.35 | 14.99 | 7.56 | 60.87 | 11.24 | 0.1846 | 0.7506 | 0.2462 | 3/3 |
| NP37 | 18.73 | 7.32 | 16.59 | 7.32 | 63.76 | 5.01 | 0.0786 | 0.3020 | 0.2602 | 44 |
| NP45 | 17.50 | 5.93 | 13.71 | 5.99 | 66.00 | 8.36 | 0.1267 | 0.6100 | 0.2077 | 34 |
| NP52 | 23.18 | 7.12 | 16.11 | 8.63 | 61.30 | 6.84 | 0.1116 | 0.4247 | 0.2629 | 34 |
| NP66 | 20.17 | 6.05 | 15.17 | 6.66 | 64.69 | 7.43 | 0.1148 | 0.4897 | 0.2345 | 34 |
| NP112 | 19.68 | 6.27 | 15.01 | 6.93 | 63.92 | 7.87 | 0.1231 | 0.5244 | 0.2347 | 33 |
| NP190 | 10.48 | 7.64 | 16.86 | 8.15 | 61.07 | 6.27 | 0.1027 | 0.3720 | 0.2761 | 34 |
| NP143 | 10.67 | 8.09 | 16.42 | 7.41 | 59.77 | 8.31 | 0.1390 | 0.5059 | 0.2747 | 24 |
| NP58 | 31.32 | 7.25 | 15.69 | 8.32 | 62.12 | 6.62 | 0.1066 | 0.4219 | 0.2526 | 34 |
| NP319 | 14.83 | 8.88 | 18.56 | 8.54 | 82.07 | 5.98 | 0.0960 | 0.3600 | 0.2668 | 44 |
| NP320 | 27.55 | 7.14 | 16.32 | 8.19 | 82.72 | 5.63 | 0.0896 | 0.3451 | 0.2602 | 24 |
| NP111 | 41.10 | 7.34 | 17.48 | 8.49 | 61.77 | 4.92 | 0.0796 | 0.2812 | 0.2830 | 34 |
| NP126 | 21.20 | 6.49 | 15.95 | 6.27 | 64.30 | 6.96 | 0.1066 | 0.4378 | 0.2480 | 34 |

[1] Mini mental status examination
[2] Hulstaert et al., 1999, Neurology 52: 1555–62
[3] Total of Aβ peptide species (ng/ml)
[4] Percentage of respective Aβ peptide species in total Aβ
[5] Aβ Peptide ratios (Aβ SDS-PAGE/immunoblot)
[6] ApoE genotype

TABLE 20

Aβ SDS-PAGE/immunoblot-2; Aβ peptides in CSF, ApoE genotype and MMSE examination results in the NDC-3 and AD-3 patient groups with relevant subgroups.

| Groups | Patients Number M F | MMSE* Score Median p25 p75 | $A\beta_{1-42}$ ELISA& (ng/ml) Median P25 p75 | $A\beta_{1-37}$ (ng/ml) Median P25 p75 | $A\beta_{1-38}$ (ng/ml) Median Median p25 p75 | $A\beta_{1-39}$ (ng/ml) Median p25 p75 | $A\beta_{1-40}$ (ng/ml) Median p25 p75 | $A\beta_{1-42}$ (ng/ml) Median p25 p75 | total $A_\beta^1$ (ng/ml) Median p25 p75 |
|---|---|---|---|---|---|---|---|---|---|
| NDC-3[a] | 47 | 30 | 0.720 | 1.230 | 2.783 | 1.418 | 11.622 | 2.067 | 18.658 |
| | 28 | 29 | 0.545 | 1.119 | 2.440 | 1.107 | 9.319 | 1.560 | 15.664 |
| | 19 | 30 | 0.813 | 1.602 | 3.489 | 1.766 | 14.240 | 2.880 | 24.447 |
| AD-3[b] | 12 | 16.0 | n.a. | 1.303 | 3.083 | 1.354 | 12.814 | 1.489 | 19.925 |
| | 3 | 9.5 | n.a. | 1.022 | 2.412 | 1.149 | 10.318 | 0.912 | 16.069 |
| | 9 | 22.5 | n.a. | 1.809 | 4.115 | 2.128 | 15.743 | 1.569 | 25.363 |
| IP-plasma-3[c] | 5 | 30 | n.a. | 0.034 | 0.047 | 0.050 | 0.330 | 0.080 | 0.540 |
| | 3 | 29 | n.a. | 0.031 | 0.043 | 0.048 | 0.327 | 0.076 | 0.527 |
| | 2 | 30 | n.a. | 0.037 | 0.057 | 0.057 | 0.384 | 0.091 | 0.626 |
| IP-CSF-3[d] | 5 | 30 | n.a. | 1.345 | 2.805 | 1.928 | 13.230 | 2.730 | 22.038 |
| | 3 | 29 | n.a. | 1.272 | 2.689 | 1.544 | 12.192 | 2.041 | 19.587 |
| | 2 | 30 | n.a. | 2.299 | 4.735 | 2.538 | 15.250 | 3.763 | 28.584 |
| SDS-CSF-3[e] | 5 | 30 | n.a. | 1.620 | 4.530 | 2.280 | 18.400 | 3.400 | 30.230 |
| | 3 | 29 | n.a. | 1.230 | 3.300 | 1.940 | 14.240 | 2.380 | 23.020 |
| | 2 | 30 | n.a. | 1.930 | 5.090 | 2.580 | 18.810 | 3.720 | 32.130 |

TABLE 20-continued

Aβ SDS-PAGE/immunoblot-2; Aβ peptides in CSF, ApoE genotype and MMSE examination results in the NDC-3 and AD-3 patient groups with relevant subgroups.

| Groups | $A\beta_{1-37}^2$ (%) Median p25 p75 | $A\beta_{1-38}^2$ (%) Median p25 p75 | $A\beta_{1-39}^2$ (%) Median p25 p75 | $A\beta_{1-40}^2$ (%) Median p25 p75 | $A\beta_{1-42}^2$ (%) Median p25 p75 | $R_{42/40}^3$ Median p25 p75 | $R_{42/38}^3$ Median p25 p75 | $R_{38/40}^3$ Median p25 p75 | ApoE no $e^4$ 1 or 2 $e^4$ n.a. |
|---|---|---|---|---|---|---|---|---|---|
| NDC-3[a] | 6.721 | 15.024 | 7.311 | 59.786 | 10.933 | 0.184 | 0.725 | 0.251 | 37 |
|  | 6.438 | 14.367 | 6.861 | 58.296 | 9.977 | 0.167 | 0.627 | 0.238 | 9 |
|  | 7.268 | 15.972 | 7.668 | 60.908 | 11.581 | 0.198 | 0.802 | 0.272 | 1 |
| AD-3[b] | 7.129 | 16.216 | 7.783 | 62.422 | 6.732 | 0.108 | 0.423 | 0.260 | 1 |
|  | 6.383 | 15.430 | 6.796 | 61.536 | 5.796 | 0.093 | 0.353 | 0.241 | 11 |
|  | 7.331 | 16.575 | 8.401 | 64.113 | 7.648 | 0.119 | 0.498 | 0.271 | 0 |
| IP-plasma-3[c] | 5.877 | 8.722 | 9.181 | 61.604 | 14.598 | 0.237 | 1.708 | 0.142 | 4 |
|  | 5.870 | 8.218 | 8.948 | 61.329 | 14.559 | 0.237 | 1.695 | 0.133 | 1 |
|  | 6.185 | 8.769 | 9.410 | 61.714 | 14.861 | 0.241 | 1.752 | 0.143 | 0 |
| IP-CSF-3[d] | 6.494 | 13.729 | 8.728 | 60.032 | 12.387 | 0.206 | 0.795 | 0.221 | 4 |
|  | 6.104 | 13.582 | 7.882 | 53.350 | 10.769 | 0.173 | 0.793 | 0.218 | 1 |
|  | 8.041 | 16.048 | 8.750 | 62.248 | 13.165 | 0.247 | 0.920 | 0.306 | 0 |
| SDS-CSF-3[e] | 5.929 | 14.990 | 8.037 | 60.865 | 11.238 | 0.185 | 0.732 | 0.246 | 4 |
|  | 5.351 | 14.330 | 7.556 | 58.541 | 10.434 | 0.171 | 0.722 | 0.232 | 1 |
|  | 6.013 | 15.829 | 8.443 | 60.949 | 11.581 | 0.198 | 0.740 | 0.271 | 0 | n.a.: not available
*MMSE examination results unavailable for 5 of the 47 NDC-3 patients
[1]Total Aβ peptide conc.
[2]Proportion of respective Aβ peptide species as a percentage of the total concentration
[3]Aβ peptide ratios
[a]Non-dementing neuropsychiatric control patients
[b]Alzheimer's dementia
[&]Hulstaert et al., 1999, Neurology 52: 1555–62
[c,d]Immunoprecipitation and Aβ SDS-PAGE/immunoblot 2 of paired [c]plasma/
[d]CSF samples for five patients from the NDC-3 group
[e]SDS/thermal denaturation with Aβ SDS-PAGE/immunoblot 2 of CSF samples from the five NDC-3 patients for whom paired plasma/CSF samples are available

TABLE 21

Determination of $A\beta_{1-42}$ in CSF by Aβ SDS-PAGE/immunoblot 2 and CCD camera: Comparison of cryoprecipitation after freezing of untreated CSF samples (native*) versus pretreatment with SDS/thermal denaturation (SDS**) for the NDC-3$^{CP}$ and AD-3$^{CP}$ groups

| P CODE | Age | Sex | Diagnosis | D code | MMSE[&] | $A\beta_{1-42}$native* pg/ml | $A\beta_{1-42}$SDS** pg/ml | $\Delta A\beta_{1-42}\%^{\$}$ | ApoE$^{\$}$ |
|---|---|---|---|---|---|---|---|---|---|
| NP45 | 76 | F | Alzheimer's dementia | AD | 5 | 1464.00 | 1431.75 | 2.25 | 3/4 |
| NP52 | 68 | F | Alzheimer's dementia | AD | 11 | 1586.00 | 1390.50 | 14.06 | 3/4 |
| NP58 | 83 | F | Alzheimer's dementia | AD | 20 | 2074.00 | 1775.50 | 16.81 | 3/4 |
| NP66 | 67 | F | Alzheimer's dementia | AD | 1 | 1498.25 | 1572.00 | −4.69 | 3/4 |
| NP69 | 62 | M | Alzheimer's dementia | AD | n.a. | 960.75 | 901.75 | 6.54 | n.a. |
| NP111 | 84 | F | Alzheimer's dementia | AD | 15 | 2020.00 | 2182.50 | −7.45 | 3/4 |
| NP143 | 55 | M | Alzheimer's dementia | AD | 27 | 886.00 | 965.00 | −8.19 | 2/4 |
| NP190 | 79 | F | Alzheimer's dementia | AD | 19 | 657.50 | 716.50 | −8.23 | 3/4 |
| NP197 | 64 | F | Alzheimer's dementia | AD | n.a. | 699.75 | 825.00 | −15.18 | n.a. |
| NP213 | 32 | M | Depressive disorder with psychotic features | NDC (OND) | 30 | 2066.50 | 2166.25 | −4.60 | 3/3 |
| NP319 | 72 | F | Alzheimer dementia | AD | 28 | 872.25 | 913.00 | −4.46 | 4/4 |
| NP320 | 70 | F | Alzheimer's dementia | AD | 25 | 1551.25 | 1705.00 | −9.02 | 2/4 |
| NP344 | 36 | F | Somatoform (conversion neurotic) disorder | NDC (OND) | 28 | 2012.00 | 2688.00 | −25.15 | 3/3 |
| NP345 | 34 | M | Panic disorder with agoraphobia | NDC (OND) | n.a. | 2879.75 | 3788.75 | −23.99 | 3/3 |
| NP352 | 45 | F | Chronic inflammatory CNS disorder | NDC (CID) | 29 | 4589.75 | 5878.75 | −21.93 | 3/3 |
| NP355 | 31 | F | Cerebral transient ischemic attacks | NDC (OND) | 30 | 4931.75 | 5266.75 | −6.36 | 3/3 |
| NP356 | 65 | F | Polycythemia vera with transient ischemic attacks | NDC (OND) | 30 | 1285.50 | 2858.00 | −55.02 | 3/4 |
| NP364 | 58 | M | Epilepsy | NDC (OND) | 28 | 2450.25 | 2982.50 | −17.85 | 2/3 |
| NP374 | 43 | M | Chronic inflammatory CNS disorder | NDC (CID) | 30 | 1562.75 | 3326.25 | −53.02 | 3/4 |
| NP402 | 66 | F | Hemicrania | NDC (OND) | 30 | 1714.50 | 3004.50 | −42.94 | 3/4 |
| NP412 | 48 | M | Depressive disorder associated with subcortical arteriosclerotic encephalopathy | NDC (OND) | 30 | 1560.25 | 2961.75 | −47.32 | 3/3 |
| NP419 | 46 | M | Chronic inflammatory CNS disorder | NDC (CID) | n.a. | 1411.75 | 2154.50 | −34.47 | 3/3 |

TABLE 21-continued

Determination of $A\beta_{1-42}$ in CSF by $A\beta$ SDS-PAGE/immunoblot 2 and CCD camera: Comparison of cryoprecipitation after freezing of untreated CSF samples (native*) versus pretreatment with SDS/thermal denaturation (SDS**) for the NDC-3$^{CP}$ and AD-3$^{CP}$ groups

| P CODE | Age | Sex | Diagnosis | D code | MMSE[&] | $A\beta_{1-42}$native* pg/ml | $A\beta_{1-42}$SDS** pg/ml | $\Delta A\beta_{1-42}$%[§] | ApoE[$] |
|---|---|---|---|---|---|---|---|---|---|
| NP421 | 60 | M | Chronic inflammatory CNS disorder with primary progressive aphasia | NDC (CID) | 30 | 2145.50 | 2967.75 | −27.71 | 3/3 |
| NP457 | 24 | M | Depressive episodes in Type I bipolar affective psychosis | NDC (OND) | 30 | 2164.67 | 2156.67 | 0.37 | 2/3 |
| NP490 | 20 | M | Chronic inflammatory CNS process | NDC (CID) | 30 | 4349.50 | 4789.75 | −9.19 | 3/3 |
| NP526 | 61 | M | Depressive disorder associated with subcortical arteriosclerotic encephalopathy | NDC (OND) | 29 | 3397.00 | 3412.75 | −0.46 | 3/3 |

[§]$\Delta A\beta_{Peptide}$% = ($A\beta_{Peptide}$Native − $A\beta_{Peptide}$SDS) / $A\beta_{Peptide}$SDS * 100: Negatives (positive) $\Delta A\beta_{1-42}$ means lower (higher) $A\beta$ peptide concentration in the CSF sample frozen untreated relative to pretreatment of the sample with SDS/thermal denaturation
[$]ApoE genotype
[&]Mini mental status examination
n.a. = not available

APPENDIX 1

CVs CCD camera

| | 80 pg | | | | | 20 pg | | | | |
|---|---|---|---|---|---|---|---|---|---|---|
| | 38 | 40 | 42 | 42/40 | 42/38 | 38 | 40 | 42 | 42/40 | 43/38 | non-adjusted band volumes (CNT mm2)

| | | | | | | | | | | |
|---|---|---|---|---|---|---|---|---|---|---|
| M1 | 50680 | 54213 | 31881 | 0.58806928 | 0.62906472 | 8664 | 8903 | 4977 | 0.5590252 | 0.57444598 |
| | 50727 | 56923 | 31162 | 0.54744128 | 0.61430796 | 9430 | 8795 | 4591 | 0.52200114 | 0.48685048 |
| | 43870 | 50150 | 28260 | 0.56360947 | 0.64417597 | 9244 | 9175 | 4672 | 0.50920981 | 0.50540891 |
| | 51055 | 55263 | 31208 | 0.5647178 | 0.61126236 | 9171 | 9717 | 4736 | 0.48739323 | 0.51641042 |
| | 49143 | 56496 | 31525 | 0.55800411 | 0.64149523 | | | | | |
| Mean | | | | 0.56434839 | 0.62806125 | | | | 0.51940731 | 0.52077895 |
| M2 | 51248 | 55952 | 30252 | 0.54067772 | 0.59030596 | 7465 | 6861 | 3844 | 0.56026818 | 0.5193637 |
| | 49591 | 53053 | 29747 | 0.56070345 | 0.59984675 | 7186 | 6968 | 3512 | 0.50401837 | 0.48872808 |
| | 43655 | 53816 | 27756 | 0.5157574 | 0.63580346 | 7080 | 8124 | 4092 | 0.50369276 | 0.5779661 |
| | 48157 | 49347 | 26700 | 0.54106633 | 0.55443653 | 7861 | 8339 | 4034 | 0.51612903 | 0.54751304 |
| | 44782 | 52359 | 26306 | 0.50241601 | 0.58742352 | | | | | |
| Mean | | | | 0.53212418 | 0.59356324 | | | | 0.52102709 | 0.5322859 |
| M3 | 53653 | 52820 | 31278 | 0.59216206 | 0.58296833 | 6872 | 7399 | 4766 | 0.6441411 | 0.693539 |
| | 56051 | 61200 | 31187 | 0.5095915 | 0.55640399 | 8417 | 9646 | 4192 | 0.43458428 | 0.49803968 |
| | 48325 | 55785 | 30675 | 0.549879 | 0.63476461 | 7904 | 8977 | 4230 | 0.47120419 | 0.53517206 |
| | 52863 | 57959 | 32800 | 0.56591729 | 0.62047179 | 10254 | 9170 | 4479 | 0.48844057 | 0.43680515 |
| | | | | | | 9466 | 8300 | 3863 | 0.46542169 | 0.40809212 |
| Mean | | | | 0.55438746 | 0.59865218 | | | | 0.50075837 | 0.5143296 |
| M4 | 42723 | 47177 | 28399 | 0.60196706 | 0.66472392 | 7688 | 7860 | 3654 | 0.4648855 | 0.47528616 |
| | 44877 | 48287 | 29121 | 0.60308157 | 0.64890701 | 7453 | 8335 | 4075 | 0.48890222 | 0.54675969 |
| | 44229 | 51395 | 30362 | 0.59075786 | 0.68647268 | 7568 | 8614 | 3987 | 0.46285117 | 0.52682347 |
| | 50143 | 56046 | 30382 | 0.54209043 | 0.60590711 | 7916 | 9015 | 4142 | 0.45945646 | 0.52324406 |
| | | | | | | 8523 | 8913 | 4239 | 0.47559744 | 0.49736008 |
| Mean | | | | 0.58447423 | 0.65150268 | | | | 0.47033856 | 0.51389469 | adjusted bandvolumes (CNT mm2) i.e. background subtraction

| | | | | | | | | | | |
|---|---|---|---|---|---|---|---|---|---|---|
| M1 | 48020 | 51697 | 29462 | 0.56989767 | 0.61353603 | 6207 | 6669 | 3051 | 0.45748988 | 0.49154181 |
| | 47825 | 54136 | 28743 | 0.53094059 | 0.60100366 | 6973 | 6957 | 2956 | 0.42489579 | 0.42392084 |
| | 41539 | 47818 | 26170 | 0.54728345 | 0.63001035 | 6922 | 6998 | 2814 | 0.40211489 | 0.4065299 |
| | 48394 | 52844 | 29118 | 0.55101809 | 0.60168616 | 7168 | 7801 | 3033 | 0.38879631 | 0.42313058 |
| | 46483 | 54078 | 29348 | 0.54269758 | 0.63137061 | | | | | |
| Mean | 46452.2 | 52114.6 | 28568.2 | 0.54836748 | 0.61552136 | 6817.5 | 7106.25 | 2963.5 | 0.41832422 | 0.43628078 |
| S.D. | 2539.82861 | 2328.44082 | 1224.02327 | 0.01270901 | 0.01317002 | 364.232412 | 420.67171 | 93.3983405 | 0.02603735 | 0.03265192 |
| CV (%) | 5.46761748 | 4.46792419 | 4.28456559 | 2.31760749 | 2.13963527 | 5.34260964 | 5.91974262 | 3.15162276 | 6.22420326 | 7.48415286 |
| M2 | 50181 | 54886 | 29320 | 0.53419816 | 0.58428489 | 6644 | 6123 | 3105 | 0.50710436 | 0.46733895 |
| | 48472 | 52069 | 28852 | 0.55411089 | 0.59523024 | 6414 | 6229 | 2853 | 0.45801894 | 0.44480823 |
| | 42537 | 52884 | 26824 | 0.50722336 | 0.63060394 | 6342 | 7300 | 3469 | 0.47520548 | 0.54698833 |
| | 47173 | 48452 | 25716 | 0.53075208 | 0.54514235 | 7090 | 7444 | 3588 | 0.48199893 | 0.50606488 |
| | 43716 | 51334 | 25374 | 0.49429228 | 0.58042829 | | | | | |
| Mean | 46415.8 | 51925 | 27217.2 | 0.52411535 | 0.58713793 | 6622.5 | 6774 | 3253.75 | 0.48058193 | 0.4913001 |
| S.D. | 2874.44084 | 2103.28068 | 1606.23366 | 0.02017224 | 0.02746477 | 292.049225 | 601.332271 | 291.883003 | 0.01763123 | 0.00389632 |
| CV (%) | 6.19280685 | 4.05061276 | 5.90153894 | 4.02053481 | 4.67773786 | 4.40995433 | 8.87706334 | 8.97066471 | 3.66872616 | 7.91905484 |
| M3 | 53368 | 51600 | 30114 | 0.58360465 | 0.56427072 | Extrem5358 | Extrem6118 | Extrem3718 | not calc | not calc |

APPENDIX 1-continued

CVs CCD camera

| | 80 pg | | | | | | 20 pg | | | | |
|---|---|---|---|---|---|---|---|---|---|---|---|
| | 38 | 40 | 42 | 42/40 | 42/38 | | 38 | 40 | 42 | 42/40 | 43/38 |
| | 54715 | 59802 | 30023 | 0.50204007 | 0.54871607 | | 6898 | 8198 | 3180 | 0.38789949 | 0.46100319 |
| | 46867 | 54448 | 29395 | 0.53987291 | 0.62720038 | | 6386 | 7459 | 3091 | 0.41439871 | 0.48402756 |
| | 51527 | 56577 | 31534 | 0.5573643 | 0.61198983 | | 8613 | 7667 | 3163 | 0.41254728 | 0.36723557 |
| | | | | | | | 7826 | 6853 | 2678 | 0.39077776 | 0.34219269 |
| Mean | 51619.25 | 55606.75 | 30266.5 | 0.54572048 | 0.58804425 | | 7430.75 | 7544.25 | 3028 | 0.40140581 | 0.41361475 |
| S.D. | 2967.9195 | 2997.42618 | 782.402869 | 0.02963512 | 0.03247491 | | 952.359526 | 311.153053 | 38.5774834 | 0.01207914 | 0.05051167 |
| CV (%) | 5.74963702 | 5.39039987 | 2.58504574 | 5.43045799 | 5.52252816 | | 12.8164657 | 4.12437357 | 1.27402521 | 3.00920886 | 12.2122495 |
| M4 | 42399 | 46878 | 28126 | 0.59998293 | 0.6633647 | | 7364 | 7590 | 3410 | 0.44927536 | 0.46306355 |
| | 44566 | 48028 | 28888 | 0.60148247 | 0.64820715 | | 7156 | 8054 | 3831 | 0.47566427 | 0.53535495 |
| | 43919 | 51085 | 30091 | 0.58903788 | 0.68514766 | | 7271 | 8343 | 3744 | 0.44875944 | 0.51492229 |
| | 49792 | 55735 | 30111 | 0.54025298 | 0.6047357 | | 7606 | 8693 | 3878 | 0.44610606 | 0.50986064 |
| | | | | | | | 8158 | 8578 | 3975 | 0.46339473 | 0.48725178 |
| Mean | 45169 | 50431.5 | 29304 | 0.58268907 | 0.6503638 | | 7511 | 8251.6 | 3767.6 | 0.45663997 | 0.50209064 |
| S.D. | 2782.58594 | 3426.30811 | 841.33198 | 0.02496697 | 0.02943431 | | 165.534551 | 404.139209 | 182.954058 | 0.01201895 | 0.02645564 |
| CV (%) | 6.16038862 | 6.79398413 | 2.87104825 | 4.28478442 | 4.52582256 | | 2.20389496 | 4.89770722 | 4.85598414 | 2.6304065 | 5.2690967 |

Intraassay CV

| M1 | 5.46761748 | 4.46792419 | 4.28456559 | 2.31760749 | 2.13965327 | | 5.34260964 | 5.91974262 | 3.15162276 | 0.62240326 | 7.48415286 |
| M2 | 6.19280685 | 4.05061276 | 5.90153894 | 4.02053481 | 4.67773786 | | 4.40995433 | 8.87706334 | 8.97066471 | 3.66872616 | 7.91905484 |
| M3 | 5.74963702 | 5.39039987 | 2.58504574 | 5.43045799 | 5.52252816 | | 12.8164657 | 4.12437357 | 1.27402521 | 3.00920886 | 12.2122495 |
| M4 | 6.16038862 | 6.79398413 | 2.87104825 | 4.28478442 | 4.52582256 | | 2.20389496 | 4.89770722 | 4.85598414 | 2.63204065 | 5.2690967 |
| Mean Intraassay CV | 5.89261249 | 5.17573024 | 3.91054963 | 4.01334618 | 4.21643546 | | 6.19323116 | 5.95472169 | 4.56307421 | 3.88354473 | 8.22113847 |
| SD Intraassay CV | 0.30119904 | 1.05258105 | 1.31733159 | 1.11326839 | 1.25771844 | | 3.99016517 | 1.8033828 | 2.84265232 | 1.40138816 | 2.5138576 |
| Mean + 2SD | 6.49501058 | 7.28089234 | 6.54521281 | 6.23988295 | 6.73187233 | | 14.17356155 | 9.56148729 | 10.2483788 | 6.68632104 | 13.2488537 |

Interassay CV

| mean M1 | 46452.2 | 52114.6 | 28568.2 | 0.54836748 | 0.61552136 | | 6817.5 | 7106.25 | 2963.5 | 0.41832422 | 0.43628078 |
| mean M2 | 46415.8 | 51925 | 27217.2 | 0.52411535 | 0.58713793 | | 6622.5 | 6774 | 3253.75 | 0.48058193 | 0.4913001 |
| mean M3 | 51619.25 | 55606.75 | 30266.5 | 0.54572048 | 0.58804425 | | 7430.75 | 7544.25 | 3028 | 0.40140581 | 0.41361475 |
| mean M4 | 45169 | 50431.5 | 29304 | 0.58268907 | 0.6503638 | | 7511 | 8251.6 | 3767.6 | 0.45663997 | 0.50209064 |
| Total Mean | 47414.0625 | 52519.4625 | 28839.975 | 0.55022309 | 0.61026684 | | 7095.4375 | 7419.025 | 3253.2125 | 0.43923798 | 0.46082157 |
| SD | 2482.21751 | 1897.90877 | 1113.27772 | 0.02097242 | 0.02580778 | | 382.76814 | 552.889655 | 315.930685 | 0.03114807 | 0.03695541 |
| Interassay CV | 5.23519263 | 3.61372467 | 3.86032347 | 3.81162188 | 4.22893412 | | 5.39456715 | 7.45232231 | 9.71134487 | 7.09138883 | 8.01946291 |

Quality criteria: CV < 15% for quadruplicate det.
Maximum 1 extreme value can bu defined and eliminated

What is claimed is:

1. A monoclonal antibody, produced by a hybridoma cell line which was deposited at the DSMZ-Deutsche Sammlung von Mikroorganismen und Zellkulturen GmbH, Braunschweig and assigned DSMZ accession number DSM ACC2485.

2. An antibody as claimed in claim 1, further comprising a detectable label.

3. A method for detecting Aβ peptides Aβ1-x and/or Aβ2-x and/or sAPPα comprising contacting a sample with the antibody of claim 1, wherein x is an integer from 2 to at least 42, and wherein the antibody specifically binds Aβ peptides Aβ1-x and/or Aβ2-x and/or sAPPα to form an antibody-peptide complex and detecting the antibody or antibody-peptide complex.

4. The method of claim 3, wherein said contacting is performed in a Western immunoblot.

5. The method of claim 4, wherein nonspecific binding sites are blocked with a blocking agent.

6. The method of any of claims 3 to 5, wherein Aβ peptides and the sAPPα are separated from one another by sodium lauryl sulfate polyacrylamide gel electrophoresis (SDS-PAGE) and inducing an amino acid primary sequence-specific conformational change in the Aβ peptides by addition of urea.

7. The method of claim 6, wherein the Aβ peptides are separated by isoelectric focusing.

8. The method of claim 6, wherein a concentration of Aβ peptide Aβ1-42 is determined in the sample.

9. The method of claim 8, wherein the sample comprises CSF, brain, plasma or mixtures thereof.

10. The method of claim 8 or 9, wherein a ratio between the concentration of the Aβ peptide Aβ2-42 to the concentration of the Aβ peptide Aβ1-42 in the sample is determined.

11. The method of claim 6, wherein at least one concentration ratio selected from the group consisting of a ratio between a concentration of Aβ peptide Aβ1-42 to a concentration of Aβ peptide Aβ1-40, a ratio between a concentration of Aβ peptide Aβ1-42 to a concentration of Aβ peptide Aβ1-38 and a ratio between a concentration of Aβ peptide Aβ1-38 to a concentration of Aβ peptide Aβ1-40 is determined in the sample.

12. The method of claim 6, wherein at least one relative proportion of at least one concentration of an Aβ peptide to a total concentration of Aβ peptides is determined, wherein the Aβ peptide is selected from the group consisting of Aβ1-42, Aβ1-40 and Aβ1-38, and the total concentration of Aβ peptides comprises at least the sum of the concentrations of Aβ1-42, Aβ1-40 and Aβ1-38.

13. The method of claims 3–5, 7–9, or 11–12, wherein the peptides are treated with a detergent.

14. The method of claim 13, wherein the Aβ peptides are disrupted by an SDS-thermal denaturation.

15. The method of claim 3, 8 or 14, wherein the sample is divided into at least two part-samples, wherein a first part-sample is subjected to a treatment with a detergent before or instead of a precipitation treatment which is directed to at least part portions of the Aβ peptide Aβ1-42 and which is carried out on a second pert-sample before or instead of the sample treatment with the detergent, and wherein a difference Δ Aβ-42 between the concentrations of the Aβ peptide Aβ1-42 is determined in the two sample parts.

16. The method of claims 3–5, 7–9, 11–12, or 14–15, wherein the Aβ peptides to which the monoclonal antibody is bound are labeled with a secondary antibody directed against the monoclonal antibody.

17. The method of claim 16, wherein the secondary antibody directed against the monoclonal antibody is labeled with a marker whose quantity can be detected.

18. The method of claims 16 or 17, wherein an amount of the labeled antibody is determined by photometry with a CCD camera.

19. A method for concentrating Aβ peptides Aβ1-x and Aβ2-x comprising contacting a sample with the antibody of claim 1 to form an antibody complex with Aβ peptides Aβ1-x or Aβ2-x in the sample and isolating the antibody complex.

20. A method for distinguishing Aβ peptides Aβ1-x and Aβ2-x from Aβ peptides Aβn-x with n>2 and x>0 comprising contacting a sample with the antibody of claim 1, wherein the antibody of claim 1 does not specifically bind to Aβn-x when n>2.

21. The antibody of claim 2, wherein the detectable label is a radioisotope.

22. The method of claim 7, wherein a concentration of the Aβ peptide Aβ1-42 is determined in a sample comprising CSF, brain, plasma or mixtures thereof.

23. The method of claim 7, wherein at least one concentration ratio selected from the group consisting of a ratio between a concentration of Aβ peptide Aβ1-42 to a concentration of Aβ peptide Aβ1-40, a ratio between a concentration of Aβ peptide Aβ1-42 to a concentration of Aβ peptide Aβ1-38 and a ratio between a concentration of Aβ peptide Aβ1-38 to a concentration of Aβ peptide Aβ1-40 is determined in the sample comprising CSF, brain, plasma or mixtures thereof.

24. The method of claim 7, wherein at least one relative proportion of at least one concentration of an Aβ peptide to a total concentration of Aβ peptides is determined.

25. The method of claim 24, wherein the Aβ peptide is selected from the group consisting of Aβ1-42, Aβ1-40 and Aβ1-38, and the total concentration of Aβ peptides comprises at least the sum of the concentrations of Aβ1-42, Aβ1-40 and Aβ1-38.

26. The method of claim 25, wherein the total concentration of Aβ peptides further comprises the concentration of Aβ1-37 or Aβ1-39.

27. The method of claim 12, wherein the total concentration of Aβ peptides further comprises the concentration of Aβ1-37 or Aβ1-39.

* * * * *